(12) United States Patent
Defossa et al.

(10) Patent No.: US 6,759,420 B1
(45) Date of Patent: Jul. 6, 2004

(54) ARYLALKANOYL DERIVATIVES, PROCESSES FOR THEIR PREPARATION, THEIR USE AND PHARMACEUTICAL COMPOSITIONS CONTAINING THEM

(75) Inventors: Elisabeth Defossa, Idstein (DE); Uwe Heinelt, Wiesbaden (DE); Otmar Klingler, Rodgau (DE); Gerhard Zoller, Schöneck (DE); Hans Matter, Langenselbold (DE); Fahad A. Al-Obeidi, Tucson, AZ (US); Armin Walser, Tucson, AZ (US); Peter Wildgoose, Oberursel (DE)

(73) Assignee: Aventis Pharma Deutschland GmbH, Frankfurt am Main (DE)

( * ) Notice: Subject to any disclaimer, the term of this patent is extended or adjusted under 35 U.S.C. 154(b) by 0 days.

(21) Appl. No.: 09/472,936

(22) Filed: Dec. 28, 1999

(30) Foreign Application Priority Data

Jan. 2, 1999 (EP) .............................. 99100001
Oct. 1, 1999 (EP) ............................ 99119538

(51) Int. Cl.$^7$ ...................... A61K 31/34; C07D 211/92
(52) U.S. Cl. ...................... 514/337; 546/224
(58) Field of Search ........................... 546/224; 514/331

(56) References Cited

U.S. PATENT DOCUMENTS

| | | | |
|---|---|---|---|
| 4,977,168 A | 12/1990 | Bernat et al. | |
| 5,424,334 A | 6/1995 | Abood et al. | |
| 5,576,342 A | * 11/1996 | M uller et al. | ............. 514/399 |
| 6,395,737 B1 | 5/2002 | Defossa et al. | |

FOREIGN PATENT DOCUMENTS

| | | |
|---|---|---|
| WO | WO 95/29189 | 11/1995 |
| WO | WO 96/19493 | 6/1996 |
| WO | WO 99/33800 | 7/1999 |
| WO | WO 97/24118 | 7/2000 |

OTHER PUBLICATIONS

Fevig et al., "Preparation of meta–Amidino–N,N–Disubstituted Anilines as Potent Inhibitors of Coagulation Factor Xa," Biooganic & Medicinal Chemistry Letters 8 (1998) 3143–3148 (1998).
Wallis, "Inhibitors of Coagulation Factor Xa: From Macromolecular Beginnings to Small Molecules," Current Drugs, 3, 1173–1179 (1993).
Co–pending U.S. patent application No. 09/473,053, filed on Dec. 28, 1999.

* cited by examiner

Primary Examiner—Ceila Chang
Assistant Examiner—Binta Robinson
(74) Attorney, Agent, or Firm—Finnegan, Henderson, Farabow, Garrett, & Dunner, L.L.P.

(57) ABSTRACT

The present invention is directed to new compounds for the inhibition of blood clotting proteins and factor Xa activity, and more particularly, to arylalkanoyl derivatives of the formula (I):

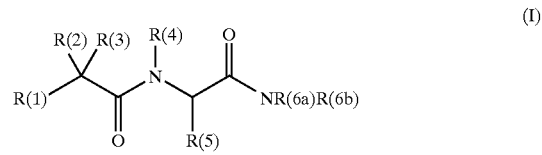

(I)

wherein R(1), R(2), R(3), R(4), R(5), R(6a), and R(6b) have the meanings indicated in the claims. The invention also relates to processes for the preparation of the compounds of formula (I), to methods of inhibiting factor Xa activity and of inhibiting blood clotting, to the use of the compounds of formula (I) in the treatment and prophylaxis of diseases whcih can be treated or prevented by the inhibition of factor Xa activity, such as cardiovascular or thromboembolic diseases, and to the use of the compounds of formula (I) in the preparation of medicaments to be applied in such diseases.

27 Claims, No Drawings

ARYLALKANOYL DERIVATIVES, PROCESSES FOR THEIR PREPARATION, THEIR USE AND PHARMACEUTICAL COMPOSITIONS CONTAINING THEM

Under the provisions of Section 119 of 35 U.S.C., Applicants hereby claim the benefit of the filing date of European Patent Application 99100001.9, filed Jan. 2, 1999, and European Patent Application 99119538.9, filed Oct. 1, 1999, which applications are hereby incorporated by specific reference.

The present invention relates to new compounds for the inhibition of blood clotting proteins and the inhibition of factor Xa activity, and more particularly, to arylalkanoyl derivatives of the formula (I):

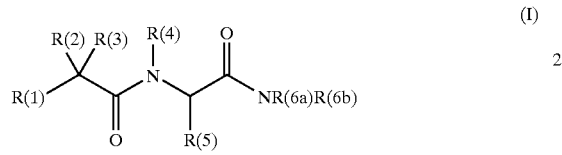

(I)

wherein R(1), R(2), R(3), R(4), R(5), R(6a) and R(6b) are defined as indicated below. The invention also relates to processes for the preparation of the compounds of formula (1), to methods of inhibiting factor Xa activity and of inhibiting blood clotting, to the use of the compounds of formula (I) in the treatment and prophylaxis of diseases which can be treated or prevented by the inhibition of factor Xa activity such as thromboembolic diseases, and to the use of the compounds of formula (I) in the preparation of medicaments to be applied in such diseases. The invention further relates to compositions containing a compound of formula (I) in admixture or otherwise in association with an inert carrier, in particular pharmaceutical compositions containing a compound of formula (I) together with pharmeceutically acceptable carrier substances and auxiliary substances.

The ability to form blood clots is vital to survival. In certain disease states, however, the formation of blood clots within the circulatory system is itself a source of morbidity. It is nevertheless not desirable in such disease states to completely inhibit the clotting system because life threatening hemorrhage would ensue. In order to reduce the instances of the intravascular formation of blood clots those skilled in the art have endeavoured to develop an effective inhibitor of factor Xa, or prothrombinase, the enzyme which is incorporated into the prothrombinase complex where it serves to activate thrombin during clot formation. Appropriate concentrations of such an inhibitor would increase the level of prothrombinase forming agents required to initiate clotting, but would not unduly prolong the clotting proces once a threshold concentration of thrombin had been obtained.

Blood coagulation is a complex process involving a progressively amplified series of enzyme activation reactions in which plasma zymogens are sequentially activated by limited proteolysis. Mechanically, the blood coagulation cascade has been divided into intrinsic and extrinsic pathways, which coverage at the activation of factor X; subsequent generation of the thrombin proceeds through a single common pathway (see Scheme 1 below):

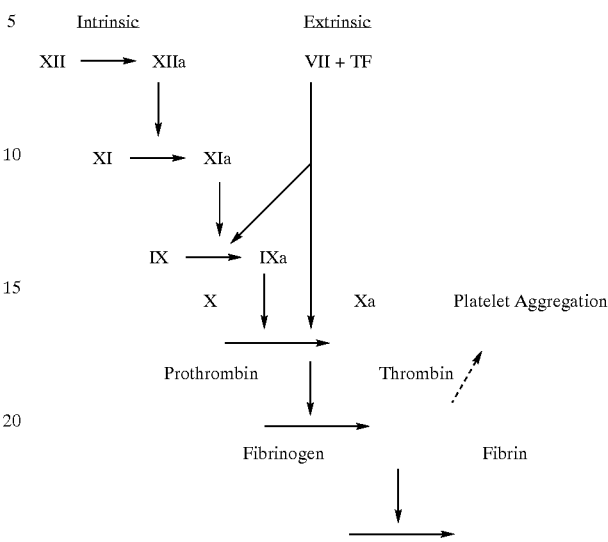

The present evidence suggests that the intrinsic pathway plays an important role in the maintenance and growth of fibrin formation, while the extrinsic pathway is critical in the initiation phase of blood coagulation. It is generally accepted that blood coagulation is physically initiated upon formation of a tissue factor ("TF")/factor Vlla complex. Once formed, this complex rapidly initiates coagulation by activating factors IX and X. The newly generated activated factor X, i.e., factor Xa, then forms a one-to-one complex with factor Va and phospholipids to form a prothrombinase complex, which is responsible for converting souble fibrinogen to insoluble fibrin via the activation of thrombin from its precursor prothrombin. As time progresses, the activity of the factor Vlla/TF complex (extrinsic pathyway) is suppressed by a Kunitz-type protease inhibitor protein TFPI, which, when complexed to factor Xa, can directly inhibit the proteolytic activity of factor Vlla/tissue factor, In order to maintain the coagulation process in the presence of an inhibited extrinsic system, additional factor Xa is produced via the thrombin-mediated activity of the intrinsic pathway. Thus, thrombin plays a dual autocatalytic role: mediateing its own production and converting fibrinogen to fibrin.

The autocatalytic nature of thrombin generation is an important safeguard against uncontrolled bleeding and it ensures that, once a given threshold level of prothrombinase is present, blood coagulation will proceed to completion, thereby effecting, for example, an end of the hemorrhage. Thus, it is most desirable to develop agents that inhibit coagulation without directly inhibiting thrombin. However, despite the long standing recognition of the desirability of such an inhibitor, there is at present no effective specific Xa inhibitor in clinical use.

In many clinical applications there is a great need for the prevention of intravascular blood clots or for anti-coagulant therapy. The currently available drugs are not satisfactory in many specific clinical applications. For example, nearly 50% of patients who have undergone a total hip replacement develop deep vein thrombosis ("DVT"). The currently approved therapies are fixed dose low molecular weight heparin ("LMWH") and variable dose heparin. Even with these drug regimes 10% to 20% of patients develop DVT and 5% to 10% develop bleeding complications.

Another clinical situation for which better anticoagulants are needed concerns subjects undergoing transluminal coronary angioplasty and subjects at risk for myocardial infarction or angina.

The most widely used blood-clotting inhibitors are heparin and the related sulfated polysaccharides: LMWH and heparin sulfate. These molecules exert their anti-clotting effects by promoting the binding of a natural regulator of the clotting process, anti-thrombin III, to thrombin and to factor Xa. The inhibitory acitivity of heparin primarily is directed toward thrombin, which is inactivated approximately 100 times faster than factor Xa. Although relative to heparin, heparin sulfate and LMWH are somewhat more potent inhibitors of Xa than of thrombin, the differences in vitro are modest (3–30 fold) and effects in vivo can be inconsequential. Hirudin and hirulog are two additional thrombin-specific anticoagulants that have been tested in clinical trials. However, these anticoagulants, which inhibit thrombin, are also associated with bleeding complications.

Preclinical studies in baboons and dogs have shown that specific inhibitors of factor Xa prevent clot formation without producing the bleeding side effects observed with direct thrombin inhibitors.

Several specific inhibitors of factor Xa have been reported. Both synthetic and protein inhibitors of factor Xa have been identified, and these include, for example, antistasin ("ATS") and tick anticoagulant peptide ("TAP"). ATS, which is isolated from the leech, *Haementerin officinalis*, contains 119 amino acids and has a Ki for factor Xa of 0.05 nM. TAP, which is isolated from the tick, *Ornithodoros moubata*, contains 60 amino acids and has a Ki for factor Xa of about 0.5 nM.

The effectiveness of recombinantly-produced ATS and TAP have been investigated in a number of animals model systems. Both inhibitors decrease bleeding time compared to other anticoagulants, and prevent clotting in a thromboplastin-induced, ligated jugular vein model of deep vein thrombosis. The results achieved in this model correlate with results obtained using the current drug of choice, heparin.

Subcutaneous ATS also was found to be an effective treatment in a thromboplastin-induced model of disseminated intravascular coagulation ("DIC"). TAP effectively prevents "high-shear" arterial thrombosis and "reduced flow" caused by the surgical placement of a polyester ("DACRON") graft at levels that produced a clinically acceptable prolongation of the activated partial thromboplastin time ("aPTT"), i.e., less than about two fold prolongation. By comparison, standard heparin, even at doses causing a five fold increase in the aPTT, did not prevent thrombosis and reduced flow within the graft. The aPTT is a clinical assay of coagulation which is particularly sensitive to thrombin inhibitors.

ATS and TAP have not been developed clinically. One major disadvantage of these two inhibitors is that administration of the required repeated doses causes the generation of neutralizing antibodies, thus limiting their potential clinical use. Moreover, the sizes of TAP and ATS render oral administration impossible, further restricting the number of patients able to benefit from these agents.

A specific inhibitor of factor Xa would have substantial practical value in the practice of medicine. In particular, a factor Xa inhibitor would be effective under circumstances where the present drugs of choice, heparin and realted sulfated polysaccharides, are ineffective or only marginally effective. Thus, there exists a need for a low molecular weight, factor Xa-specific blood clotting inhibitor that is effective, but does not cause unwanted side effects.

Low molecular weight, factor Xa-specific blood clotting inhibitors, that are effective but do not cause unwanted side effects have been described in International Application WO 9529189. Indole derivatives as low molecular weight, factor Xa-specific blood clotting inhibitors have been proposed in International Application 99338000. However, besides being an effective factor Xa-specific blood clotting inhibitor, it is desirable that such inhibitors will also have advantageous pharmacological properties, for instance high stability in plasma and liver and high selectively versus other serine proteases. Thus there exists an ongoing need for novel low molecular weight, factor Xa-specific blood clotting inhibitors that are effective and which will have the above advantages as well.

The present invention satisfies this need by providing novel factor Xa activity inhibiting arylalkanoyl derivatives of formula (I) and by providing related advantages as well.

The present invention provides new arylalkanoyl derivatives of formula (I) which inhibit factor Xa activity but do not substantially inhibit the acitivity of other proteases, especially those involved in the blood coagulation pathway. Thus, a subject of the present invention are compounds of the formula (I):

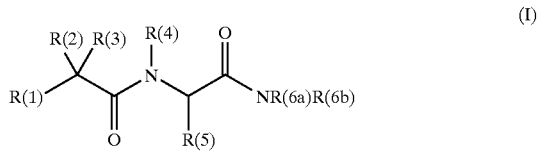

(I)

in any stereoisomeric form, physiologically acceptable salts thereof, and mixtures of any of the foregoing in any ratio, wherein:

R(1) is $(C_1C_{10})$-alkyl, $(C_3-C_7)$-cycloalkyl, $(C_3-C_7)$-cycloalkyl-$(C_1-C_4)$-alkyl, heteroalkyl, $(C_6-C_{10})$-aryl, or heteroaryl, wherein cycloalkyl in any of the foregoing is unsubstituted or substituted by one or two identical or different residues R(7) or annelated to a phenyl ring; and wherein aryl and heteroaryl are unsubstituted or substituted by 1,2, or 3 identical or different residues R(8), the substitution by these residues at a nitrogen atom of the heteroaryl residues leading to a positively charged nitrogen atom having $X^-$ as the counterion; and wherein the heteroalkyl optionally has a nitrogen atom which is unsubstituted or substituted with one or two residues R(9);

R(2) is hydrogen or $(C_1-C_4)$-alkyl;

R(3) is $(C_6-C_{10})$-aryl-$(C_1-C_4)$-alkyl which is substituted in the aryl or alkyl moiety by a residue R(11); heteroaryl-$(C_1-C_4)$-alkyl; $(C_3-C_7)$-cycloalkyl-$(C_1-C_4)$-alkyl; heteroaryl-$(C_1-C_4)$-alkyl or $(C_3-C_7)$-cycloalkyl-$(C_1-C_4)$-alkyl, which is substituted in the heteroaryl, cycloalkyl or alkyl part by 1,2, or 3 identical or different residues R(11); or heteroalkyl-$(C_1-C_4)$-alkyl which is unsubstituted or substituted by a residue R(23);

R(4) is hydrogen, $(C_1-C_4)$-alkyl, $(C_3-C_7)$-cycloalkyl, $(C_3-C_7)$-cycloalkyl-$(C_1-C_4)$-alkyl, or $(C_6-C_{10})$-aryl-$(C_1-C_4)$-alkyl;

R(5) is hydrogen, $(C_1-C_{10})$-alkyl, $(C_3-C_7)$-cycloalkyl, $(C_3-C_7)$-cycloalkyl-$(C_1-C_4)$-alkyl, $(C_6-C_{10})$-aryl, $(C_6-C_{12})$-aryl-$(C_1-C_4)$-alkyl, or a residue of the α-C-atom of a natural amino acid, wherein alkyl, cycloalkyl and aryl are unsubstituted or substituted with hydroxy, benzyloxy, hydroxycarbonyl, or $N(R(9))_2$; or R(4) and R(5) form together with the —N—CH group to which they are bound a 5- to 6-membered, heterocyclic ring or a residue of the formul (II) or (III):

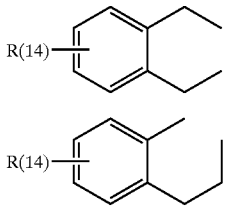

R(6a) and R(6b) independently of each other are hydrogen; $(C_1-C_8)$-alkyl which is unsubstituted or substituted by 1,2, or 3 identical or different residues R(15); $(C_6-C_{14})$-aryl or heteroaryl, wherein the aryl or heteroaryl is unsubstituted or substituted by 1,2, 3,4, or 5 identical or different residues R(16), the substitution by these residues at a nitrogen atom of the heteroaryl residue leading to a positively charged nitrogen atom having $X^-$ as the counterion;

R(7) is $(C_1-C_6)$-alkyl, $(C_1-C_6)$-alkoxy, or $(C_1-C_6)$-alkyl, in which 1 or more hydrogen atoms have been independently replaced by fluoro, chloro, or bromo;

R(8) is $(C_1-C_{10})$-alkyl, $(C_1-C_6)$-alkoxy, $(C_3-C_{10})$-cycloalkyl, $(C_3-C_7)$-cycloalkyl-$(C_1-C_4)$-alkyl, $SO_2$-$(C_1-C_4)$-alkyl, fluoro, chloro, bromo; or $(C_1-C_{10})$-alkyl, $(C_1-C_6)$-alkoxy, $(C_3-C_{10})$-cycloalkyl, $(C_3-C_7)$-cycloalkyl-$(C_1-C_4)$-alkyl or $SO_2$-$(C_1-C_4)$-alkyl in which 1 or more hydrogen atoms in the alkyl part or cycloalkyl part have been replaced by fluoro, chloro, or bromo; or two residues R(8) form a —O-$(CH_2)_2$-O-bridge or a —$(CH_2)_4$-bridge;

R(9) is R(10) or $(C_6-C_{10})$-aryl-$(C_1-C_4)$-alkyl;

R(10) is hydrogen, nitro, $(C_1-C_6)$-alkyl, $(C_1-C_6)$-alkylcarbonyl, $(C_1-C_6)$-alkoxycarbonyl, $(C_1-C_{18})$-alkylcarbonyloxy-$(C_1-C_6)$-alkoxycarbonyl, $(C_6-C_{14})$-arylcarbonyl which is optionally substituted, $(C_6-C_{14})$-aryloxycarbonyl which is optionally substituted, or $(C_6-C_{14})$-aryl-$(C_1-C_6)$-alkoxycarbonyl which is optionally substituted in the aryl moiety;

R(11) is R(12), $(C_1-C_4)$-alkyl which is unsubstituted or substituted by a residue R(12); or heteroaryl which is unsubstituted or substituted by $N(R(9))_2$ or $(C_1-C_4)$-alkyl;

R(12) is $N(R(9))_2$, $CON(R(9))_2$, CN, chloro, NR(10)-C(=NR(13))-NHR(10), C(=NR(13))-NHR(10), or $S(O)(=NR(9))-N(R(9))_2$;

R(13) is R(10), cyano, nitro, amino, hydroxy, $(C_1-C_6)$-alkoxy, or $(C_6-C_{14})$-aryl-$(C_1-C_6)$-alkoxy which is unsubstituted or substituted in the aryl moiety, for example, by $(C_1-C_4)$-alkoxy, usually methoxy, chloro, or $(C_1-C_4)$-alkyl, usually methyl;

R(14) is hydrogen, hydroxy, $(C_1-C_4)$-alkyl, $(C_1-C_4)$-alkoxy, fluoro, chloro, bromo, $N(R(9))_2$, nitro, or cyano;

R(15) is $(C_8-C_{10})$-aryl which is unsubstituted or substituted by 1,2, or 3 identical or different residues (R(11) or R(21), heteroaryl which is unsubstituted or substituted by 1, 2, or 3 identical or different residues R(11) or R(22), the substitution by these residues at a nitrogen atom of the heteroaryl residue leading to a positively charged nitrogen atom having $X^-$ as the counterion, or heteroaryl is substituted by one residue $N(R(9))_2$;

O-heteroaryl, S-heteroaryl, $(C_3-C_7)$-cycloalkyl, which is unsubstituted or substituted with a residue R(23); heteroalkyl which is unsubstituted or subsituted with a residue R(23); COOR(17); CONR(17)R(18); CON(R(18))_2; oxo; OH; NR(19)R(20); R(12); or the residue of the α-C-atom of a natural amino acid;

R(16) is $(C_1-C_6)$-alkyl, $(C_6-C_{10})$-aryl, heteroaryl, heteroaryl, COOR(17), $CON(R(18))_2$, OR, NR(19)R(20), (R12), (R22), or $C(O)—(CH_2)_2—NH_2$;

R(17) is hydrogen, $(C_1-C_6)$-alkyl, $(C_6-C_{10})$-aryl, $(C_6-C_{10})$-aryl-$(C_1-C_4)$-alkyl, heteroaryl, or heteroaryl-$(C_1-C_4)$-alkyl;

R(18) is hydrogen, $(C_1-C_6)$-alkyl, $(C_3-C_{10})$-cycloalkyl, $(C_3-C_{10})$-cycloalkyl-$(C_1-C_4)$-alkyl, heteroalkyl, heteroalkyl-$(C_1-C_4)$-alkyl, $(C_6-C_{10})$-aryl, $(C_6-C_{10})$-aryl-$(C_1-C_4)$-alkyl, heteroaryl, or heteroaryl-$(C_1-C_4)$-alkyl; where alkyl and/or aryl in the foregoing radicals are unsubstituted or substituted by 1,2, or 3 identical or different residues R(24);

or two residues R(18) form together with the nitrogen atom to which they are bound a 5- or 6-membered, saturated or unsaturated, heterocyclic ring, which does not or does contain an additional nitrogen-, sulfur-, or oxygen atom, and which ring is optionally substituted by $(C_6-C_{12})$-aryl, usually phenyl, $(C_6-C_{10})$-aryl-$(C_1-C_4)$-alkyl, usually benzyl, or naphthyl-sulfonyl which is substituted in the naphthyl part with chloro, usually 7-chloro-naphthalene-2-sulfonyl;

R(19) is hydrogen or R(20);

R(20) is $(C_6-C_{10})$-aryl, amidino, acetimido, R(25), or 2-pyridyl which is unsubstituted or substituted by a residue R(26);

R(21) is $(C_1-C_4)$-alkyl which is unsubstituted or substituted by a residue R(28); cyano, $CON(R(9))_2$, hydroxycarbonyl, $(C_1-C_6)$-alkoxycarbonyl, $N(R(9))_2$, $S(O)_r$-$(C_1-C_4)$-alkyl, $S(O)_r$-$N(R(9))_2$, OR(17), R(11), or two residues R(21) form a —O—$CH_2$—O-bridge;

R(22) is hydrogen, $(C_1-C_6)$-alkyl, $(C_3-C_7)$-cycloalkyl, $(C_3-C_7)$-cycloakyl-$(C_1-C_4)$-alkyl, or $(C_1-C_4)$-alkylcarbonyl, where alkyl in any of the foregoing is unsubstitued or substituted by a residue $N(R(9))_2$; $(C_1-C_6)$-alkoxy, $(C_1-C_6)$-alkylthio, fluoro, chloro, bromo, nitro, $N(R(9))_2$, or two residues R(22) form a -$(CH_2)_q$-bridge where q is 3 or 4;

R(23) is hydrogen, -(=NR(9))-R(39), R(9), oxo, R(11), —NH-S(O)(=NR(9))-$(C_1-C_4)$-alkyl, or -S(O)(=NR(9))-$N(R(9))_2$;

R(24) is $(C_1-C_4)$-alkyl; $(C_1-C_4)$-alkyl in which 1 or more hydrogen atoms have been independently replaced by fluoro or chloro, $(C_6-C_{10})$-aryl, OR(17), $N(R(9))_2$, $CON(R(9))_2$, fluoro, chloro, bromo, nitro, cyano, or $S(O)_r$-$N(R(9))_2$;

R(25) is hydrogen, $(C_1-C_4)$-alkoxycarbonyl, $(C_6-C_{10})$-aryl-$(C_1-C_4)$-alkylcarbonyl, $(C_1-C_4)$-alkylcarbonyl, or $SO_2R(27)$;

R(26) is $N(R(9))_2$ or nitro;

R(27) is $(C_1-C_4)$-alkyl or $(C_6-C_4)$-aryl, which is unsubstituted or substituted by 1,2, or 3 identical or different substituents, which are fluoro, chloro, bromo, or $(C_1-C_4)$-alkoxy;

R(28) is fluoro, chloro, bromo, or NHR(25);

R(39) is hydrogen, $(C_6-C_{10})$-aryl, heteroaryl, or $(C_1-C_6)$-alkyl, which is unsubstituted or substituted by cyano;

r is 0, 1, or 2; and $X^-$ is a physiologically acceptable anion.

Alkyl residues present in the compounds of formula (I) can be saturated or unsaturated and straight-chain or branched. This also applies when they carry subsitutents or appear as substituents in other residues such as, for example, in alkoxy residues, alkylcarbonyl reidues, alkoxycarbonyl residues, heteroalkyl-alkyl residues, cycloalky-alkyl residues, arylalkyl residues, heteroarylalkyl residues, and arylalkylcarbonyl residues. Examples of alkyl residues are methyl, ethyl, n-propyl, n-butyl, n-pentyl, n-hexyl, n-heptyl, n-octyl, n-nonyl, n-decyl, isopropyl, isobutyl, isopentyl, isohexyl, isooctyl, isononyl, isodecyl, neopentyl, 3-methylpentyl, sec-butyl, tert-butyl, and tert-pentyl. Examples of alkenyl residues are vinyl, 1-propenyl, 2-propenyl (i.e. allyl), butenyl, 3-methyl-2-butenyl, pentenyl, hexenyl, heptenyl, octenyl, nonenyl, and decenyl. Examples of alkynyl residues are ethynyl, 1-propynyl, 2-propynyl (i.e. propargyl), butynyl, pentynyl, and hexynyl.

Cycloalkyl residues present in the compounds of formula (I) can be mono-, di-, or tricyclic and are connected in the ring. This also applies when they carry substituents or appear as substituents in other residues. Examples of cycloalkyl residues are cyclopropyl, methyl-cyclopropyl, ethyl-cyclopropyl, dimethyl-cyclopropyl, propyl-cyclopropyl, methyl-ethyl-cyclopropyl, butyl-cyclopropyl, methyl-propyl-cyclopropyl, diethyl-cyclopropyl, pentyl-cyclopropyl, hexyl-cyclopropyl, heptyl-cyclopropyl, cyclobutyl, methyl-cyclobutyl, ethyl-cyclobutyl, cyclopentyl, methyl-cyclopentyl, ethyl-cyclopentyl, dimethyl-cyclopentyl, propyl-cyclopentyl, butyl-cyclopentyl, methyl-propyl-cyclopentyl, diethyl-cyclopentyl, cyclohexyl, methyl-cyclohexyl, ethyl-cyclohexyl, propyl-cyclohexyl, cycloheptyl, octahydro-indene, bicyclo[4.2.0]octane, octahydro-pentalene, bicyclo[3.3.1]nonane, tetradecahydro-phenanthrene, dodecahydro-phenalene, octahydro-1,4-ethano-indene, tetradecahydro-phenanthrene, adamantyl, and methyl-adamantyl, where ethyl, propyl, butyl, pentyl, hexyl, and heptyl can be straight-chain or branched as described above.

Examples of heteroalkyl are pyrrolidine, piperidine, tetrahydrofurane, perhydropyrane, tetrahydrothiophene, perhydrothiopyrane, pyrazolidine, imidazolidine, imidazolidine-2,4-dione, hexahydropyrazine, hexahydropyrimidine, piperazine, dioxolane, perhydrodioxane, oxazolidine, isoxazolidine, thiazolidine, isothiazolidine, perhydro-1,2-oxazine, perhydro-1,3-oxazine, per-hydro-1,4-oxazine, perhydro-1,3-thiazine, and perhydro-1,4-thiazine. Substituents present in heteroalkyl can be bound to any position unless stated otherwise.

Examples of O-heteroaryl are 2-, 3-, or 4-pyridyloxy, 2-, 3-, 4-, 5-, 6-, 7-, or 8-quinolyloxy. Examples of S-heteroaryl are 2-, 3-, or 4-pyridylthio, 2-, 3-, 4-, 5-, 6-, 7-, or 8-quinolylthio.

Examples of aryl are phenyl, naphthyl, or 9-fluorenyl residues.

Arylalkyl residues present in the compounds of formula (I) can consist of an alyl residue, which can contain one to three aryl moieties. Examples of arylalkyl residues are phenyl-methyl, phenyl-ethyl, phenyl-propyl, phenyl-butyl, naphthyl-methyl, naphthyl-ethyl, naphthyl-propyl, naphthyl-butyl, diphenyl-methyl, diphenyl-ethyl, diphenyl-propyl, diphenyl-butyl, naphthyl-phenyl-methyl, naphthyl-phenyl-butyl, dinaphthyl-butyl, and triphenyl-ethyl.

Examples of heteroaryl residues are pyridyl, pyridazinyl, pyrimidyl, pyrazinyl, furanyl, pyrrolyl, imidazolyl, 1H-pyrazolyl, thiazolyl, oxazolyl, thiophenyl, 1H-benzoimidazolyl, benzothiazolyl, benzofuranyl, indolyl, thieno[3,2-c]pyridinyl, thieno[2,3-c]pyridinyl, furo[3,2-c]pyridinyl, furo[2,3-c]pyridinyl, 3H-imidazo[4,5-c]pyridinyl, [1,2,4]oxadiazolyl, quinolinyl, and isoquinolinyl. The residues can be bound at every possible position.

Examples of pyridyl reidues are 2-pyridyl, 3-pyridyl, and 4-pyridyl. This also applies to pyridyl residues in which the nitrogen atom is substituted by an alkyl group, etc., this substitution leading to a positively charged pyridinium group. This pyridinium group has an $X^-$ as counterion.

In monosubstituted phenyl residues the substituent can be located in the 2-position, the 3-position, or the 4-position. If phenyl is substituted twice, the substituents can be in the 2,3-position, the 2,4-position, the 2,5-position, the 2,6-position, the 3,4-position, or the 3,5-position. In phenyl residues carrying three substituents, the substituents can be in the 2,3,4-position, 2,3,5-position, 2,3,6-position, 2,4,5-position, 2,4,6-position, or 3,4,5-position. In phenyl residues carrying four substituents, the substituents can be in the 2,3,4,5-position, 2,3,4,6-position, or the 2,3,5,6-position.

Naphthyl residues can be 1-naphthyl and 2-naphthyl. In substituted naphthyl residues the substituents can be in any position, i.e., in monosubstituted 1-naphthyl residues in the 2-, 3-, 4-, 5-, 6-, 7-, or 8-position and in monosubstituted 2-naphthyl residues in the 1-, 3-, 4-, 5-, 6-, 7-, or 8-position.

Examples of the 5- or 6-membered, saturated or unsaturated, heterocyclic ring that can be formed by two residues R(18) together with the nitrogen atom to which they are bound, which can contain an atom of the group N, S, or O are imidazolidine, 2,3-dihydro-1H-imidazole, thiazolidine, 2,3-dihydro-thiazole, oxazolidine, 2,3-dihydro-oxazole, piperazine, 1,2,3,4-tetrahydro-pyrazine, hexahydro-pyrimidine, 1,2,3,4-tetrahydro-pyrimidine, 1,2-dihydro-pyrimidine, hexahydro-pyridazine, 1,2,3,4-tetrahydro-pyridazine, and 1,2,3,6-tetrahydro-pyridazine. Substituents present in this ring can be bound to any position unless stated otherwise.

Examples of a residue of the α-C-atom of a natural amino acid are hydrogen, methyl, isopropyl, butyl, isobutyl, aminobutyl, hydroxymethyl, 1-hydroxyethyl, benzyl, 4-hydroxybenzyl, indol-3-yl-methyl, thiomethyl, methylthioethyl, imidazol-4-ylmethyl, hydroxycarbonylmethyl, hydroxycarbonylethyl, aminocarbonylmethyl, aminocarbonylethyl, and 3-guanidinopropyl.

In compounds of the formula (I) where two residues R(8) or R(21) form a O—CH$_2$—O-bridge, the residues are vicinal.

In compounds of the formula (I) where two residues R(8) form a -(CH$_2$)$_4$-bridge, the residues are vicinal.

In compounds of the formula (I) where two residues R(22) form a (CH$_2$)$_q$-bridge, the residues are vicinal.

Examples of the 5- to 6-membered heterocyclic ring that can be formed by R(4) and R(5) together with a —N-CH-group to which they are bound, are pyrrolidinyl and piperidinyl.

A typical ($C_6$-$C_{10}$)-aryl-($C_1$-$C_4$)-alkyl residue in compounds of formula (I) is benzyl (phenylmethyl).

($C_1$-$C_4$)-alkyl having 1,2,3, or 4 carbon atoms.

($C_6$-$C_6$)-alkyl means alkyl having 1, 2, 3, 4, 5, or 6 carbon atoms.

($C_1$-$C_8$)-alkyl means alkyl having 1,2,3,4,5,6,7, or 8 carbon atoms.

($C_1$-$C_{10}$)-alkyl means alkyl having 1,2,3,4,5,6,7,8,9, or 10 carbon atoms.

($C_1$-$C_{12}$)-alkyl means alkyl having 1,2,3,4,5,6,7,8,9,10,11, or 12 carbon atoms.

($C_6$-$C_{10}$)-aryl means aryl having 6,7,8,9, or 10 carbon atoms.

($C_6$-$C_{14}$)-aryl means aryl having 6,7,8,9,10,11,12,13, or 14 carbon atoms.

($C_1$-$C_4$)-alkoxy means alkoxy having 1,2,3, or 4 carbon atoms.

($C_1$-$C_6$)-alkylthio means alkylthio having 1,2,3,4,5, or 6 carbon atoms.

($C_1$-$C_6$)-alkoxy means alkoxy having 1,2,3,4,5, or 6 carbon atoms.

($C_1$-$C_4$)-alkoxycarbonyl means alkoxycarbonyl having 1,2,3, or 4 carbon atoms in the alkoxy part.

($C_1$-$C_6$)-alkoxycarbonyl means alkoxycarbonyl having 1,2,3,4,5, or 6 carbon atoms in the the alkoxy part.

($C_1$-$C_4$)-alkylcarbonyl means alkylcarbonyl having 1,2,3, or 4 carbon atoms in the alkyl part.

($C_1$-$C_6$)-alkylcarbonyl means alkylcarbonyl having 1,2,3,4,5, or 6 carbon atoms in the alkyl part.

($C_6$-$C_{10}$)-aryl-($C_1$-$C_4$-alkyl means aryl-alkyl having independently from each other 6,7, 8,9, or 10 carbon atoms in the aryl part and 1,2,3, or 4 carbon atoms in the alkyl part.

($C_6$-$C_{10}$)-aryl-($C_1$-$C_4$)-alkylcarbonyl means arylalkylcarbonyl having independently from each other 6,7, 8,9, or 10 carbon atoms in the aryl part and 1,2,3, or 4 carbon atoms in the alkyl part.

($C_6$-$C_{14}$)-aryl-($C_1$-$C_6$)-alkoxy means aryl-alkoxy having independently from each other 6, 7,8,9,10,11,12,13, or 14 carbon atoms in the aryl part and 1,2,3,4,5, or 6 carbon atoms in the alkoxy part.

Heteroaryl-($C_1$-$C_4$)-alkyl means heteroaryl-alkyl having 1,2,3, or 4 carbon atoms in the alkyl part.

($C_1$-$C_{18}$)-alkylcarbonyloxy-($C_1$-$C_6$)-alkoxycarbonyl means alkylcarbonyloxy-alkoxycarbonyl having independently from each other 1,2,3,4,5,6,7,8,9,10,11,12, 13,14,15,16, 17, or 18 carbon atoms in the alkyl part and 1,2,3,4,5, or 6 carbon atoms in the alkoxy part.

($C_6$-$C_{14}$)-arylcarbonyl means arylcarbonyl having 6,7,8,9, 10,11,12,13, or 14 carbon atoms in the aryl part.

($C_6$-$C_{14}$)-aryloxycarbonyl means aryloxycarbonyl having 6,7,8,9,10,11,12,13, or 14 carbon atoms in the aryl part.

($C_6$-$C_{14}$)-aryl-($C_1$-$C_6$)-alkoxy means aryl-alkoxy having independently from each other 6, 7,8,9,10,11,12,13, or 14 carbon atoms in the aryl part and 1,2,3,4,5, or 6 carbon atoms in the alkoxy part.

($C_6$-$C_{14}$)-aryl-($C_1$-$C_6$)-alkoxycarbonyl means arylalkoxycarbonyl having independently from each other 6,7,8,9,10,11,12,13, or 14 carbon atoms in the aryl part and 1,2, 3,4,5, or 6 carbon atoms in the alkoxy part.

($C_3$-$C_7$)-cycloalkyl means cycloalkyl having 3,4,5,6, or 7 carbon atoms.

($C_3$-$C_{10}$)-cycloalkyl means cycloalkyl having 3,4,5,6,7,8,9, or 10 carbon atoms.

($C_3$-$C_7$)cycloalkyl-($C_1$-$C_4$)-alkyl means cycloalkyl-alkyl having independently from each other 3,4,5,6, or 7 carbon atoms in the cycloalkyl part and 1,2,3, or 4 carbon atoms in the alkyl part.

($C_3$-$C_{10}$)-cycloalkyl-($C_1$-$C_4$)-alkyl means cycloalkyl-alkyl having independently from each other 3,4,5,6,7,8,9, or 10 carbon atoms in the cycloalkyl part and 1,2,3, or 4 carbon atoms in the alkyl part.

It is understood that residues and variables present more that one time in a compound of formula (I), e.g. the residues R(7), R(8), R(9), R(10), R(11), R(12), R(13), R(14), R(15), R(16), R(17), R(18), R(19), R(20), R(21), R(22), R(23), R(24), R(25), R(26), R(27), R(28), R(39), and variable r are independent of one another and can be identical or different. Moreover, independently substituted means that the various possible substituents may be identical or different.

Physiologically acceptable anions $X^-$, which are present in the compounds of formula (I) if a positively charged group is present, can be anions derived from suitable inorganic acids or organic carboxylic acids or sulfonic acids. Suitable acids are, in particular, pharmaceutically utilizable or non-toxic salts. Examples of such acids are those given below as examples of acids which can form physiologically acceptable salts with the compounds of formula (I) containing basic groups. If a compound of formula (I) contains an anion $X^{31}$ and simultaneously is present as an acid addition salt formed at a basic group, the anion $X^-$ can be the same or different as the anion introduced by salt formation. The present invention also covers inner salts (or betaines) of the compounds of formula (I).

Physiologically acceptable salts of the compounds of formula (I) are, in particular, pharmaceutically utilizable or non-toxic salts. Such salts are formed, for example, from compounds of formula (I) which contain acid groups, for example carboxylic acid groups. Examples of such salts are, for example, salts containing cations of alkali metals or alkaline earth metals, such as, for example, sodium, potassium, magnesium or calcium, or the unsubstituted ammonium cation or organic ammonium cations, the latter including cations obtained from physiologically acceptable organic amines, such as, for example, methylamine, ethylamine, triethylamine, ethanolamine, tris(2-hydroxyethyl)amine, or amino acids by protonation, or suitable quaternary ammonium cations like, for example, tetramethylammonium.

Compounds of formula (I) which contain basic groups, for example, an amino group, an amidino group, or a guanidino group, form acid addition salts with, for example, inorganic acids, organic carboxylic, and organic sulfonic acids. Examples of such acids, the anions of which can be present in physiologically acceptable salts of the compounds of formula (I), are hydrochloric acid, hydrobromic acid, sulfuric acid, phosphoric acid, acetic acid, benzoic acid, oxalic acid, malonic acid, succinic acid, maleic acid, fumaric acid, malic acid, tartaric acid, citric acid, methanesulfonic acid, p-toluenesulfonic acid, or naphthalenesulfonic acids.

Physiologically acceptable salts of the compounds of formula (I) can be prepared according to standard procedures, for example, by combining the compound of formula (I) with the desired base, for example, an alkaline metal hydroxide or carbonate or hydrogen carbonate or an amine, or with the desired acid in a solvent or diluent. A physiologically acceptable salt of a compound of formula (I) can also be prepared from another salt, for example, trifluoroacetic acid salt by cation exchange or anion exchange by standard procedures. The present invention also coves, in general, salts of the compounds of formula (I) which are, for example, obtained during the chemical synthesis of the compounds and which can be used as starting materials for the subsequent preparation of a desired physiologically acceptable salt. The present invention further covers solvates of the compounds of formula (I), for example hydrates or alcoholates.

The compounds of formula (I) according to the inventin can contain optically active carbon atoms which, independently of one another, can have R or S configuration. They can thus be present in the form of individual enantiomers or individuals diastereomers or in the form of enantiomeric mixtures including racemates, or diastereomeric mixtures. The present invention relates both to pure enantiomers and mixtures of enantiomers in all ratios and to pure diastereomers and mixtures of diastereomers in all ratios. The invention covers mixtures of two stereoisomers as well as mixtures of more than two stereoisomers of formula (I), and all ratios of stereoisomers in the mixtures.

The compounds of formula (I) can also be present as E isomers or Z isomers. The present invention relates to both pure E and Z isomers and to mixtures of E/Z isomers in all ratios. Diastereomers, including E/Z isomers, can be separated into the individual isomers, for example, by chromatography. Racemates can be separated into the two enantiomers by chromatography on chiral phases or by resolution according to standard procedures. Pure enantiomers can otherwise also be obtained by employing into the synthesis optically active starting materials.

The compounds of formula (I) according to the invention can further contain mobile hydrogen atoms, i.e. they can be present in various tautomeric forms. The present invention also relates to all these tautomers.

The present invention further covers derivatives of the compounds of formula (I) in which functional groups are masked or protected by suitable groups, for example common protective groups, as well as other derivatives and prodrugs of the compounds of the formula (I) and metabolites of the compounds of formula (I).

Currently preferred compounds are compounds of the formula (I) in any stereoisomeric form, physiologically acceptable salts thereof, and mixtures of any of the foregoing in any ratio, wherein:

R(1) is ($C_3$-$C_7$)-cycloalkyl, typically cyclohexyl, ($C_6$-$C_{10}$)-aryl, typically phenyl or 2-naphthyl, heteroaryl, typically pyridyl, currently preferably 3-pyridyl, 1-1,2,3,4-tetrahydro-naphthalene or 2-1,2,3,4-tetrahydro-naphthalene, wherein aryl in any of the foregoing is unsubstituted or substituted by a residue R(8);

R(2) is hydrogen or ($C_1$-$C_4$)-alkyl, typically methyl;

R(3) is ($C_6$-$C_{10}$)-aryl-($C_1$-$C_4$)-alkyl, typically benzyl, which is substituted in the aryl moiety by a residue R(11); heteroaryl-($C_1$-$C_4$)-alkyl, typically isoquinolinmethyl, which is substituted in the heteroaryl moiety by a residue R(11), typically by N(R(9))$_2$; ($C_3$-$C_7$)-ccloalkyl-($C_1$-$C_4$)-alkyl which is unsubstituted or substituted by 1,2, or 3 identical or different residues R(11); or heteroalkyl-($C_1$-$C_4$)-alkyl which is unsubstituted or substituted by a residue R(23);

R(4) is hydrogen, ($C_3$-$C_7$)-cycloalkyl-($C_1$-$C_4$)-alkyl, typically cyclohexylmethyl, or ($C_1$-$C_4$)-alkyl, typically methyl;

R(5) is hydrogen, ($C_3$-$C_7$)-cycloalkyl, typically cyclohexyl; ($C_3$-$C_7$)-cycloalkyl-($C_1$-$C_4$)-alkyl, typically cyclohexylmethyl, ($C_1$-$C_4$)-alkyl, typically methyl or butyl, ($C_6$-$C_{10}$)-aryl, typically phenyl, ($C_6$-$C_{10}$-aryl-($C_1$-$C_4$)-alkyl, typically phenylmethyl, phenylethyl or naphthylmethyl; wherein alkyl in any of the foregoing is unsubstituted or substituted by hydroxy, benzyloxy, hydroxycarbonyl, or N(R(9))$_2$; and aryl in any of the foregoing is unsubstituted or substituted with amino; or R(4) and R(5) together with the —N-CH group to which they are bound form a residue of the formula (II) or (III);

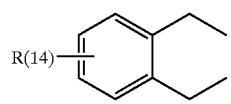

(II)

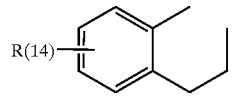

(III)

R(6a) and R(6a) independently of each other are hydrogen, or methyl, ethyl, or butyl, any of which is substituted by one or two identical or different residues R(15);

R(8) is ($C_1$-$C_6$)-alkyl, typically methyl, ($C_1$-$C_4$)-alkoxy, typically $OCH_3$, $SO_2$-($C_1$-$C_4$)-alkyl, typically $SO_2CH_3$, fluoro, chloro, bromo; or ($C_1$-$C_6$)-alkyl or ($C_1$-$C_4$)-alkoxy in which 1 or more hydrogen atoms in the alkyl part have been independently replaced by fluoro, chloro, or bromo, typically $CF_3$ or $OCF_3$;

R(9) is R(10);

R(10) is hydrogen, nitro, or benzyloxycarbonyl;

R(11) is R(12), methyl which is substituted by R(12), or heteroaryl which is unsubstituted or substituted by N(R(9))$_2$ or ($C_1$-$C_4$)-alkyl;

R(12) is CN, N(R(9))$_2$, -NR(10)-C(=NR(13))-NHR(10), -C(=NR(13))-NHR(10), S(O)(=NR(9))-N(R(9))$_2$, or CON(R(9))$_2$;

R(13) is R(10) or hydroxy;

R(14) is hydrogen;

R(15) is ($C_6$-$C_{10}$)-aryl, typically phenyl, which is substituted by one residue R(11); COOR(17); CON(R(18))$_2$; CONR(17)R(18); R(12); heteroalkyl, typically piperidine or imidazoline, which is unsubstituted or substituted by a residue R(23); ($C_3$-$C_7$)-cycloalkyl, which is unsubstituted or substituted with a residue R(23); or heteroaryl, which is unsubstituted or substituted by a residue R(22), typically by N(R(9))$_2$;

R(17) is hydrogen, ($C_1$-$C_4$)-alkyl, or ($C_6$-$C_{10}$)-aryl, preferably phenyl;

R(18) is hydrogen; ($C_1$-$C_4$)-alkyl, typically methyl or ethyl; ($C_6$-$C_{10}$)-aryl-($C_1$-$C_4$)-alkyl, typically phenylethyl, benzyl or naphthylmethyl; ($C_1$-$C_4$)-alkyl, which is substituted with OR(17); ($C_3$-$C_{10}$)-cycloalkyl-($C_1$-$C_4$)-alkyl, typically cyclohexylethyl, cyclohexylmethyl or adamantylmethyl; heteroaryl-($C_1$-$C_4$)-alkyl, typically thiophenylmethyl or pyridinylmethyl; or ($C_6$-$C_{10}$)-aryl-($C_1$-$C_4$)-alkyl, where alkyl or aryl in any of the foregoing are substituted with 1,2, or 3 identical or different residues R(24);

R(22) is methyl;

R(23) is oxo, -C(=NR(9))-R(39), -NH-S(O)(=NR(9))-($C_1$-$C_4$)-alkyl, -S(O)(=NR(9))-N(R(9))$_2$, or R(11);

R(24) is $CONH_2$; ($C_6$-$C_{10}$)-aryl, typically phenyl; Cl, CN, $OCH_3$, $CF_3$ or OR(17); and R(39) is hydrogen; ($C_6$-$C_{10}$)-aryl, typically phenyl; heteroaryl, typically pyridinyl; ($C_1$-$C_6$)-alkyl; or ($C_1$-$C_6$)-alkyl which is substituted by cyano.

Currently preferred compounds are compounds of the formula (I) in any stereoisomeric form, physiologically acceptable salts thereof, and mixtures of any of the foregoing in any ratio, wherein:

R(1) is cyclohexyl; pyridyl, preferably 3-pyridyl; naphthyl, preferably 2-naphthyl; 1-1,2,3,4-tetrahydro-naphthalene, 2-1,2,3,4,-tetrahydro-naphthalene, or phenyl; and any of the foregoing are unsubstituted or substituted by a residue R(8);

R(2) is hydrogen or ($C_1$-$C_4$)-alkyl, typically methyl;

R(3) benzyl, which is substituted in the aryl moiety by a residue R(11); or heteroaryl-($C_1$-$C_4$)-alkyl, typically isoquinolinmethyl, which is substituted in the heteroaryl moiety with a $NH_2$ group;

R(4) is hydrogen;

R(5) is hydrogen, cyclohexyl, butyl, cyclohexylmethyl, phenyl, phenylmethyl, or phenylethyl, wherein methyl or butyl in any of the foregoing is unsubstituted or substituted with a residue which is hydroxy, benzyloxy, $N(R(9))_2$ or hydroxycarbonyl;

R(6a) is hydrogen;

R(6b) is methyl or butyl, which are substituted by one or two identical or different residues R(15);

R(8) is methyl, $OCH_3$, $SO_2CH_3$, fluoro, chloro, bromo, $CF_3$ or $OCF_3$;

R(9) is R(10);

R(10) is hydrogen or benzyloxycarbonyl;

R(11) is R(12); methyl, which is substituted by R(12); or heteroaryl, which is substituted by ($C_1$-$C_4$)-alkyl;

R(12) is $N(R(9))_2$, -NR(10)-C(=NR(13))-NHR(10), -C(=NR(13))-NHR(10), or $CON(R(9))_2$;

R(13) is hydrogen or hydroxy;

R(15) is phenyl which is substituted by a residue R(11), piperidine or imidazoline which are unsubstituted or substituted by a residue R(23), COOR(17), CONR(17)R(18), $CON(R(18))_2$, R(12), or ($C_3$-$C_7$)-cycloalkyl, typically cyclohexyl, which is substituted with a residue R(23);

R(17) is hydrogen, phenyl, or ($C_1$-$C_4$)-alkyl;

R(18) is hydrogen; ($C_1$-$C_4$)-alkyl, typically methyl or ethyl; ($C_1$-$C_4$)-alkyl which is substituted with OR(17); ($C_6$-$C_{10}$)-aryl-($C_1$-$C_4$)-alkyl, typically phenylethyl, benzyl or naphthylmethyl; ($C_3$-$C_{10}$)-cycloalkyl-($C_1$-$C_4$)-alkyl, typically cyclohexylethyl, cyclohexylmethyl, or adamantylmethyl; heteroaryl-($C_1$-$C_4$)-alkyl, typically thiophenylmethyl or pyridinylmethyl; or ($C_6$-$C_{10}$)-aryl-($C_1$-$C_4$)-alkyl, where alkyl or aryl in any of the foregoing are substituted with one or two identical or different residues R(24);

R(23) is -C(=NR(9))-R(39) or R(11);

R(24) is phenyl, Cl, CN, $OCH_3$, $CF_3$, or OR(17); and

R(39) is ($C_6$-$C_{10}$)-aryl, typically phenyl; heteroaryl, typically pyridinyl; ($C_1$-$C_6$)-alkyl; or ($C_1$-$C_6$)-aklyl, which is substituted by cyano.

Also currently preferred compounds are compounds of the formula (I) in any stereoisomeric form, physiologically acceptable salts thereof, and mixtures of any of the foregoing in any ratio, wherein:

R(1) is cyclohexyl; pyridyl, typically 3-pyridyl; naphthyl, typically 2-naphthyl; or phenyl, which is unsubstituted or substituted by a residue R(8);

R(2) is hydrogen;

R(3) is benzyl which is substituted in the aryl moiety by a residue R(11);

R(4) is hydrogen;

R(5) is cyclohexyl, butyl, or phenyl;

R(6a) is hydrogen;

R(6b) is methyl which is substituted by a residue R(15); or butyl which is substituted by two identical or different residues R(15);

R(8) is methyl, $OCH_3$, $SO_2CH_3$, fluoro, chloro, bromo, or $CF_3$;

R(10) is hydrogen;

R(11) is R(12);

R(12) is -NR(10)-C(=NR(13))-NHR(10) or -C(=NR(13))-NHR(10);

R(13) is hydrogen;

R(15) is phenyl which is substituted by a residue R(11), piperidine which is substituted by a residue R(23); COOR(17), CONR(17)R(18), $CON(R(18))_2$, ($C_3$-$C_7$)-cycloalkyl, typically cyclohexyl, which is substituted by a residue R(23) or R(12);

R(17) is hydrogen or ($C_1$-$C_2$)-alkyl;

R(18) is hydrogen, phenylethyl, pyridinylmethyl, benzyl which is substituted in the alkyl part with phenyl, or benzyl which is substituted in the aryl part with $OCH_3$;

R(23) is R(11) or —C(=NH)—R(39); and

R(39) is methyl or ethyl.

Also currently preferred are compounds of the formula (I) in any stereoisomeric form, physiologically acceptable salts thereof, and mixtures of any of the foregoing in any ratio, wherein R(3) is benzyl which is substituted in the aryl part with an amidine group, and wherein the meaning of R(1), R(2), R(4), R(5), R(6a), and R(6b) is as mentioned above.

Also currently preferred are compounds of the formula (I), in any stereoisomeric form, physiologically acceptable salts thereof, and mixtures of any of the foregoing in any ratio, wherein R(6a) is hydrogen and R(6b) is phenylmethyl which is substituted in the phenyl part with an amidine group; or R(6b) is a group of the formula:

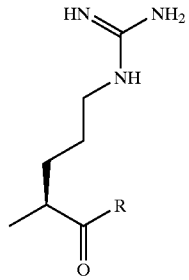

wherein R is amino, hydroxy, or ($C_1$-$C_4$)-alkoxy; or R(6b) is a group of the formula:

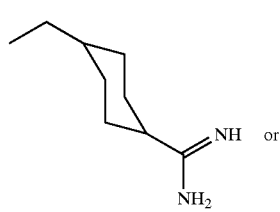

(IIIa)

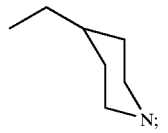

(IIIb)

wherein the nitrogen atom in (IIIb) is unsubstituted or substituted with an amidine group, C(=NH)—$CH_3$, or C(=NH)—$C_2H_5$, and wherein the meaning of R(1), R(2), R(3), R(4), and R(5) is as mentioned above.

Currently preferred are also compounds of the formula (I), in any stereoisomeric form, physiologically acceptable salts thereof, and mixtures of any of the foregoing in any ratio, wherein R(1) is cyclohexyl; pyridyl, preferably 3-pyridyl;

naphthyl, preferably 2-naphthyl; or phenyl, which is unsubstituted or substituted by a residue R(8), which is methyl, trifluoromethyl, methoxy, methylsulfonyl, fluoro, chloro, or bromo, and wherein the meaning of R(2), R(3), R(4), R(5), R(6a), and R(6b) is as mentioned above.

Those compounds are currently particular preferred if additionally R(2) and R(4) are hydrogen; R(3) is benzyl, which is substituted in the aryl part with an amidine group; R(5) is cyclohexyl, butyl, or phenyl; and where the meaning of R(6a) and R(6b) is as mentioned above.

Currently preferred are also compounds of the formula (I), in any stereoisomeric form, physiologically acceptable salts thereof, and mixtures of any of the foregoing in any ratio, wherein R(6a) is hydrogen and R(6b) is as mentioned above.

Compounds of formula (I) which are currently especially preferred are those wherein two or more residues in the formula (I) have the preferred meanings indicated above, all possible combinations of the preferred meanings being comprised.

Currently preferred compounds which may be mentioned are:

2-(S)-{2-[3-(4-Carbamimidoyl-phenyl)-2-cyclohexyl-propionylamino]-2-cyclohexyl-acetylamino}-5-guanidino-pentanoic acid phenethyl-amide, less polar diastereomeric mixture;

2-(S)-{2-(S)-[3-(4-Carbamimidoyl-phenyl)-2-cyclohexyl-propionylamino]-2-cyclohexyl-acetylamino}-5-guanidino-pentanoic acid amide, less polar diastereomer;

2-(S)-{2-(S)-[3-(4-Carbamimidoyl-phenyl)-2-cyclohexyl-propionylamino]-2-cyclohexyl-acetylamino}-5-guanidino-pentanoic acid ethyl ester, less polar diastereomer;

2-(S)-{2-(S)-[3-(4-Carbamimidoyl-phenyl)-2-cyclohexyl-propionylamino]-2-cyclohexyl-acetylamino}-5-guanidino-pentanoic acid, less polar diastereomer;

2-(S)-{2-(S)-[3-(4-Carbamimidoyl-phenyl)-2-(R,S)-pyridin-3-yl-propionylamino]-2-cydohexyl-acetylamino}-5-guanidino-pentanoic acid amide;

2-(S)-[3-(4-Carbamimidoyl-phenyl)-2-(R,S)-cyclohexyl-propionylamino]-hexanoic acid (1-(S)-carbamoyl-4-guanidino-butyl)-amide;

2-(S)-[3-(4-Carbamimidoyl-phenyl)-2-(R,S)-naphthalen-2-yl-propionylamino]-hexanoic acid (1-(S)-carbamoyl-4-guanidino-butyl)-amide;

2-(S)-[3-(4-Carbamimidoyl-phenyl)-2-(R,S)-methyl-2-phenyl-propionylamino]-hexanoic acid (1-(S)-carbamoyl-4-guanidino-butyl)-amide;

2-(S)-[3-(4-Carbamimidoyl-phenyl)-2-(R,S)-pyridin-3-yl-propionylamino]-hexanoic acid (1-(S)-carbamoyl-4-guanidino-butyl)-amide;

2-(S)-{2-(S)-[3-(4-Carbamimidoyl-phenyl)-2-(R,S)-pyridin-3-yl-propionyl-amino]-4-phenyl-butyrylamino}-5-guanidino-pentanoic acid amide;

3-(S)-[3-(4-Carbamimidoyl-phenyl)-2-(R,S)-pyridin-3-yl-propionyl-amino]-N-(1-(S)-carbamoyl-4-guanidino-butyl)-succinamic acid;

2-(S)-{2-(S)-[3-(4-Carbamimidoyl-phenyl)-2-(R,S)-pyridin-3-yl-propionyl-amino]-3-hydroxy-propionylamino}-5-guanidino-pentanoic acid amide;

2-(S)-{2-(S)-[3-(4-Carbamimidoyl-phenyl)-2-(R,S)-phenyl-propionylamino]-2-phenyl-acetylamino}-5-guanidino-pentanoic acid amide;

2-(S)-{2-(S)-[3-(4-Carbamimidoyl-phenyl)-2-(R,S)-cyclohexyl-propionyl-amino]-2-phenyl-acetylamino}-5-guanidino-pentanoic acid amide;

2-(S)-{2-(S)-[3-(4-Carbamimidoyl-phenyl)-2-(R,S)-naphthalen-2-yl-propionyl-amino]-2-phenyl-acetylamino}-5-guanidino-pentanoic acid amide;

2-(S)-{2-(S)-[3-(4-Carbamimidoyl-phenyl)-2-(R,S)-methyl-2-phenyl-propiony-amino]-2-phenyl-acetylamino}-5-guanidino-pentanoic acid amide;

2-(S)-{2-(S)-[3-(4-Carbamimidoyl-phenyl)-2-(R,S)-pyridin-3-yl-propionyl-amino]-2-phenyl-acetylamino}-5-guanidino-pentanoic acid amide;

2-(S)-{3-Benzyloxy-2-(S)-[3-(4-carbamimidoyl-phenyl)-2-(R,S)-methyl-2-phenyl-propionylamino]-propionylamino}-5-guanidino-pentanoic acid amide;

2-(S)-{3-Benzyloxy-2-(S)-[3-(4-carbamimidoyl-phenyl)-2-(R,S)-pyridin-3-yl-propionylamino]-propionylamino}-5-guanidino-pentanoic acid amide;

[5-(S)-[3-(4-Carbamimidoyl-phenyl)-2-(R,S)-pyridin-3-yl-propionylamino]-5-(1-(S)-carbamoyl-4-guanidino-butylcarbamoyl)-pentyl]-carbamic acid benzyl ester;

2-(S)-{2-(S)-[3-(4-Carbamimidoyl-phenyl)-2-(R,S)-naphthalen-2-yl-propionyl-amino) ]-2-cyclohexyl-acetylamino}-5-guanidino-pentanoic acid;

2-(S)-{2-(S)-[3-(4-Carbamimidoyl-phenyl)-2-phenyl-propionylamino]-2-cyclohexyl-acetylamino}-5-guanidino-pentanoic acid amide, less polar diastereomer;

2-(S)-{2-(S)-[3-(4-Carbamimidoyl-phenyl)-2-(R,S)-pyridin-3-yl-propionylamino]-3,3-dimethyl-butyrylamino}-5-guanidino-pentanoic acid amide;

2-(S)-{2-(S)-[3-(4-Carbamimidoyl-phenyl)-2-(R,S)-cyclo-hexyl-propionylamino]-2-cyclohexyl-acetylamino}-5-guanidino-pentanoic acid amide;

2-(S)-{2-(S)-[3-(4-Carbamimidoyl-phenyl)-2-(R,S)-naphthalen-2-yl-propionylamino]-2-cyclohexyl-acetylamino}-5-guanidino-pentanoic acid amide;

2-(S)-{(2-(S)-[3-(4-Carbamimidoyl-phenyl)-2-(R,S)-methyl-2-phenyl-propionylamino]-2-cyclohexyl-acetylamino}-5-guanidino-pentanoic acid amide;

2-(S)-{2-(S)-[3-(4-Carbamimidoyl-phenyl)-2-(R,S)-pyridin-3-yl-propionylamino]-3-cyclohexyl-propionylamino}-5-guanidino-pentanoic acid amide;

2-(S)-{2-(S)-[3-(4-Carbamimidoyl-phenyl)-2-(R,S)-pyridin-3-yl-propionylamino]-3-phenyl-propionylamino}-5-guanidino-pentanoic acid amide;

2-(S)-{2-(S)-[3-(4-Carbamimidoyl-phenyl)-2-cyclohexyl-propionylamino]-2-cyclohexyl-acetylamino}-5-guanidino-pentanoic acid amide, less polar diastereomer;

N-[(S)-(4-Carbamimidoyl-benzylcarbamoyl)-cyclohexyl-methyl]-3-(4-carbamimidoyl-phenyl)-2-cyclohexyl-propionamide, less polar diastereomer;

3-(4-Carbamimidoyl-phenyl)N-{(S)-[(1-carbamimidoyl-piperidin-4-ylmethyl)-carbamoyl]-cyclohexyl-methyl}-2-cyclohexyl-propionamide, less polar diastereomer;

2-(S)-{2-(S)-[2-(4-Bromo-phenyl)-3-(4-carbamimidoyl-phenyl)-propionylamino]-2-cyclohexyl-acetylamino}-5-guanidino-pentanoic acid amide, less polar diastereomer;

2-(S)-{2-(S)-[3-(4-Carbamimidoyl-phenyl)-2-m-tolyl-propionylamino]-2-cyclohexyl-acetylamino}-5-guanidino-pentanoic acid amide, more polar disteromer.

2-(S)-{2-(S)-[3-(4-Carbamimidoyl-phenyl)-2-(R,S)-m-tolyl-propionylamino]-2-cyclohexyl-acetylamino}-5-guanidino-pentanoic acid amide;

2-(S)-{2-(S)-[3-(4-Carbamimidoyl-phenyl)-2-(R,S)-(3-chloro-phenyl)-propionylamino]-2-cyclohexyl-acetylamino}-5-guanidino-pentanoic acid ethyl ester;

2-(S)-{2-(S)-[3-(4-Carbamimidoyl-phenyl)-2-(3-chloro-phenyl)-propionylamino]-2-cyclohexyl-acetylamino}-5-guanidino-pentanoic acid amide, less polar diastereomer;

2-(S)-{2-(S)-[3-(4-Carbamimidoyl-phenyl)-2-(R,S)(3-fluoro-phenyl)-propionylamino]-2-cyclohexyl-acetylamino}-5-guanidino-pentanoic acid ethyl ester;

2-(S)-{2-(S)-[2-(R,S)-(3-Bromo-phenyl)-3-(4-carbamimidoyl-phenyl)-propionylamino]-2-cyclohexyl-acetylamino}-5-guanidino-pentanoic acid ethyl ester;

2-(S)-{(2-(S)-[3-(4-Carbamoyl-phenyl)-2-phenyl-propionylamino]-2-cyclohexyl-acetylamino}-5-guanidino-pentanoic acid ethyl ester, less polar diastereomer;
2-(S)-{2-(S)-[3-(4-Carbamimidoyl-phenyl)-2-(3-fluoro-phenyl)-propionylamino]-2-cyclohexyl-acetylamino}-5-guanidino-pentanoic acid amide, less polar diastereomer;
2-(S)-{2-(S)-[3-(4-Carbamimidoyl-phenyl)-2-(3-fluoro-phenyl)-propionylamino]-2-cyclohexyl-acetylamino}-5-guanidino-pentanoic acid amide, more polar diastereomer;
2-(S)-{2-(S)-[2-(3-Bromo-phenyl)-3-(4-carbamimidoyl-phenyl)-propionylamino]-2-cyclohexyl-acetylamino}-5-guanidino-pentanoic acid amide, less polar diastereomer;
2-(S)-{2-(S)-[2-(3-Bromo-phenyl)-3-(4-carbamimidoyl-phenyl)-propionylamino]-2-cyclohexyl-acetylamino}-5-guanidino-pentanoic acid amide, more polar diastereomer;
2-(S)-{2-(S)-[3-(4-Carbamimidoyl-phenyl)-2-(R,S)-phenyl-propionylamino]-2-cyclohexyl-acetylamino}-5-guanidino-pentanoic acid amide;
3-(4-Carbamimidoyl-phenyl)-2-cyclohexyl-N-{(S)-cyclohexyl-{[1-(1-imino-ethyl)-piperidin-4-ylmethyl]-carbamoyl}-methyl)-propionamide, less polar diastereomer;
3-(4-Aminomethyl-phenyl)-N-[(S)(4-carbamimidoyl-benzyl-carbamoyl)-cyclohexyl-methyl]-2-(R,S)-cyclohexyl-propionamide;
2-(S)-{2-(S)-[3-(4-Carbamimidoyl-phenyl)-2-(R,S)-o-tolyl-propionylamino]-2-cyclohexyl-acetylamino}-5-guanidino-pentanoic acid amide;
2-(S)-{2-(S)-[3-(4-Carbamimidoyl-phenyl)-2-(R,S)-(1,2,3,4-tetrahydro-naphthalen-1-yl)-propionylamino]-2-cyclohexyl-acetylamino}-5-guanidino-pentanoic acid amide;
2-(S)-{2-(S)-[3-(4-Carbamimidoyl-phenyl)-2-(R,S)-(1,2,3,4-tetrahydro-naphthalen-2-yl)-propionylamino]-2-cyclohexyl-acetylamino}-5-guanidino-pentanoic acid amide;
N-[(S)-(4-Carbamimidoyl-benzylcarbamoyl)-cyclohexyl-methyl]-3-(4-carbamimidoyl-phenyl)-2-(3-fluoro-phenyl)-propionamide, less polar diastereomer;
2-(3-Bromo-phenyl)-N-[(S)-(4-carbamimidoyl-benzyl-carbamoyl)-cyclohexyl-methyl]-3-(4-carbamimidoyl-phenyl)-propionamide, more polar diastereomer;
2-(3-Bromo-phenyl)-N-[(S)-(4-carbamimidoyl-benzyl-carbamoyl)-cyclohexyl-methyl]-3-(4-carbamimidoyl-phenyl)-propionamide, less polar diastereomer;
N-[(S)-(4-Carbamimidoyl-benzylcarbamoyl)-cyclohexyl-methyl]-3-(4-carbamimidoyl-phenyl)-2-(R,S)-o-tolyl-propionamide;
2-(4-Bromo-phenyl)-N-[(S)(4-carbamimidoyl-benzyl-carbamoyl)-cyclohexyl-methyl]-3-(4-carbamimidoyl-phenyl)-propionamide, less polar diastereomer;
N-[(S)-(4-Carbamimidoyl-benzylcarbamoyl)-cyclohexyl-methyl]-3-(4-carbamimidoyl-phenyl)-2-(R,S)-(3-chloro-phenyl)-propionamide;
3-(4-Carbamimidoyl-phenyl)-N-{(S)-[(1-carbamimidoyl-piperidin-4-ylmethyl)-carbamoyl]-cyclohexyl-methyl}-2-m-tolyl-propionamide, less polar diastereomer;
3-(4-Carbamimidoyl-phenyl)-N-{(S)-[(1-carbamimidoyl-piperidin-4-ylmethyl}carbamoyl]-cyclohexyl-methyl}-2-(3-fluoro-phenyl)-propionamide, less polar diastereomer;
3-(4-Carbamimidoyl-phenyl)-N-{(S)-[(1-carbamimidoyl-piperidin-4-ylmethyl)-carbamoyl]-cyclohexyl-methyl}-2-(S)-o-tolyl-propionamide, more polar diastereomer;
3-(4-Carbamimidoyl-phenyl)-N-{(S)-[(1-carbamimidoyl-piperidin-4-ylmethyl)-carbamoyl]-cyclohexyl-methyl}-2-(R)-o-tolyl-propionamide, less polar diastereomer;
2-(3-Bromo-phenyl)-3-(4-carbamimidoyl-phenyl)-N-{(S)-[(1-carbamimidoyl-piperidin-4-ylmethyl)-carbamoyl]-cyclohexyl-methyl}-propionamide, less polar diastereomer;
3-(4-Amino-phenyl)-N-{(S)-[(1-carbamimidoyl-piperidin-4-ylmethyl)-carbamoyl]-cyclohexyl-methyl}-2-m-tolyl-propionamide, less polar diastereomer;
3-(4-Carbamimidoyl-phenyl)-N-{(S)-[(1-carbamimidoyl-piperidin-4-ylmethyl)-carbamoyl]-cyclohexyl-methyl}-2-naphthalen-2-yl-propionamide, less polar diastereomer;
3-(4-Carbamimidoyl-phenyl)-N-{(S)-[(1-carbamimidoyl-piperidin-4-ylmethylcarbamoyl]-cyclohexyl-methyl}-2-p-tolyl-propionamide, less polar diastereomer;
3-(4-Carbamimidoyl-phenyl)-N-{(S)-[(1-carbamimidoyl-piperidin-4-ylmethyl)-carbamoyl]-cyclohexyl-methyl}-2-(3-chloro-phenyl propionamide hydrochloric acid salt, less polar diastereomer;
2-(4-Bromo-phenyl)-3-(4-carbamimidoyl-phenyl)-N-{(S)-[(1-carbamimidoyl-piperidin-4-ylmethyl)-carbamoyl]-cyclohexyl-methyl}-propionamide hydrochloric acid salt, less polar diastereomer;
2-(S)-{2-[3-(4-Carbamimidoyl-phenyl)-2-(R,S)-cyclohexyl-propionylamino]-2-(S)-cyclohexyl-acetylamino}-5-guanidino-pentanoic acid isopropyl ester hydrochloric acid salt;
2-(S)-{2-[3-(4-Carbamimidoyl-phenyl)-2-cyclohexyl-propionylamino]-2-cyclohexyl-acetylamino}-5-guanidino-pentanoic acid benzyl-methyl-amide trifluoroacetic acid salt, less polar diastereomer;
2-(S)-{2-(R,S)-[3-(4-Carbamimidoyl-phenyl)-2-cyclohexyl-propionylamino)-2-(S)-cyclohexyl-acetylamino}-5-guanidino-pentanoic acid phenethyl-amide trifluoroacetic acid salt;
2-(S)-{2-[3-(4-Carbamimidoyl-phenyl)-2-cyclohexyl-propionylamino]-2-(S)-cyclohexyl-acetylamino}-5-guanidino-pentanoic acid butyl ester trifluoroacetic acid salt, less polar diastereomer;
2-(S)-{2-[3-(4-Carbamimidoyl-phenyl)-2-cyclohexyl-propionylamino]-2-(S)-cyclohexyl-acetylamino}-5-guanidino-pentanoic acid propyl ester, less polar diastereomer;
2-(S)-{2-[3-(4-Carbamimidoyl-phenyl)-2-cyclohexyl-propionylamino]-2-cyclohexyl-acetylamino}-5-guanidino-pentanoic acid (thiophen-2-ylmethyl)-amide trifluoroacetic acid salt;
2-(S)-{2-[3-(4-Carbamimidoyl-phenyl)-2-cyclohexyl-propionylamino]-2-cyclohexyl-acetylamino}-5-guanidino-pentanoic acid (pyridin-4-ylmethyl)-amide trifluoroacetic acid salt;
2-(S)-{(2-[3-(4-Carbamimidoyl-phenyl)-2-cyclohexyl-propionylamino]-2-cyclohexyl-acetylamino}-5-guanidino-pentanoic acid benzhydryl-amide trifluoroacetic acid salt;
2-(S)-{2-[3-(4-Carbamimidoyl-phenyl)-2-cyclohexyl-propionylamino]-2-cyclohexyl-acetylamino}-5-guanidino-pentanoic acid benzylamide trifluoroacetic acid salt;
2-(S) {2-[3-(4-Carbamimidoyl-phenyl)-2-cyclohexyl-propionylamino]-2-cyclohexyl-acetylamino}-5-guanidino-pentanoic acid 4-chloro-benzylamide trifluoroacetic acid salt;
2-(S)-{2-[3-(4-Carbamimidoyl-phenyl)-2-cyclohexyl-propionylamino]-2-cyclohexyl-acetylamino}-5-guanidino-pentanoic acid 4-methoxy-benzylamide trifluoroacetic acid salt;
3-(4-Carbamimidoyl-phenyl)-N-{(S)-[(1-carbamimidoyl-piperidin-4-ylmethyl)-carbamoyl]-cyclohexyl-methyl}-2-(2-fluoro-phenyl)-propionamide trifluoroacetic acid salt;

3-(4-Carbamimidoyl-phenyl)-N-{(S)-[(1-carbamimidoyl-piperidin-4-ylmethyl)-carbamoyl]-cyclohexyl-methyl}-2-(4-chloro-phenyl)-propionamide trifluoroacetic acid salt, less polar diastereomer;

2-(3-Bromo-phenyl)-N-{(S)-[(4-carbamimidoyl-cyclohexylmethyl)-carbamoyl]-cyclohexyl-methyl}-3-(4-carbamimidoyl-phenyl)-propionamide trifluoroacetic acid salt, less polar diastereomer;

3-(4-Carbamimidoyl-phenyl)-N-{(S)-[(1-carbamimidoyl-piperidin-4-ylmethyl)-carbamoyl]-cyclohexyl-methyl}-2-phenyl-propionamide trifluoroacetic acid salt, less polar diastereomer;

2-(3-Bromo-phenyl)-3-(4-carbamimidoyl-phenyl)-N-((S)-cyclohexyl-{[1-imino-ethyl)-piperidin-4-ylmethyl]-carbamoyl}-methyl)-propionamide trifluoroacetic acid salt, less polar diastereomer;

3-(4-Carbamimidoyl-phenyl)-N-{(S)-[(1-carbamimidoyl-piperidin-4-ylmethyl)-carbamoyl]-cyclohexyl-methyl}-2-(3-trifluoromethyl-phenyl)-propionamide trifluoroacetic acid salt, less polar diastereomer;

3-(4-Carbamimidoyl-phenyl)-N-{(S)-[(1-carbamimidoyl-piperidin-4-ylmethyl)-carbamoyl]-cyclohexyl-methyl}-2-(2-chloro-phenyl)-propionamide trifluoroacetic acid salt, less polar diastereomer; and 3-(4-Carbamimidoyl-phenyl)-N-{(S)((1-carbamimidoyl-piperidin-4-ylmethyl)-carbamoyl]-cyclohexyl-methyl}-2-(4-trifluoromethyl-phenyl)-propionamide trifluoroacetic acid salt, less polar diastereomer and/or a physiologically acceptable salt.

The compounds of formula (I) can be prepared by utilizing procedures and techniques well known and appreciated by one of ordinary skill in the art. Starting materials or building blocks for use in the general synthetic procedures that can be applied in the preparation of the compounds of formula (I) are readily available to one of ordinary skill in the art. In many cases they are commercially available or have been described in the literature. Otherwise they can be prepared from readily available precursor compounds analogously to procedures described in this application.

Compounds of the formula (I) can be prepared, for example, by method A as described in scheme 2, where the residues R(1), R(2), R(3), R(4), R(5), R(6a), and R(6b) are defined as indicated above.

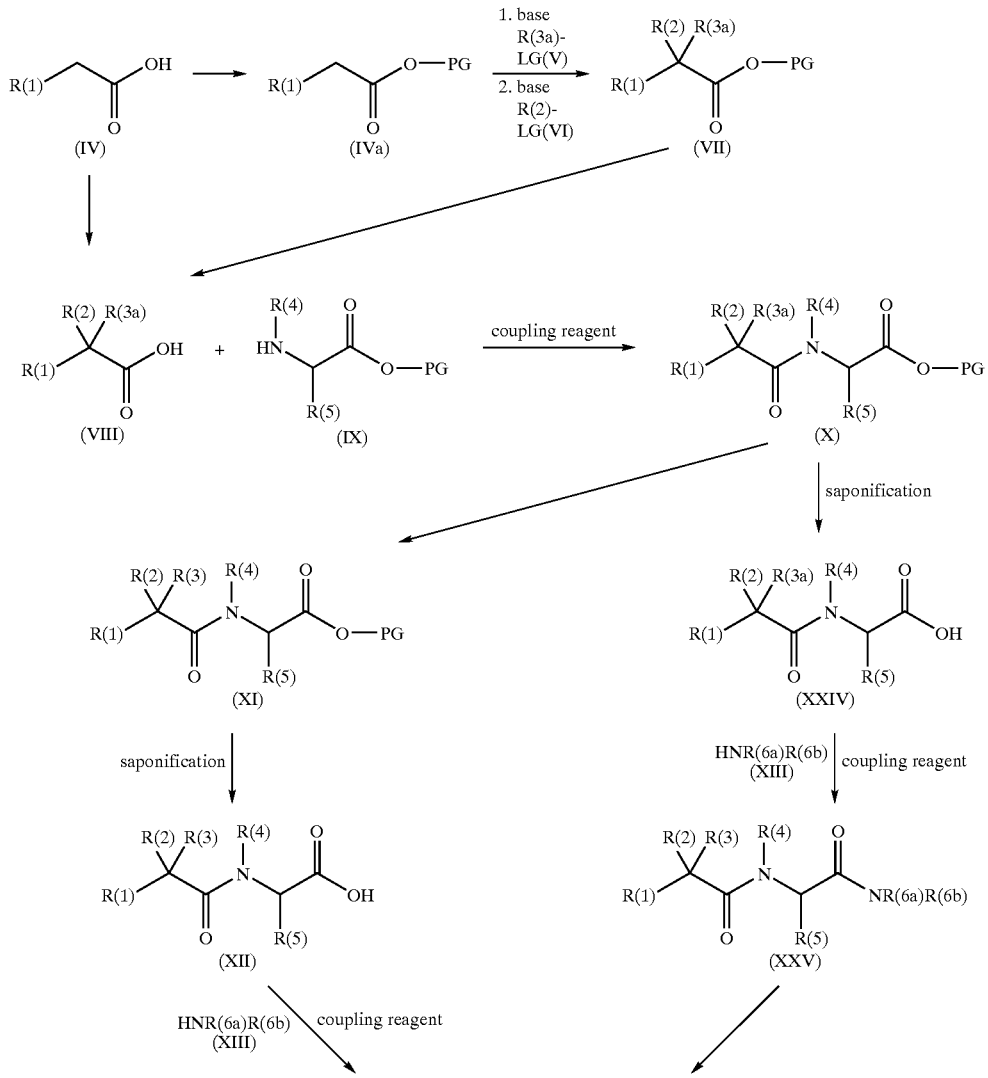

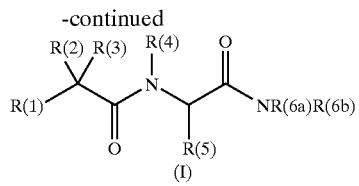

(I)

Various alkylated acetic acids IV can be alkylated one (in case of R(2) is hydrogen) or two (in case of R(2) is alkyl) times after protection of the carboxylic function by an easily cleavable protecting group by standard conditions using base and the alkylating agents V or V and VI, where R(3a) is $(C_8-C_{10})$-aryl-$(C_1-C_3)$-alkyl, which is substituted in the aryl or alkyl moiety by a residue R(29); heteroaryl-$(C_1-C_4)$-alkyl, $(C_3-C_7)$-cycloalkyl-$(C_1-C_4)$-alkyl; heteroaryl-$(C_1-C_4)$-alkyl or $(C_3-C_7)$-cycloalkyl-$(C_1-C_4)$alkyl, which are substituted in the heteroaryl, cycloalkyl or alkyl part by one, two or three residues R(29); or heteroalkyl-$(C_1-C_4)$-alkyl, which is unsubstituted or substituted by a residue R(23), wherein R(23) is as defined above;

R(29) is R(30) or $(C_1-C_4)$-alkyl, which is unsubstituted or substituted by R(30);

R(30) is $N(R(31))_2$, $CON(R9))_2$, $NO_2$, chloro, or CN, and where residues R(30), if present more than one time in the molecule, are independent of each other and can be identical or different;

R(31) is $(C_1-C_6)$-alkyl, $(C_6-C_{10})$-alkyl, $(C_1-C_6)$-alkylcarbonyl, or $(C_1-C_6)$-alkoxycarbonyl, and where residues R(31), if present more than one time in the molecule, are independent of each other and can be identical or different;

and wherein LG is a leaving group such as a halogen, or a substituted hydroxy group such as tosyloxy or mesyloxy; thereby resulting in a compound of formula VII.

The trisubstituted acetic acid VII can be deprotected by standard methods to give compounds of the formula VIII.

Another possibility for the first alkylation is the condensation of IV with the corresponding aldehyde Vb

(Vb)

wherein R(3b) is $(C_6-C_{10})$-aryl or $(C_8-C_{10})$-alkyl, where the aryl moiety is substituted by R(30); heteroaryl-$(C_1-C_3)$-alkyl, $(C_3-C_7)$-cycloalkyl-$(C_1-C_3)$-alkyl; heteroaryl-$(C_1-C_3)$-alkyl or $(C_3-C_7)$-cycloalkyl-$(C_1-C_3)$-alkyl, which are substituted in the heteroaryl, cycloalkyl or alkyl part by 1, 2, or 3 residues R(29); or heteroaryl-$(C_1-C_3)$ alkyl, which is unsubstituted or substituted by a residue R(23); in a suitable solvent, for example acetic acid anhydride (Tetrahedron Left. 1990, 31, 5307-10) and following hydrogenation of the double bond by standard methods.

Compounds of the formulae V, Vb or Vl are either commercially available or can be prepared by standard procedures which are known to one skilled in the art.

Coupling of VIII and IX, wherein PG is an easily cleavable protecting group for carboxylic functions (for example $(C_1-C_4)$-alkyl, benzyl, or 4-methoxybenzyl) to yield X can be carried out by common coupling reagents used in peptide synthesis. Such coupling reagents are, for example, carbodiimides such as dicyclohexylcarbodiimide (DCCl) or diisopropylcarbodiimide (DICI), carbonyldiazoles such as carbonyldiimidazole and similar reagents, propylphosphonic anhydride, O-((cyano-(ethoxycarbonyl)-methylen)amino)-N,N,N',N'-tetramethyluronium tetrafluoroborate (TOTU), N-[(dimethylamino)-1H-1,2,3-triazolo[4,5-b]pyridin-1 ylmethylene]-N-methylmethanaminium hexafluorophosphate N-oxide (HATU), and many others.

Compounds of the formula IX are either commercially available or can be prepared by standard procedures which are known to one skilled in the art. Conversion of R(3a) to R(3) (X→XI, or XXV →I), if necessary, can be made by introduction of a guanidino group or an amidino group as described below, or by reduction of a nitro group by hydrogenation with, for example, Raney-Nickel, palladium/charcoal, or other catalysts in the presence of hydrogen, by replacement of a chloro atom by an amino group by reaction of compounds which contain an chloroisochinoline moiety with ammonium acetate in phenol or by other methods well known in the literature, by reaction of a hydroxyamidine moiety with alkyl-chloroformiate and dehydrogenation with base, for example sodiumcarbonate in water to give the 4H-[1,2,4]oxadiazol-5-one residue, by reaction of a hydroxyamidine moiety with acetone under acidic conditions to yield the 5,5-dimethyl-4,5-dihydro-[1,2,4] oxadiazole moiety, or by reaction of an amidine moiety with alkyl chloro formiate to yield the alkyloxycarbonyl protected amidino group.

A guanidino function can be introduced by conversion of an amino function which, for example, may be obtained by reduction of a nitro function or a cyano function, using the following reagents:

1. O-Methylisourea (S. Weiss and H. Krommer, Chemiker-Zeitung 98 (1974), 617–618;
2. S-Methylisothiourea (R. F. Bome, M. L. Forrester and I. W. Waters, J. Med. Chem. 20 (1977), 771–776;
3. Nitro-S-methylisothiourea (L. S. Hafner and R. E. Evans, J. Org. Chem. 24 (1959) 1157;
4. Formamidinosulfonic acid (K. Kim, Y.-T. Lin and H. S. Mosher, Tetra. Lett. 29 (1988), 3183–3186;
5. 3,5-Dimethyl-1-pyrazolylformamidinium nitrate (F. L. Scott, D. G. O'Donovan and J. Reilly, J. Amer, Chem. Soc, 75 (1953), 4053–4054;
6. N,N'-Di-tert-butyloxycarbonyl-S-methylisothiourea (R. J. Bergeron and J. S. McManis, J. Org. Chem. 52 (1987), 1700–1703; and
7. N-Alkoxycarbonyl-, N,N'-dialkoxycarbonyl-, N-alkylcarbonyl- and N,N'-dialkylcarbonyl-S-methylisothiourea (H. Wollweber, H. Kölling, E. Niemers, A.

Widdig, P. Andrews, H.-P. Schulz and H. Thomas, Arzneim. Forsch./Drug Res. 34 (1984), 531–542).

Amidines can be prepared from the corresponding cyano compounds by addition of alcohols, for example methanol or ethanol, in acidic anhydrous medium, for example dioxane, methanol, or ethanol, and subsequent aminolysis, for example treatment with ammonia in alcohols such as, for example, isopropanol, methanol, or ethanol. G. Wagner, P.

Richter and Ch. Garbs, Pharmazie 29 (1974), 12–55. Further methods of preparing amidines are the addition of hydrogen sulfide to the cyano group, followed by alkylation, for example methylation, of the resulting thioamide and subsequent reaction with ammonia (GDR Patent No. 235 866), and the addition of hydroxylamine (which may be obtained from a hydroxylammonium salt with a base) to the cyano group followed by conversion of the amidoxime to the amidine, for example by catalytic hydrogenation.

Saponification of the ester of compounds of the formula XI to give compounds of the formula XII can be carried out by standard methods. Coupling of XII and XIII to give compounds of the formula (I) can be carried out with coupling reagents as described above. Compounds of the formula XIII are either commercially available or can be prepared by standard procedures which are known to one skilled in the art.

Another way to come to compounds of the formula (I) is the saponification by standard methods of the ester group of compounds of the formula X to give compounds of the formula XXIV. Coupling of XXIV with XX to give compounds of the formula XXV and conversion of the residue R(3a) to R(3) can be done by procedures described above.

Compounds of the formula (I) can also be obtained by method B as drawn in schemes 3 and 4.

Scheme 3

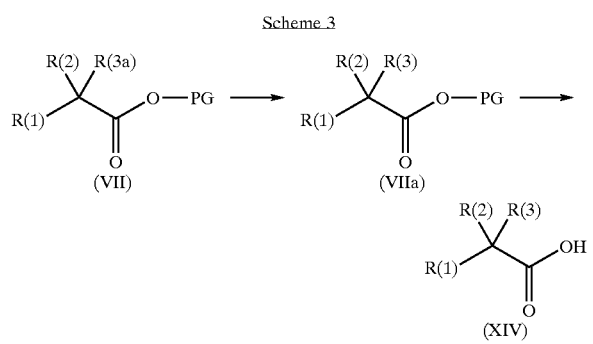

After protection of the carboxyl function with an easily cleavable protection group (such as, for example, $(C_1-C_4)$-alkyl, benzyl, or 4-methoxybenzyl) by standard methods, the residue R(3a) in compounds of the formula VII can be transformed to the residue R(3) and deprotected as outlined above to give compounds of the formula XIV.

Scheme 4

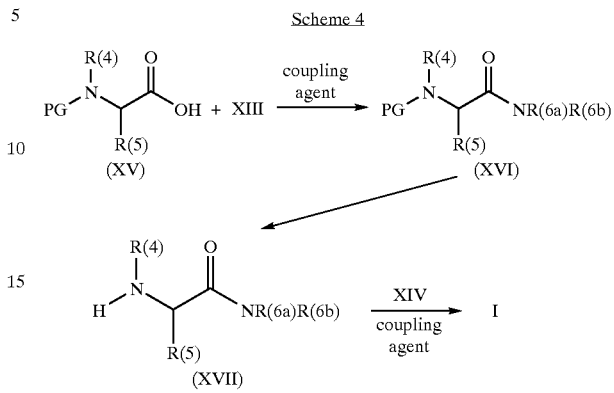

The protected amino acid XV (wherein PG is a suitable amino protection group, for example Fmoc, benzyloxycarbonyl (Z), or Boc, typically Fmoc) can be coupled by standard methods as described above with compounds of the formula XIII to give compounds of the formula XVI. Compounds of the formula XVI can be deprotected by standard methods, for example, by standard methods for Fmoc-deprotection (L. A. Carpino et al., J. Org. Chem. 1988, 53, 6139–44) to give compounds of the formula XVII. Compounds of the formula XVII can be coupled with compounds of the formula XIV by standard methods to give compounds of the formula (I).

Compounds of the formula XV are either commercially available or can be prepared by standard procedures which are known to one skilled in the art.

Compounds of the formula (I) can also be obtained by solid phase peptide synthesis (method C) as drawn in scheme 5. Such methods are described, for example, by Steward and Young (Solid Phase Peptide Synthesis, Freeman and Co., San Francisco, 1969), which is incorporated herein by reference.

Scheme 5

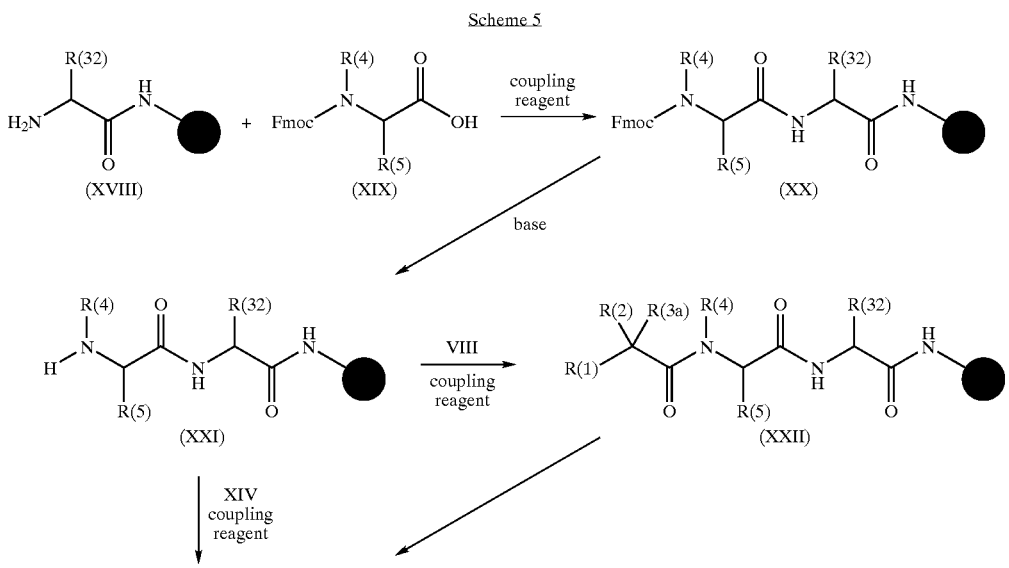

-continued

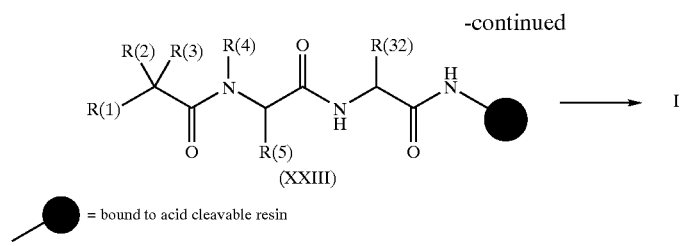

(XXIII)

● = bound to acid cleavable resin

Where solid phase synthesis methods are employed, the chemical composition of a compound can be manipulated while the nascent peptide is attached to the resin or after the peptide has been cleaved from the resin to obtain, for example, an N-terminal derivative. Similar modifications can also be made to a carboxy group of a compound, including a C-terminus carboxy group, which, for example, can be amidated. One skilled in the art can also synthesize a compound of the invention using solution phase organic chemistry.

Using this method (C) (scheme 5) compounds of the formula XVIII, where an amino acid is coupled to a suitable carrier, which are, for instance, Wang, Trityl, or Rink resin or other acid cleavable resins, which are known to a person skilled in the art, and where R(32) is hydrogen; $(C_1-C_8)$-alkyl, which can be substituted one or two times by R(33); $(C_6-C_{14})$-aryl, or heteroaryl, which both are unsubstituted or substituted 1, 2, 3, 4, or 5 times by identical or different residues R(34);

R(33) is $(C_6-C_{10})$-aryl, heteroaryl, O-heteroaryl, S-heteroaryl, $(C_3-C_7)$cycloalkyl, heteroalkyl, COOR(17), CON(R(18))$_2$, oxo, OR(17), R(35), or the residue of the α-C-atom of a natural amino acid, and where residues R(33), if present more than one time in the molecule, are independent of each other and can be identical or different;

R(35) is N(R(36))$_2$, NR(38)-C(=NR(37))—NHR(38), or C(=NR(37))—NHR(38);

R(36) is R(38) or $(C_6-C_{10})$-aryl-$(C_1-C_4)$-alkyl, and where residues R(36) if present more than one time in the molecule, are independent of each other and can be identical or different;

R(37) is R(38), cyano, hydroxy, $(C_1-C_6)$-alkoxy; $(C_6-C_{14})$-aryl-$(C_1-C_6)$-alkoxy, which can also be substituted in the aryl moiety; or amino, and where residues R(37), if present more than one time in the molecule, are independent of each other and can be identical or different;

R(36) is hydrogen, $(C_1-C_6)$-alkylcarbonyl, or $(C_1-C_6)$-alkoxycarbonyl;

R(34) is $(C_1-C_6)$-alkyl, $(C_6-C_{10})$-aryl, heteroaryl, heteroalkyl, COOR(17), CON(R(18))$_2$, OH, or R(35);

can be coupled with an Fmoc-protected amino acid XIX using standard techniques. Compounds of the formulae Will and XIX are either commercially available or can be prepared by standard procedures which are known to one skilled in the art. The resulting dipeptide XX can be deprotected using base, for example, a solution of 20–50% of piperidin in dimethylformamide to obtain compounds of the formula XXI with a primary or secondary amino group, which can be coupled to the building blocks VIII or XIV prepared using method A or B. Conversion of the residue R(3a) of the resulting compound XXII to the residue R(3) can be done as described above. Compounds of the formula (I) can be obtained by cleaving compounds of the formula XXIII under acidic conditions for example trifluoroacetic acid/water in different concentrations depending on the used resin varying from 1% to 95% of trifluoroacetic acid.

These synthesized compounds can be purified using well known methods such as reverse phase-high performance liquid chromatography (RP-HPLC) or other methods of separation based, for example, on the size, charge, or hydrophobicity of the compound. Similarly, well known methods such as amino acid sequence analysis or mass spectrometry (MS or HPLC/ESMS) can be used for characterizing the structure of a compound of the invention (see Example 9).

Thus, the present invention also covers a process for the preparation of a compound of formula (I), which comprises (i)

(a1) protecting the carboxylic function of a compound of the formula IV:

(IV)

and reacting such a protected compound of the formula IVa:

(IVa)

with a compound of formula V:

(V)

wherein

R(3a) is $(C_6-C_{10})$-aryl-$(C_1-C_4)$-alkyl, which is substituted in the aryl or alkyl moiety by a residue R(29); heteroaryl-$(C_1-C_4)$-alkyl, $(C_3-C_7)$-cycloalkyl-$(C_1-C_4)$-alkyl; heteroaryl-$(C_1-C_4)$-alkyl or $(C_3-C_7)$-cycloalkyl-$(C_1-C_4)$-alkyl, which are substituted in the heteroaryl, cycloalkyl or alkyl part by 1, 2, or 3 residues R(29); or heteroalkyl-$(C_1-C_4)$-alkyl, which is unsubstituted or substituted by a residue R(23), wherein R(23) is as defined above;

R(29) is R(30) or $(C_1-C_4)$-alkyl, which is unsubstituted or substituted by R(30);

R(30) is N(R(31))$_2$, CON(R(9))$_2$, NO$_2$, chloro, or CN, and where residues R(30), if present more than one time in the molecule, are independent of each other and can be identical or different;

R(31) is $(C_1-C_6)$-alkyl, $(C_6-C_{10})$-aryl-$(C_1-C_4)$-alkyl, $(C_1-C_6)$-alkylcarbonyl, or $(C_1-C_6)$-alkoxycarbonyl, and where residues R(31), if present more than one time in the molecule, are independent of each other and can be identical or different;

and wherein LG is a leaving group like a halogen or a substituted hydroxy group like tosyloxy or mesyloxy; or additionally with a compound of formula VI:

R(2)-LG  (VI)

wherein R(2) is (C$_1$–C$_4$)-alkyl and LG is as defined above, in the presence of a base to give a compound of formula VII:

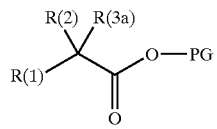 (VII)

and deprotecting a compound of the formula VII to give a compound of the formula VIII:

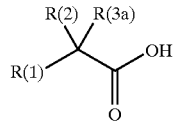 (VIII)

or coupling a compound of the formula IV or IVa to a compound of the formula Vb:

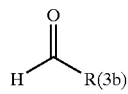 (Vb)

wherein R(3b) is (C$_6$–C$_{10}$)-aryl or (C$_6$–C$_{10}$)-aryl-(C$_1$–C$_3$)-alkyl, where the aryl moiety is substituted by R(30); heteroaryl-(C$_1$–C$_3$)-alkyl, (C$_3$–C$_7$)-cycloalkyl-(C$_1$–C$_3$)-alkyl; heteroaryl-(C$_1$–C$_3$)-alkyl, or (C$_3$–C$_7$)-cycloalkyl-(C$_1$–C$_3$)-alkyl, which are substituted in the heteroaryl, cycloalky, or alkyl part by 1, 2, or 3 residues R(29); or hetemalkyl-(C$_1$–C$_3$)-alkyl, which is unsubstituted or substituted by a residue R(23); wherein R(23) is as defined above; R(29) is R(30) or (C$_1$–C$_4$)-alkyl, which is unsubstituted or substituted by R(30);

R(30) is N(R(31))$_2$, CON(R(9))$_2$, NO$_2$, chloro, or CN, and where residues R(30), if present more than one time in the molecule, are independent of each other and can be identical or different;

R(31) is (C$_1$-C$_6$)-alkyl, (C$_6$-C$_{10}$)-aryl-(C$_1$-C$_4$)-alkyl, (C$_1$-C$_6$)-alkylcarbonyl, or (C$_1$-C$_6$)-alkoxycarbonyl, and where residues R(31), if present more than one time in the molecule, are independent of each other and can be identical or different;

in an appropriate solvent, for example acetic acid anhydride, and following hydrogenation of the double bond by standard methods to yield a compound of the formula VIII where R(2) is hydrogen and R(3a) is CH$_2$—R(3b) as defined above;

(a2) coupling a compound of the formula VIII with a compound of formula IX:

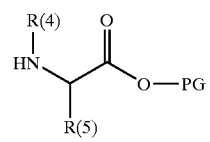 (IX)

wherein PG is an easily cleavable protecting group, in the presence of a suitable coupling reagent to give a compound of formula X:

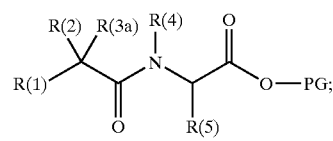 (X)

(a3) optionally converting a compound of the formula X into a compound of the formula XI, or a compound of formula XXV into a compound of formula (I)

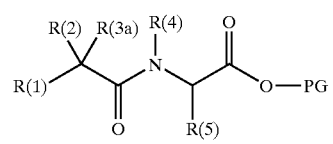 (XI)

wherein R(3) is as defined above; for instance by introducing an amidino or guanidino group, by reduction of a nitro group, by replacement of a chloro atom by an amino group, by reaction of compounds which contain a chloroisochinoline moiety with ammonium acetate in phenol, by reaction of a hydroxyamidine moiety with alkyl-chloro-formiate and dehydrogenation with base, for example sodium carbonate in water, to give the 4H-[1,2,4]oxadiazol-5-one residue, by reaction of a hydroxyamidine moiety with acetone under acidic conditions to yield the 5,5-dimethyl-4,5-dihydro-[1,2,4]oxadiazole moiety, or by reaction of an amidine moiety with alkyl chloro formiate to yield the alkyloxycarbonyl protected amidino group;

(a4) saponification of a compound of the formula XI or X and coupling the resulting compound according to coupling step (a2) with a compound of the formula XIII:

HNR(6a)R(6b)  (XIII)

wherein R(6a) and R(6b) is as described above thereby resulting in a compound of formula (I) or XXV:

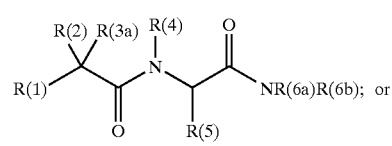 (XXV)

(b) starting from a compound of the formula VII (b1) optionally converting a compound of the formula VII into a compound of the formula VIIa by the procedure described in (a3)

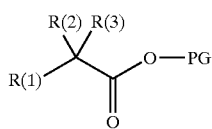

(VIIa)

and deprotecting the compound of the formula VIIa to give a compound of the formula XIV:

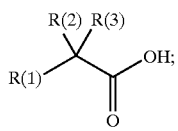

(XIV)

(b2) coupling a compound of the formula XIV according to coupling step (a2) with a compound of the formula XVII:

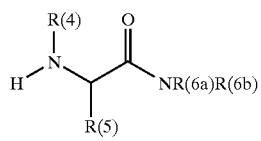

(XVII)

to give a compound of the formula (I); or
(ii)
(a) coupling a compound of the formula XVIII:

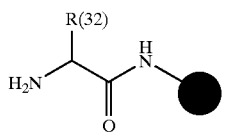

(XVIII)

which is bound to a suitable carrier, for example an acid cleavable resin, and wherein R(32) is hydrogen; $(C_1-C_8)$-alkyl, which can be substituted one or two times by R(33); $(C_6-C_{14})$-aryl, or heteroaryl, which both are unsubstituted or substituted 1, 2, 3, 4, or 5 times by identical or different residues R(34);

R(33) is $(C_6-C_{10})$-aryl, heteroaryl, O-heteroaryl, S-heteroaryl, $(C_3-C_7)$-cycloalkyl, heteroalkyl, COOR (17), CON(R(18))$_2$, oxo, OR(17), R(35), or the residue of the α-C-atom of a natural amino acid, and where residues R(33), if present more than one time in the molecule, are independent of each other and can be identical or different;

R(35) is N(R(36))$_2$, NR(38)—C(=NR(37))—NHR (38), or C(=NR(37))—NHR(38);

R(36) is R(38) or $(C_6-C_{10})$-aryl-$(C_1-C_4)$-alkyl, and where residues R(36), if present more than one time in the molecule, are independent of each other and can be identical or different;

R(37) is R(38), cyano, hydroxy, $(C_1-C_6)$-alkoxy; $(C_6-C_{14})$-aryl-$(C_1-C_6)$-alkoxy, which can also be substituted in the aryl moiety; or amino, and where residues R(37), if present more than one time in the molecule, are independent of each other and can be identical or different;

R(38) is hydrogen, $(C_1-C_6)$-alkyl, $(C_1-C_6)$-alkylcarbonyl, or $(C_1-C_6)$-alkoxycarbonyl;

R(34) is $(C_1-C_6)$-alkyl, $(C_6-C_{10})$-aryl, heteroaryl, heteroalkyl, COOR(17), CON(R(18))$_2$, OH, or R(35);

with a compound of the formula XIX:

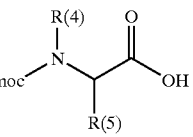

(XIX)

wherein R(4) and R(5) are as defined above to give a compound of the formula XX:

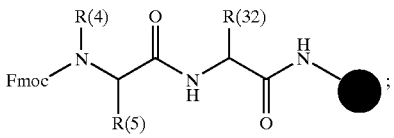

(XX)

(b) and after deprotecting a compound of the formula XX with a base, coupling the deprotected compound XX to a compound of the formula VIII to give a compound of the formula XXII:

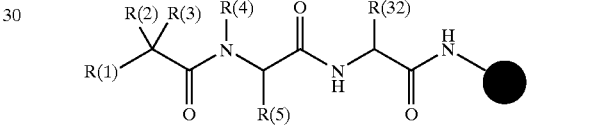

(XXII)

or coupling the deprotected compound XX to a compound of the formula XIV to give a compound of the formula XXIII:

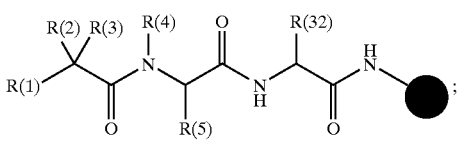

(XXIII)

(c) optionally converting a compound of the formula XXII to a compound of the formula XXIII (i.e. transforming the residue R(3a) to a residue R(3) by introducing an amidino or guanidino group, or by reduction of a nitro group);

and (d) cleaving a compound of the formula XII (or XIII) off the resin, and converting the residue R(3a) ro R(3), if necessary, thereby producing a compound of the formula (I).

As is demonstrated in the pharmacological tests described below, the compounds of formula (I) inhibit factor Xa activity. They can therefore advantageously be used as pharmaceuticals, especially when it is desired to reduce factor Xa activity or to produce effects that can be achieved by inhibiting factor Xa activity in a system, such as influencing coagulation or inhibiting blood clotting. Thus, the present invention also relates to the compounds of formula (I) for use as pharmaceuticals as well as for the production of medicaments, especially of medicaments for treatment or prophylaxis of the conditions and diseases mentioned below and above. Further, the present invention provides a method of specifically inhibiting factor Xa activity by contacting factor Xa with a compound of formula (I). More specifically, an effective amount of a compound of the invention inhibits factor Xa catalytic activity either directly, within the prothrombinase complex or as a soluble subunit, or indirectly, by inhibiting the assembly of factor Xa into the prothrombinase complex. A typical embodiment of the invention comprises such compounds of the formula (I) which can inhibit factor Xa activity with a $K_i \leq 100 \mu M$ and, preferably, with a $K_i \leq 1 \mu M$.

As used herein, the term "factor Xa activity" refers to the ability of factor Xa, by itself or in the assembly of subunits known as the prothrombinase complex, to catalyze the conversion of prothrombin to thrombin. When used in reference to factor Xa activity, the term "inhibition" includes both the direct and indirect inhibition of factor Xa activity. Direct inhibition of factor Xa activity can be accomplished, for example, for example, by the binding of a compound of formula (I) to factor Xa or to prothrombinase so as to prevent the binding of prothrombin to the prothrombinase complex active site. Indirect inhibition of factor Xa activity can be accomplished, for example, by the binding of a compound of the invention to soluble factor Xa so as to prevent its assembly into the prothrombinase complex. As used herein, the term "specific", when used in reference to the inhibition of factor Xa activity, means that a compound of formula (I) can inhibit factor Xa activity without substantially inhibiting the activity of other specified proteases, including thrombin (using the same concentration of the inhibitor). Such proteases are involved in the blood coagulation and fibrinolysis cascade.

Inhibition of factor Xa activity or the production of effects achieved by such an inhibition can take place in vivo, i. e. in an individual. As used herein, the term "individual" means a vertebrate, including a mammal such as, for example a mouse, a rat, a rabbit, a dog, a pig, a monkey, and especially a human, in which factor Xa is involved in the clotting cascade. It can also take place outside the body of an individual, for example, in an extracorporeal circulation or in the treatment of blood samples from an individual, and generally in vitro. In vitro uses of the compounds of formula (I) are, for example, the use as a biochemical tool in scientific or analytical investigations or the use for in vitro diagnoses. A compound of formula (I) can advantageously be used as an anticoagulant, which can be contacted with a blood sample to prevent coagulation. For example, an effective amount of a compound of formula (I) can be contacted with a freshly drawn blood sample to prevent coagulation of the blood sample.

As used herein, the term "effective amount" when used in this connection means an amount of a compound of formula (I) that inhibits factor Xa activity to the desired extent. The skilled artisan would recognize that an effective amount of a compound of the invention can be determined using the methods disclosed herein or otherwise known in the art.

In view of the disclosed utility of the compounds of formula (I), the skilled artisan also would recognize that an agent such as heparin can be replaced with a compound of the invention. Such a use of a compound of formula (I) can result, for example, in a cost saving as compared to other anticoagulants.

In a further embodiment, the present invention provides a method of inhibiting factor Xa in a patient in need thereof, comprising administering to said patient an effective factor Xa inhibitory amount of a compound of formula (I). As used herein, the term "patient" refers especially to a warm-blooded animal including a mammal and particularly a human. A patient is in need of treatment to inhibit factor Xa when the patient is suffering from a disease state that can be beneficially influenced by inhibiting factor Xa activity or that is expected by the clinician to be beneficially influenced by inhibiting factor Xa acitivity.

The identification of those patients who are in need of treatment to inhibit factor Xa is well within the ability and knowledge of one skilled in the art. A clinician skilled in the art can readily identify, by the use of clinical tests, physical examination and medical/family history, those patients who are in need of such a treatment.

Since a compound of formula (I) can inhibit factor Xa activity, such a compound can be used for reducing or inhibiting blood clotting in an individual. Thus, the present invention further provides a method of reducing or inhibiting the formation of blood clots in an individual, especially in a patient in need thereof, by administering a therapeutically effective amount of a compound of formula (I).

A therapeutically effective amount relating to the production in an individual of an effect like inhibition or reduction of blood clotting, or an effective factor Xa inhibitory amount of a compound of formula (I) means the amount or the dose of a compound of formula (I) that has to be administered to an individual in order to achieve or to maintain the desired effect or to inhibit factor Xa activity in the individual to the desired extent. Such an effective amount or does to be administered has to be adjusted to the individual circumstances in each case. It can be readily determined by the use of conventional techniques using the methods described herein or otherwise known in the art, and by observing results obtained under analogous circumstances. In determining the effective dose, a number of factors are considered including, but not limited to: the species of patient; its size, age, and general health; the specific disease involved; the degree or the involvement or the severity of the disease; the response of the individual patient; the particular compound administered; the mode of administration; the bioavailability characteristics of the pharmaceutical preparation administered; the dose regimen selected; and the use of comcomitant medication. An appropriate dosage can be established using clinical approaches well known in the medical art.

In general, in view of the above factors it is evident that the effective factor Xa inhibitory amount or the therapeutically effective amount of a compound of formula (I) will vary and can be varied within wide limits. Usually, an effective amount will vary from about 0.01 milligram per kilogram of body weight per day (mg/kg per day) to about 20 mg/kg per day. A daily dose of from about 0.1 mg/kg to about 10 mg/kg is typical. These data refer to a human of about 75 kg of body weight. In particular when administering relatively large quantities, it can be favorable to subdivide the daily dose into several, for example 2, 3, or 4 subdose administrations.

A compound of formula (I) can be administered to an individual for the treatment of a variety of clinical conditions, including, for example, the treatment and prophylaxis of cardiovascular disorders or complications associated, for example, with infection or surgery. Examples of cardiovascular disorders include restenosis, for example, restenosis following angioplasty, reocclusion prophylaxis, conditions after coronary bypass operations, arterial, venous, and microcirculatory disease states, cardiac infarction, angina pectoris, thromboembolic diseases, thromboses, embolism, adult respiratory distress syndrome, multi-organ failure, stroke, or disseminated intravascular coagulation clotting disorder. Examples of related complications associated with surgery include, for example, deep vein and proximal vein thrombosis, which can occur following surgery. Thus, a compound of the invention is useful as a medicament for reducing or inhibiting unwanted coagulation or blood clotting in an individual.

The compounds of formula (I), their physiologically acceptable salts and other suitable derivatives thereof can be employed as medicaments or pharmaceuticals in the above-mentioned methods on their own, in mixtures with each other or in the form of pharmaceutical compositions which comprise, as the active ingredient, an effective amount of at least one compound of formula (I) and/or of a physiologically acceptable salt and/or another suitable derivative thereof in admixture or otherwise in association with one or more pharmaceutically acceptable carrier substances and auxiliary substances.

In effecting treatment of a patient, compounds of formula (I) on their own or pharmaceutical compositions comprising them can be administered in any form or mode which makes the compounds of formula (I) bioavailable in effective amounts, including oral and parenteral routes. For example, they can be administered orally, subcutaneously, intramuscularly, intravenously, transdermally, intranasally, rectally, and the like. Oral administration is generally preferred, but depending on the specific case other modes of administration can also be favourable, for example, in an acute stage of a disease intravenous administration by means of injection or infusion. One skilled in the art of preparing formulations can readily select the proper form and mode of administration depending upon the disease state to be treated, the stage of the disease, and other relevant circumstances.

Pharmaceutical compositions or medicaments comprising a compound of formula (I) and/or a physiologically acceptable salt and/or another suitable derivative thereof can be made by combining the compounds of formula (I) and/or their physiologically acceptable salts and/or other suitable derivatives thereof with pharmaceutically acceptable carrier substances and auxiliary substances, the proportion and nature of which are determined by the chosen route of administration and standard pharmaceutical practice. The pharmaceutical compositions or medicaments are prepared in a manner well known in the pharmaceutical art. The pharmaceutical compositions will, in general, contain an effective amount of a compound of formula (I) and/or a physiologically acceptable salt and/or another suitable derivative thereof together with a suitable amount of a carrier so as to comprise the proper dosage for administration to an individual. The pharmaceutical compositions may be adapted for oral or parenteral use and may be administered to the patient in the form, for example, of tablets, capsules, suppositories, solutions, suspensions, ointments, tinctures, nasal sprays, aerosol mixtures, implants, rods, microcapsules, or the like. Thus, together with the claimed compounds the present invention provides useful pharmaceutical compositions or medicaments for inhibiting factor Xa activity and blood clotting in an individual.

The present invention further encompasses a process for the preparation of pharmaceutical compositions or medicaments which comprise at least one compound of formula (I) and/or a physiologically acceptable salt and/or another suitable derivative thereof, as well as it encompasses the use of the compounds of formula (I) and/or physiologically acceptable salts and/or other suitable derivatives thereof for the preparation of medicaments, especially of medicaments for the treatment or prophylaxis of the above-mentioned diseases.

Pharmaceutically acceptable carriers and auxiliary substances are substances or compositions that are non-toxic to an individual or have acceptable toxicity as determined by the appropriate regulatory agency. The carrier substance or excipient may be a solid, semi-solid, or liquid material which can serve as a vehicle or medium for the active ingredient. As used herein, the term "pharmaceutically acceptable carrier" encompasses any of the standard pharmaceutical carriers such as liquid carriers (for example, phosphate buffered saline), water, an emulsion (such as an oil/water or water/oil emulsion), or solid or semi-solid carriers (such as, for example, lactose, corn starch, fats, waxes, etc). Suitable pharmaceutical carriers and their formulations are well known in the art and are, for example, described by Martin in Remington's Pharmaceutical Sciences, $15^{th}$ Ed. (Mack Publishing Co., Easton 1975) which is incorporated herein by reference also with respect to other aspects of the ingredients and the preparation of pharmaceutical compositions.

Examples of auxiliary substances are fillers, disintegrants, binders, glidants, wetting agents, stabilizers, emulsifiers, preservatives, sweeteners, dyes, flavorants, aromatizing agents, thickeners, diluents, buffering substances, solubilizing agents, agents for achieving a slow-release effect, salts for altering the osmotic pressure, coating agents, antioxidants, etc.

For the purpose of oral administration, the compounds of formula (I) may be incorporated with excipients or inert diluents or edible carriers and used in the form of, for example, tablets, film tablets, coated tablets, pills, troches, capsules, granules, solutions, suspensions, emulsions, elixirs, syrups, wafers, chewing gums, and the like, or they may be enclosed in gelatin capsules. The pharmaceutical compositions for oral administration may be varied depending upon the particular form. Usually they contain at least 1% of the active ingredient of formula (I) and may conveniently contain up to about 90% of the weight of the unit. Typically, the content of the compounds of formula (I) and/or their physiologically acceptable salts and/or other suitable derivatives is from about 4% to about 70% by weight. The amount of the active ingredient present in the compositions is such that a unit dosage form suitable for administration will be obtained.

The tablets, pills, capsules, troches and the like may also contain, for example, one or more of the following carrier and auxiliary substances: binders, such as microcrystalline cellulose, gum tragacanth, or gelatin; excipients, such as starch or lactose; disintegrating agents, such as alginic acid, Primogel, corn starch, and the like; lubricants, such as magnesium stearate or Sterotex; glidants, such as colloidal silicon dioxide; sweetening agents, such as sucrose or saccharin; or flavoring agents, such as peppermint, methyl salicylate, or orange flavoring. When the dosage unit form is a capsule, it may contain, in addition to materials of the above type, a liquid carrier such as polyethylene glycol or a fatty oil. Other dosage unit forms may contain other various materials which modify the physical form of the dosage unit, for example, as coatings. Thus, tablets or pills may be coated with sugar, shellac, or other enteric coating agents. A syrup may contain, in addition to the active ingredient, other ingredients, for example, sucrose as a sweetening agent and certain preservatives, dyes, colorings, and flavors.

For the purpose of parenteral administration, the compounds of formula (I) and/or physiologically acceptable salts thereof and/or other suitable derivatives thereof may be incorporated into a solution or a suspension. The solutions or suspensions may, for example, also include one or more of the following carrier and auxiliary substances: sterile diluents such as water for injection, saline solution, fixed oils, polyethylene glycols, glycerine, propylene glycol or other synthetic solvents; antibacterial agents such as benzyl alcohol or methyl paraben; antioxidants such as ascorbic acid or sodium bisulfite; chelating agents such as ethylene diaminotetraacetic acid; buffers such as acetates, citrates, or phosphates; agents for the adjustment of toxicity such as sodium chloride or dextrose. The content of the compounds of formula (I) in the preparations for parenteral administration may be varied. Usually they contain at least 0.1% by weight of the compound of formula (I). Typically, the content of the compound of formula (I) and/or the physiologically acceptable salts thereof and/or other suitable derivatives thereof is from about 0.1% to 50%. The parenteral preparations can be enclosed in ampules, disposable syringes, multiple dose vials made of glass or plastic, or infusion bottles. Suitable excipients for microcapsules, implants and rods are, for example, mixed polymers of glycolic acid and lactic acid.

Materials used in preparing the various pharmaceutical compositions should be pharmaceutically pure and non-toxic in the amounts used.

Besides one or more compounds of formula (I) and/or one or more physiologically acceptable salts thereof and/or one or more other suitable derivatives thereof as active compounds the pharmaceutical compositions according to the present invention may also contain one or more other pharmacologically active compounds.

In another, more general embodiment the present invention provides compositions comprising at least one compound of formula (I) and/or salt thereof and/or another suitable derivative thereof in admixture or otherwise in association with one or more inert carriers. These compositions are useful, for example, as assay standards, as convenient means of making bulk shipments, or as pharmaceutical compositions. An assayable amount of a compound of formula (I) is an amount which is readily measurable by standard assay procedures and techniques as are well known and appreciated by those skilled in the art. Assayable amount of a compound of formula (I) will generally vary from about 0.001% to about 90% of the composition by weight. Inert carriers can be any material which does not degrade or otherwise covalently react with a compound of formula (I). Examples of suitable inert carriers are water; aqueous buffers, such as, for example, those which are generally useful in High Performance Liquid Chromatography (HPLC) analysis; organic solvents, such as acetonitrile, ethyl acetate, hexane, and the like; and pharmaceutically acceptable carrier and auxiliary substances.

The compounds of formula (I) can also be used as starting materials or chemical intermediates in the preparation of other compounds, especially in the preparation of other pharmacologically active compounds. Examples for such conversions of compounds of the invention into other compounds of the invention are given below. In this manner, other compounds of formula (I), including physiologically acceptable and unacceptable salts thereof, may be useful as starting materials, though they may or may not be suitable for use as pharmaceuticals. Thus, the present invention also relates to compounds of the formula (I) and their salts, in general, as chemical intermediates, especially as intermediates in the preparation of pharmacologically active compounds.

The following tests can serve to investigate the pharmacological activity and to illustrate the utility of the compounds of the present invention as factor Xa inhibitors.

Test 1: In Vitro Inhibition of Selected Purified Coagulation Enzymes and Other Serine Proteases The ability of a compound of formula (I) to inhibit factor Xa, thrombin, plasmin, elastase, and trypsin may be assessed by determining the concentration of compound of formula (I) that inhibits enzyme activity by 50% ($IC_{50}$). Purified enzymes are used in chromogenic assays. To determine the inhibition constant, the $IC_{50}$ value is corrected for competition with substrate using the formula:

$$K_i = IC_{50} \times (1/\{1+((\text{substrate concentration})/\text{substrate } Km)\})$$

where Km is the Michaelis-Menten constant. Y. -C. Chen and W. H. Prusoff, Biochem. Pharmacol. 22: 3099-3018 (1973), which is incorporated herein by reference.

a. Factor Xa Assay

TBS-PEG buffer (50 mM Tris-Cl, pH 7.8, 200 mM NaCl, 0.05% (w/v) PEG-8000, 0.02% (w/v) $NaN_3$) is used for this assay. The $IC_{50}$ is determined by combining in appropriate wells of a Costar half-area microtiter plate 25 µl human factor Xa (Enzyme Research Laboratories, Inc.; South Bend, Ind.) in TBS-PEG; 40 µl 10% (v/v) DMSO in TBS-PEG (uninhibited control) or various concentrations of the compound to be tested diluted in 10% (v/v) DMSO in TBS-PEG; and substrate S-2765 (N-benzyloxycarbonyl-D-Arg-Gly-L-Arg-p-nitroanilide; Kabi Pharmacia, Inc.; Franklin Ohio) in TBS-PEG.

The assays are performed by pre-incubating the compound of formula (I) plus enzyme for 10 min, then the assay is initiated by adding substrate to obtain a final volume of 100 µl. The initial velocity of chromogenic substrate hydrolysis is measured by the change in absorbance at 405 nm using a Bio-tek Instruments kinetic plate reader (Ceres UV900HDi) at 25° C. during the linear portion of the time course (usually 1.5 min after addition of substrate). The concentration of inhibitor that causes a 50% decrease in the rate of substrate hydrolysis is predicted by linear regression after plotting the relative rates of hydrolysis (compared to the uninhibited control) versus the log of the compound of formula (I) concentration. The enzyme concentration is 0.5 nM and substrate concentration is 140 µM.

b. Thrombin Assay

TBS-PEG buffer is used for this assay. The $IC_{50}$ is determined as above for the Factor Xa assay, except that the substrate is S-2366 (L-PyroGlu-L-Pro-L-Arg-p-nitroanilide; Kabi) and the enzyme is human thrombin (Enzyme Research Laboratories, Inc.; South Bend Ind.). The enzyme concentration is 175 µM.

c. Plasmin Assay

TBS-PEG buffer is used for this assay. The $IC_{50}$ is determined as described above for the factor Xa assay, except that the substrate is S-2251 ((D)-Val-L-Leu-L-Lys-p-nitroanilide; Kabi) and the enzyme is human plasmin (Kabi). The enzyme concentration is 5 nM and the substrate concentration is 300 µM.

d. Trypsin Assay

TBS-PEG buffer containing 10 mM $CaCl_2$ is used for this assay. The $IC_{50}$ is determined as described above in the factor Xa assay, except that the substrate is BAPNA (Benzoyl-L-Arg-p-nitroanilide; Sigma Chemical Co.; St. Louis Mo.) and the enzyme is bovine pancreatic trypsin (Type XIII, TPCK treated; Sigma). The enzyme concentration is 50 nM and the substrate concentration is 300 µM.

e. Elastase Assay

Tris-Cl, pH 7.4, 300 mM NaCl, 2% (v/v) N-methyl-pyrrolidone, 0.01% (w/v) $NaN_3$ buffer is used for this assay. The $IC_{50}$ is determined as described above in the factor Xa assay, except that the substrate is succinyl-Ala-Ala-Ala-p-nitroanilide (Calbiochem-Nova Biochem Corp.; San Diego Calif.) and the enzyme is human neutrophil elastase (Athens Research and Technology, Inc.; Athens Ga.). The enzyme concentration is 75 nM and the substrate concentration is 600 μM. The control compound is "TENSTOP" (N-alpha-tosyl-Gly-p-amidinophenylalanine methyl ester; American Diagnostica, Inc.; Greenwish Conn.), which is a reversible factor Xa inhibitor (Stuerzebecher et al., Thromb. Res. 54: 245–252 (1989); Hauptmann et al., Thromb. Haem. 63: 220–223 (1990), each of which is incorporated herein by reference).

Test 2: Assays for Determining Inhibition of Coagulation

The effectiveness of compounds of formula (I) may be assessed by the in vitro prothrombin time (PT) assay using pooled human donor plasma. An ex vivo assay may also be used in which plasma is collected at various times after intravenous ("iv") administration of a compound of formula (I) to rats or to rabbits or intraduodenal ("id") administration to rats and analysis using the PT assay to determine plasma half-life. The PT assay is initiated with a thromboplastin dilution selected to obtain an extended and highly reproducible coagulation endpoint, referred to as the "dilute PT assay" as described below. The effectiveness of various compounds may also be determined using an in vivo rat arteriovenous shunt model of thrombosis.

a. In Vitro Dilute Prothrombin Time Assay

100 μl prewarmed (37° C.) pooled human platelet poor plasma (PPP) is added to a fibrometer cup (Baxter Diagnostics., Inc.; McGaw Park Ill.). 50 μl of various concentrations of a compound of formula (I) in TBS-BSA with calcium (50 mM Tris-Cl, 100 mM NaCl, 0.1% (w/v) bovine serum albumin, 20 mM $CaCl_2$) is added. In control experiments, TBS-BSA with calcium, but without test compound of formula (I), is added for measurement of uninhibited coagulation time. 150 μl diluted prewarmed rabbit thromboplastin (Baxter) with calcium is added to the fibrometer cup and the fibrometer timer is started. A rabbit thromboplastin dilution curve is obtained prior to treating the compound and is used to choose a thromboplastin dilution that allows approximately 30 sec PT time for uninhibited controls. The experimental concentration giving 50% inhibition of coagulation ($EC_{50}$) with test compound is calculated from the dilution curve times.

Alternatively, the dilute prothrombin time assay is conducted using the "research" mode on an Instrumentation Laboratories (IL) ACL3000-plus automated coagulation instrument (IL; Milan, Italy). Thromboplastin is diluted until a clotting time of 30–35 seconds is achieved. This clotting time is taken as 100% activity. A standard curve for calibration is established by serial 2-fold dilution of the diluted thromboplastin reagent (rabbit brain IL-brand thromboplastin). During the assay, a 50 μl sample (plasma separated by centrifugation) is mixed with 100 μl thromboplastin reagent and nephelometric readings are taken over 169 sec. Coagulation time is determined from the maximal rate of change of light scatter calculated by the instrument. Inhibition is expressed as percent activity as determined by comparison with the calibration curve.

b. Ex Vivo Dilute Prothrombin Time Assay

A test compound of formula (I) is administered iv either through the tail vein (rat) or ear vein (rabbit) following an approved protocol. 0.5 ml blood samples are removed at timed intervals after administration of a test compound of formula (I) from a cannulated carotid artery (rat) or auricular artery (rabbit). After centrifugation to obtain PPP, the plasma is immediately stored on ice or frozen.

For dilute prothrombin time determination, the plasma is prewarmed and assayed as described above. Percent inhibition is calculated from a thromboplastin dilution curve, which is run with each series of samples, and used to determine the time at which approximately 50% of the initial anticoagulant activity remains in the plasma ($T_{1/2}$).

The test compounds of formula (I) can also be administered to rats using an intraduodenal dosing protocol. Male Sprague-Dawley rats weighing approximately 300 g are anesthetized with a combination of ketamine/xylazine, subcutaneously, following and approved protocol. The right carotid artery is cannulated for blood sampling. A laparotomy is performed and duodenum is cannulated with a ball-tip needle and tied into place to ensure that the suture is distal to the point of insertion. An additional tie is placed proximal to the insertion point to prevent leakage of gastric contents. The effectiveness of the suture in preventing a compound from reaching the site of insertion is tested by pressure testing at the conclusion of each experiment. The point of insertion is approximately 4 cm from the duodenal-gastric junction. Compounds are administered in 1 ml normal saline. A 0.7 ml blood sample is drawn prior to administration of the test compound of formula (I) and at 15, 30, 60, 90 and 120 min after administration. Plasma is separated by centrifugation and assayed for inhibition of coagulation using the dilute prothrombin time assay.

c. Rat Arteriovenous Shunt Model of Thrombosis

The anti-thrombotic efficacy of various compounds of the invention may be assessed using rat extracorporeal arteriovenous (AV) shunt. The AV shunt circuit consisted of a 20 cm length of polyethylene (PE) 60 tubing inserted into the right carotid artery, a 6 cm length of PE 160 tubing containing a 6.5 cm length of mercerized cotton thread (5 cm exposed to blood flow), and a second length of PE 60 tubing (20 cm) completing the circuit into the left jugular vein. The entire circuit is filled with normal saline prior to insertion.

Test compounds of formula (I) are administered by continuous infusion into the tail vein using a syringe pump and butterfly catheter (infusion volume 1.02 ml/h). A compound is administered for 30 min, then the shunt is opened and blood allowed to flow for a period of 15 min (total of 45 min infusion). At the end of the 15 min period, the shunt is clamped and the thread is carefully removed and weighed on an analytical balance. Percent inhibition of thrombus formation is calculated using the thrombus weight obtained from control rats, which are infused with saline.

The following Table 1 shows the factor Xa inhibitory activities ($K_i$-values) of selected compounds of the formula (I) (testing the compounds for inhibitory activity was accomplished using the in vitro factor Xa assay described above (Test 1a).

| Example | $K_i$ (Xa) [μM] |
|---|---|
| 4 | 0.002 |
| 5 | 0.005 |
| 6 | 0.005 |
| 7 | 7.65 |
| 10 | 0.0009 |
| 18 | 0.31 |
| 23 | 0.0028 |
| 26 | 1.07 |
| 39 | 2.89 |
| 51 | 3.86 |
| 57 | 1.93 |
| 66 | 0.0023 |
| 70 | 0.030 |
| 79 | 0.0225 |
| 82 | 2.84 |
| 86 | 0.6 |
| 95 | 0.0091 |
| 96 | 0.0084 |
| 100 | 0.44 |

-continued

| Example | $K_i$ (Xa) [μM] |
|---|---|
| 106 | 0.067 |
| 110 | 0.002 |
| 111 | 0.059 |
| 113 | 0.006 |
| 119 | 0.011 |
| 122 | 0.016 |
| 124 | 0.001 |
| 125 | 2.57 |
| 126 | 0.011 |
| 131 | 0.005 |
| 133 | 0.001 |
| 135 | 0.013 |
| 137 | 0.004 |
| 138 | 0.055 |
| 140 | 0.003 |
| 141 | 0.10 |
| 149 | 0.023 |
| 151 | 0.004 |
| 153 | 5.84 |
| 154 | 0.31 |
| 157 | 0.019 |
| 159 | 0.011 |
| 161 | 0.008 |
| 162 | 0.025 |
| 163 | 0.001 |
| 165 | 0.002 |
| 167 | 0.074 |
| 170 | 0.033 |
| 172 | 0.072 |
| 176 | 0.001 |
| 177 | 0.001 |
| 181 | 0.013 |
| 183 | 0.025 |
| 184 | 0.019 |
| 188 | 0.022 |
| 189 | 0.020 |
| 192 | 0.044 |
| 194 | 0.034 |
| 195 | 0.032 |
| 196 | 0.039 |
| 201 | 0.042 |
| 202 | 0.028 |
| 214 | 0.047 |
| 216 | 0.019 |
| 219 | 0.005 |
| 222 | 0.043 |
| 223 | 0.001 |
| 228 | 0.003 |
| 230 | 0.001 |
| 232 | 0.024 |
| 233 | 0.033 |
| 235 | 0.012 |
| 236 | 0.005 |
| 241 | 0.025 |
| 242 | 0.002 |
| 243 | 0.025 |
| 246 | 0.0007 |
| 252 | 0.031 |
| 258 | 0.008 |
| 262 | 0.019 |
| 263 | 0.025 |

EXAMPLES

The following examples present typical syntheses of the compounds of formula (I). These examples are understood to be illustrative only and are not intended to limit the scope of the present invention in any way. The compounds of the examples were characterized by mass spectra (MS) and/or NMR spectra and/or melting point.

Example 1

2-(S)-{2-[3-(4-Carbamimidoyl-phenyl)-2-cyclohexyl-propionylamino]-2-cyclohexyl-acetylamino}-5-guanidino-pentanoic acid phenethyl-amide acetic acid salt, less polar diastereomeric mixture and 2-(S)-{2-[3-(4-Carbamimidoyl-phenyl)-2-cyclohexyl-propionylamino]-2-cyclohexyl-acetylamino}-5-guanidino-pentanoic acid phenethyl-amide acetic acid salt, more polar diastereomeric mixture a) Cyclohexyl-acetyl chloride Cyclohexyl-acetic acid (288 ml, 2.04 mol) and thionyl chloride (306 ml, 4.19 mol) were stirred in a 1000 ml flask fitted with reflux condenser, $CaCl_2$ drying tube, thermometer, heating mantle, and magnetic stirrer. The reaction solution was heated to 50° C. with stirring (gas evolution). After 14.5 hours at 50° C., the reaction mixture was further heated to a gentle reflux for 90 min and then cooled to room temperature. Excess thionyl chloride was removed under reduced pressure. The residual liquid was vacuum distilled to afford cyclohexyl-acetyl chloride (250.92 g, 77%) as a pale yellow liquid. bp.: 60° c./5 mm Hg; MS m/z: 161 (M+H)+.

b) Cyclohexyl-acetic acid tert-butyl ester

To a 5° C. solution of dimethylaniline (320 ml, 2.54 mol) in t-butyl alcohol (480 ml) was added dropwise a solution of cyclohexyl-acetyl chloride (250.9 g, 1.56 mol) in dichloromethane (320 ml) over 30 min. At the end of the addition, the addition funnel was rinsed with dichloromethane (80 ml). The reaction mixture was stirred 90 min at 5° C. and then allowed to warm to room temperature. After 15 hours at room temperature, the reaction solution was heated to reflux for 6 hours and then cooled to 5° C. The cold reaction mixture was acidified with 6 n hydrogen chloride (640 ml) and extracted with ethyl acetate. The organic layer was washed with 1 N hydrogen chloride (860 ml), water (2×860 ml), saturated aqueous sodium bicarbonate solution (2×860 ml), and brine (860 ml). The organic solution was dried (magnesium sulfate), filtered, and concentrated (room temperature/20 mm Hg). The remaining liquid was distilled to afford the desired product as a yellow oil (259.32 g, 84%). bp.: 70–75° C./0.6 mm Hg; MS m/z: 199 (M+H)+.

c) 3-(4-Cyano-phenyl)-2-(R,S)-cyclohexyl-propionic acid tert-butyl ester n-Butyllithium (1.6 M in hexanes; 40.6 ml, 64.9 mmol) and diisopropylamine (9.1 ml, 64.9 mmol) were sequentially added to −78° C. tetrahydrofuran (90 ml) under nitrogen with stirring. The lithium diisopropylamide solution was stirred 15 min at −78° C. and then allowed to warm to 0° C. The lithium diisopropylamide solution was cooled to −78° C. and cyclohexyl-acetic acid tert-butyl ester (12.8 g, 64.5 mmol) was added dropwise over 10 min to the −70° C. lithium diisopropylamide solution with stirring. Enolate formation was allowed to occur over 15 min. The ester enolate thus formed was treated with a solution of 4-cyanobenzyl bromide (12.5 g, 64 mmol) in tetrahydrofuran (60 ml) and 1,3-dimethyl-3,4,5,6-tetrahydro-2(1H)-pyrimidinone (15.9 ml, 132 mmol). The reaction mixture was stirred 2 hours at −70° C., then allowed to warm to room temperature over 20.5 hours. Evaporation of solvents (30° C. at 20 mm Hg) left an oil that was partitioned between a mixture of ethyl acetate and water. The aqueous layer was extracted with ethyl acetate and the combined organic phases were washed with saturated aqueous ammonium chloride, water, saturated aqueous sodium bicarbonate solution, and brine (200 ml), dried (magnesium sulfate), filtered, and concentrated on a rotary evaporator (30° C. at 20 mm Hg). Vacuum distillation of the residue afforded the desired product (13.69 g, 68% as a yellow oil. bp.: 160° C./0.60 mm Hg, MS m/z: 314 (M+H)$^+$.

d) 3-(4-Cyano-phenyl)-2-(R,S)-cyclohexyl-propionic acid

To a solution of 3-(4-cyanophenyl)-2-(R,S)-cyclohexyl-propionic acid t-butyl ester (8.2 g, 26.2 mmol) in dichloromethane (70 ml) was added trifluoroacetic acid (14.1 ml, 183.0 mmol) with stirring at room temperature. A gentle gas evolution ensued. After 69 h, solvent and excess trifluoroacetic acid were evaporated under reduced pressure. The solid was taken up in ethyl acetate and washed with water and brine, then dried (magnesium sulfate), filtered, and evaporated to dryness. The crude product was dissolved in methanol, treated with decolorizing carbon, filtered through celite, and concentrated. The resultant solid was recrystalized from toluene to afford the desired product as an off-white powder (6.83 g, 58%). mp.: 115–117° C., MS m/z: 258 (M+H)$^+$.

e) [3-(4-Cyano-phenyl)-2-(R,S)-cyclohexyl-propionylamino]-(S)-cyclohexyl-acetic acid methyl ester A solution of 3-(4-cyano-phenyl)-2-(R,S)-cyclohexyl-propionic acid (8.8 g, 34.2 mmol, prepared as described in example 1d), (S)-amino-cyclohexyl-acetic acid methyl ester (6.27 g, 36.6 mmol), diisopropylethylamine (6.8 ml, 40.0 mmol), 3-hydroxy-3H-benzo[d][1,2,3]triazin-4-one (1.40 g, 8.6 mmol), and dimethylformamide (200 ml) was cooled to 10° C. A solution of dicyclohexyl-carbodiimide (8.26 g, 40.0 mmol) in toluene (8 ml) was added dropwise over a period of 3 hours and the reaction mixture was stirred for 36 hours. The precipitated urea was sucked off and the filtrate was evaporated in vacuo. Crystallization from n-heptane/isopropanol gave 10.68 g of the desired product, which contained 1,3-dicyclohexyl-urea. The crude material was used without further purification. MS m/z: 411 (M+H)$^+$.

f) (S)-Cyclohexyl-{2-(R,S)-cyclohexyl-3-[4-(N-hydroxycarbamimidoyl)-phenyl]-propionylamino}-acetic acid methyl ester A suspension of (S)-cyclohexyl-{2-(R,S)-cyclohexyl-3-[4-(N-hydroxycarbamimidoyl)-phenyl]-propionylamino}-acetic acid methyl ester (10.68 g) and hydroxylamine (4.3 g, 0.13 mol) in ethanol (150 ml) was heated to reflux for 4 hours. The reaction mixture was cooled to room temperature, evaporated in vacuo, solved in ethanol, and poured into ice-water. The precipitate was collected by suction and dried at 50° C. in vacuo to give 4.74 g crude product, which was used in the next step without further purification. MS m/z: 444 (M+H)$^+$.

g) [3-(4-Carbamimidoyl-phenyl)-2-(R,S)-cyclohexyl-propionylamino]-(S)-cyclohexyl-acetic acid methyl ester acetic acid salt (S)-Cyclohexyl-{2-(R,S)-cyclohexyl-3-[4-(N-hydroxycarbamimidoyl)-phenyl]-propionylamino}-acetic acid methyl ester (5.52 g, contains 1.5 g 1,3-dicyclohexyl-urea, 9.06 mmol) was dissolved in acetic acid (50 ml). After addition of palladium on charcoal (10%, 100 mg), hydrogen was bubbled in the reaction mixture at room temperature for 2 hours and at 50° C. for 15 hours. The catalyst was filtered off and washed with water. Addition of water to the filtrate caused a precipitate which was filtered off and dried to yield 1.5 g of 1,3-dicyclohexyl-urea. The filtrate was evaporated to yield the desired product, which was used without further purification in the next step. MS m/z: 428.3 (M+H)$^+$.

h) [3-(4-Carbamimidoyl-phenyl)-2-(R,S)-cyclohexyl-propionylamino]-(S)-cyclohexyl-acetic acid hydrochloric acid salt

[3-(4-Carbamimidoyl-phenyl)-2-(R,S)-cyclohexyl-propionylamino]-(S)-cyclohexyl-acetic acid methyl ester acetic acid salt was dissolved in a mixture of hydrochloric acid (100 ml), water (100 ml) and acetic acid (50 ml) within 1 hour. After 15 hours stirring at room temperature and 8 hours at 50° C., the mixture was evaporated and after addition of water lyophilized to yield a diastereomeric mixture (2.7 g, 72% step g and h) of the desired product. MS m/z: 414.3 (M+H)$^+$.

The pure (more and less polar) diastereomers were available by purification over Sephadex LH20 using n-butanol (17): glacial acetic acid (1) and water (2) as eluent.

i) 2-(S)-{2-[3-(4-Carbamimidoyl-phenyl)-2-cyclohexyl-propionylamino]-2-cyclohexyl-acetylamino}-5-guanidino-pentanoic acid phenethyl-amide acetic acid salt At 4° C. TOTU (48 mg, 0.14 mmol) was added to a solution of [3-(4-carbamimidoyl-phenyl)-2-(R,S)-cyclohexyl-propionylamino]-(S)-cyclohexyl-acetic acid hydrochloric acid salt (60 mg, 0.14 mmol), (S)-2-amino-5-guanidino-pentanoic acid phenethyl-amide dihydrochloride (51 mg, 0.14 mmol) and N-ethylmorpholine (56 µl, 0.42 mmol) in dimethylformamide (10 ml). The mixture was stirred at 22° C. for 15 hours. The solvent was evaporated and the residue was purified by column chromatography (Sephadex LH20, n-butanol/acetic acid/water 17:1:2) to give two stereoisomeric product mixtures. more polar diastereomeric mixture: 41 mg MS m/z 673.6 (M+H)$^+$. less polar diastereomeric mixture: 21 mg MS m/z 673.6 (M+H)$^+$. Total yield: 57%.

Example 2

2-(S)-(2-{[3-(4-Carbamimidoyl-phenyl)-2-(R,S)-cyclohexyl-propionyl]-cyclohexylmethyl-amino}-acetylamino)-5-guanidino-pentanoic acid amide acetic acid salt hydrochloric acid salt a) {[3-(4-Cyano-phenyl)-2-(R,S)-cyclohexyl-propionyl]-cyclohexylmethyl-amino}-acetic acid tert-butyl ester To 3-(4-cyano-phenyl)-2-(R,S)-cyclohexyl-propionic acid (5 g, 19.43 mmol) and (cyclohexylmethyl-amino)-acetic acid tert-butyl ester (4.42 g, 19.43 mmol) in dimethylformamide (50 ml) were added TOTU (7.01 g, 21.37 mmol) and diisopropylethyl amine (2.51 g, 19.43 mmol) at −15° C. The mixture was stirred for 1 hour and then allowed to warm to room temperature. After evaporation, the residue was treated with sodium bicarbonate solution and extracted with ethyl acetate. The organic layer was evaporated to yield 10 g of crude material which was used in the next step without further purification, MS m/z: 467.4 (M+H)$^+$.

b) ({2-(R,S)-Cyclohexyl-3-[4-(N-hydroxycarbamimidoyl)-phenyl]-propionyl}-cyclohexylmethyl-amino)-acetic acid {[3-(4-Cyano-phenyl)-2-(R,S)-cyclohexyl-propionyl]-cyclohexylmethyl-amino}-acetic acid tert-butyl ester (2.0 g, 4.29 mmol), hydroxylamine hydrochloride (0.89 g, 12.87 mmol) and triethylamine (1.3 g, 12.87 mmol) were stirred in isopropanol (80 ml) at room temperature for 24 hours. After evaporation, the residue was treated with potassium hydrogen sulfate solution and extracted with dichloromethane. The organic layer was dried and evaporated. Yield: 1.52 g (80%), MS m/z: 444.3 (M+H)$^+$.

c) {[3-(4-Carbamimidoyl-phenyl)-2-(R,S)-cyclohexyl-propionyl]-cyclohexylmethyl-amino}-acetic acid ({2-(R,S)-Cyclohexyl-3-[4-(N-hydroxycarbamimidoyl)-phenyl]-propionyl}-cyclohexylmethyl-amino)-acetic acid (1.5 g, 3.38 mmol) was dissolved in acetic acid (40 ml). After addition of palladium on charcoal (10%, 100 mg), hydroxgen was bubbled in the reaction mixture at 50°C. for 8 hours. The catalyst was filtered off and washed with acetic acid. The filtrate was evaporated, the residue dissolved in water, lyophilized and purified by chromatography on Sephadex LH20 employing n-butanol (17): glacial acetic acid (1): water (2) was eluent. Pure fractions were combined. The solvent was evaporated, the residue was taken up in water, and the aqueous solution was lyophilized. Yield: 190 mg (13%), MS m/z 428.4 (M+H)$^+$.

d) 2-(S)-(2-{[3-(4-Carbamimidoyl-phenyl)-2-(R,S)-cyclohexyl-propionyl]-cyclohexylmethyl-amino}-acetylamino)-5-guanidino-pentanoic acid amide acetic acid salt hydrochloric acid salt To {[3-(4-carbamimidoyl-phenyl)-2-2-(R,S)-cyclohexyl-propionyl]-cyclohexylmethyl-amino}-acetic acid (50 mg, 0.12 mmol) and 2-(S)-amino-5-guanidino-pentanoic acid amide dihyrochloride (30 mg, 0.12 mmol) in dimethylformamide (5 ml) were added at −15° C. TOTU (44 mg, 0.13 mmol) and N-ethylmorpholine (40 µl, 0.32 mmol). The mixture was stirred for 1 hour and then allowed to warm to room temperature. After evaporated, the residue was treated with sodium bicarbonate solution and extracted with ethyl acetate. The aqueous layer was evaporated and purified by chromatography on Sephadex LH20 employing n-butanol (17): glacial acetic acid (1): water (2) as eluent. Pure fractions were combined. The solvent was evaporated, the residue was taken up in water, and the aqueous solution was lyophilized. Yield: 12 mg (15%), MS m/z: 292.4 (M+2H)$^{2+}$.

Example 3

2-(S)-{2-(S)-[3-(4-Carbamimidoyl-phenyl)-2-cyclohexyl-propionylamino]-2-cyclohexyl-acetylamino}-5-guanidino-pentanoic acid amide acetic acid salt, more polar diastereomer To [3-(4-carbamimidoyl-phenyl)-2-cyclohexyl-propionylamino]-(S)-cyclohexyl-acetic acid (41 mg, 0.1 mmol, less polar diastereomer, example 1h) and 2-(S)-amino-5-guanidino-pentanoic acid amide dihyrochloride (24.6 mg, 0.1 mmol) in dimethylformamide (5 ml) were added HATU (39 mg, 0.1 mmol) and collidine (24.2 mg, 0.2 mmol) at 0° C. The mixture was stirred for 1 hour and then allowed to warm to room temperature. After evaporation, the residue was purified by chromatography on Sephadex LH20 employing n-butanol (17): glacial acetic acid (1): water (2) as eluent. Pure fractions were combined. The solvent was evaporated, the residue was taken up in water, and the aqueous solution was lyophilized. Yield: 50 mg (74%), MS m/z: 569.5 (M+H)$^+$, 285.4 (M+2H)$^{2+}$.

Example 4

2-(S)-{2-(S)-[3-(4-Carbamimidoyl-phenyl-2-cyclohexyl-propionylamino]-2-cyclohexyl-acetylamino}-5-guanidino-pentanoic acid amide acetic acid salt, less polar diastereomer 2-(S)-{2-(S)-[3-(4-Carbamimidoyl-phenyl)-2-cyclohexyl-propionylamino]-2-cyclohexyl-acetylamino}-5-guanidino-pentanoic acid amide acid salt, less polar diastereomer, was prepared from (S)-[3-(4-carbamimidoyl-phenyl)-2-cyclohexyl-propionylamino]-cyclohexyl-acetic acid (less polar diastereomer, example 1 h), 2-(S)-amino-5-guanidino-pentanoic acid amide dihydrochloride. HATU, and collidine in dimethylformamide as described in example 3 to yield 46% of the desired product. MS m/z: 569.5 (M+H)$^+$, 285.4 (M+2H)$^{2+}$.

Example 5

2-(S)-{2-(S)-[3-(4-Carbamimidoyl-phenyl)-2-cyclohexyl-propionylamino]-2-cyclohexyl-acetylamino}-5-guanidino-pentanoic acid ethyl ester, less polar diastereomer.

2-(S)-{2-(S)-[3-(4-Carbamimidoyl-phenyl)-2-cyclohexyl-propionylamino]-2-cyclohexyl-acetylamino}-5-guanidino-pentanoic acid ethyl ester, less polar diastereomer, was prepared from (S)-[3-(4-carbamimidoyl-phenyl)-2-cyclohexyl-propionylamino]-cyclohexyl-acetic acid (less polar diastereomer, example 1 h), 2-(S)-amino-5-guanidino-pentanoic acid ethyl ester dihydrochloride, HATU, and collidine in dimethylformamide as described in example 3 to yield 60% of the desired product. MS m/z: 598.5 ((M+H)$^+$, 2%), 299.9 ((M+2H)$^{2+}$, 100%).

Example 6

2-(S)-{2-(S)-[3-(4-Carbamimidoyl-phenyl)-2-cyclohexyl-propionylamino]-2-cyclohexyl-acetylamino}-5-guanidino-pentanoic acid hydrochloric acid salt, less polar diastereomer 2-(S)-{2(S)-[3-(4-Carbamimidoyl-phenyl)-2-cyclohexyl-propionylamino]-2-cyclohexyl-acetylamino}-5-guanidino-pentanoic acid ethyl ester hydrochloric acid salt (6 mg, 8.07 µmol, less polar diastereomer, example 5) was solved in 4 N hydrochloric acid (1 ml) and stirred for 4 hours at room temperature. Water was added and the reaction mixture lyophilized to give 5 mg (quantitative yield) of the desired product. MS m/z: 570.5 ((M+H)$^+$, 1%), 285.9 ((M+2H)$^{2+}$, 100%).

Example 7

3-(4-Carbamimidoyl-phenyl)-2-cyclohexyl-N-{(S)-cyclohexyl-[2-(2,5-dioxo-imidazolidin-1-yl)-ethylcarbamoyl]methyl}-propionamide hydrochloric acid salt, less polar diastereomer 3-(4-Carbamimidoyl-phenyl)-2-cyclohexyl-N-{(S)-cyclohexyl-[2-(2,5-dioxo-imidazolidin-1-yl)-ethylcarbamoyl]-methyl}-propionamide hydrochloric acid salt, less polar diastereomer, was prepared from (S)-[3-(4-carbamimidoyl-phenyl)-2-cyclohexyl-propionylamino]-cyclohexyl-acetic acid (less polar diastereomer, (less polar diastereomer, example 1 h), 3-(2-amino-ethyl)=imidazolidine-2,4-dione hydrochloride, HATU, and collidine in dimethylformamide as described in example 3 to yield 4% of the desired product. MS m/z: 539.5 (M+H)$^+$.

Example 8

3-(4-Carbamimidoyl-phenyl)-2-cyclohexyl-N-{(S)-cyclohexyl-[(piperidin-4-ylmethyl)-carbamoyl]-methyl}-propionamide acetic acid salt, less polar diastereomer To (S)-[3-(4-carbamimidoyl-phenyl)-2-cyclohexyl-propionylamino]-cyclohexyl-acetic acid (50 mg, 0.12 mmol, less polar diastereomer, example 1 h) and 4-aminoethyl-piperidine-1-carboxylic acid tert-butyl ester (26 mg, 0.12 mmol) in dimethylformamide (5 ml) were added HATU (50 mg, 0.13 mmol) and collidine (16 mg, 0.13 mmol) at 0° C. The mixture was stirred for 1 hour and then allowed to warm to room temperature. The mixture was evaporated and treated with 2 ml of trifluoroacetic acid (containing 10% water) for 2 hours. After evaporation, the residue was purified by chromatography on Sephadex LH20 employing n-butanol (17): glacial acetic acid (1): water (2) as eluent. Pure fractions were combined. The solvent was evaporated, the residue was taken up in water, and the aqueous solution was lyophilized. Yield: 45 mg (59%), MS m/z: 510.5 (M+H)$^+$, 255.8 (M+2H)$^{2+}$.

Example 9

General method for synthesis of arylalkanoyl derivatives on solid phase

General solid-phase peptide synthesis was used to produce many of the compounds of this invention. Such methods were described, for example, by Steward and Young (Solid Phase Peptide Synthesis (Freeman and Co., San Francisco, 1969), which is incorporated herein by reference.

Unless indicated otherwise, compounds were synthesized on polystyrene resin cross-linked with 1% divinylbenzene. An acid sensitive linker (Rink Linker) was coupled to the solid support. See, Rink, Tetr. Lett. 28:3787 (1987) and Sieber, Tetr. Lett. 28:2107 (1987); each of which is incorporated herein by reference. All compounds were synthesized on a semi-automated peptide synthesizer built in-house. Boc-and Fmoc-protected L- and D-amino acid derivatives were from various commercial sources like Advanced Chem Tech (Louisville, Ky. 40228-9973, USA); Bachem (King of Prussia, Pa. 19406, USA) and PerSeptive Biosystems (Framington, Mass. 01701, USA). Synthesis of the compounds of formula (I) was carried out according to the classical Fmoc methodology (E. Atherton and R. C. Sheppard in "Solid Phase Peptide Synthesis: A Practical Approach", IRL Press, Oxford, England, 1989) using DICI and HOBt as activating reagents. All couplings were done in dimethylformamide or dimethylformamide:dichloromethane (1:1 mixture) at room temperature for 40 min. Completion of coupling was monitored by ninhydrin test as described by Kaiser (Kaiser et al., Anal. Biochem. 34:595 (1970)), which is incorporated herein by reference. A second (double) coupling was performed where coupling in the first instance was incomplete.

After completion of peptide assembly on the resin, the final Fmoc deprotection was performed, followed by normal wash cycles and determination of the amount of Fmoc group released by deprotection at 302 nm. Then the acetic acid derivatives were similarly coupled by DICI/HOBt procedure. The finished resin was washed successively with dichloromethane, dimethylformamide, and dichloromethane, then dried under vacuum and used in the next step.

Solid-Phase Synthesis of Amidoxime:

The general procedure was by mixing the resin (from the step above) of the nitrile containing substance with 20–40 equivalents of hydroxylamine hydrochloride in presence of 1:1:1 (by volumes) mixture of triethylamine, pyridine, and dimethylformamide. The suspension was usually sonnicated for about 30 sec. and shaked at room temperature for 12–24 hours. The completion of conversion of nitrile to amidoxime was monitored by either FT-IR (KBr disk) looking for the disappearance of —CN absorption at 2225 cm$^{-1}$ or by cleavage of a small sample of the resin by trifluoroacetic acid: $H_2O$ (95:5) or reagent K (see below) and determination of the molecular weight by HPLC/ESMS. The finished resin was washed with dimethylformamide, 10% $H_2O$ in dimethylformamide, ethanol, dichloromethane and dried in vacuum before its use in the next step.

Solid-Phase Synthesis of Amidine:

Several methods were reported for the synthesis of amidine-containing compounds (for review see P. J. Dunn (1995) in "Comprehensive Organic Functional Group Transformation: Amidines and N-Substituted Amidines", Vol. 5, 741–782 (edts. Alan R. Katritzky, Otto Meth-Cohen & Charles W. Rees), Pergamon, N.Y. 1995). None of these methods were compatible with the solid-phase organic synthesis. Here, we developed the proper procedure of amidine synthesis via amidoxime precursor by reduction using excess triethylsilane in the presence of soluble catalyst DCRu. It was found that addition of triphenylphosphine in the presence of acetic acid facilitated the reduction and enhanced the yield of amidine compounds. Thus, the current invention also relates to a process for the reduction of an amidoxime group on solid phase to an amidino group using excess triethylsilane in presence of the soluble catalyst dichlorotetrakis (triphenylphosphine) ruthenium (II) and optionally further in the presence of triphenylphosphin and acetic acid in a solvent, for example dimethylformamide.

In a typical experiment, the dried resin was added to the reduction coctail composed of DCRu, triphenylphosphine, acetic acid, dimethylformamide, and triethylsilane in a stoppered reaction vessel. The reduction typically took 12–24 hours at room temperature. An additional amount of triethylsilan was used in case of incomplete reduction, and the time of reaction was extended by 4–8 additional hours. The finished peptidomimetic resin was washed with dimethylformamide, ethanol, dichloromethane and suspended in a reagent K (King et al., Int. J. Pept. Prot. Res. 36:255–266 (1990)) cocktail (5 ml/g peptide resin) for 180 min at room temperature. Then, the cleavage mixture was filtered in anhydrous diethyl ether, and the solid precipitate was isolated by centrifugation and dried in vacuum over solid pellets of KOH. Then, the solid material was dissolved in a mixture of 1:1 of 0.1% trifluoroacetic acid in water and acetonitrile and then lyophilized.

For peptidomimetic purification, a sample of crude lyophilized compound was dissolved in a mixture of 0.1% aqueous trifluoroacetic acid containing 10% to 50% acetonitrile. The compound solution was typically filtered through a syringe connected to a 0.45 $\mu$m nylon "ACRODISC" 13 (Gelman Sciences; Ann Arbor Mich.) filter. A proper volume of filtered peptidomimetic solution was injected into a semi-preparative $C_{18}$ column (Vydac Protein and Peptide C18, 218TP1010; The Separation Group; Hesperia Calif.). The flow rate of a gradient of isocratic mixture of 0.1% trifluoroactic acid buffer and acetonitrile (HPLC grade) as an eluent was maintained using a Beckman "System Gold" HPLC. Elution of the peptidomimetic was monitored by UV detection at 230 nm (Beckman, System Gold, Programmable Solvent Module 126 and Programmable Detector Module 166 controlled by "SYSTEM GOLD" software). After identifying the peak corresponding to each diastereomer using MS, the compounds were collected, lyophilised and biologically tested. MS was performed using a SCIEX API III+ instrument. In addition, NMR was performed using a General Electric instrument (300 MHz) or Bruker Avance DPX 300 (300 MHz). For NMR, samples typically were measured in DMSO-$d_6$ or $CDCl_3$ (Aldrich). Typical synthesis of individual compounds is summarized in Scheme 5 and the following example illustrate the experimental details.

Example 10

2-(S)-{2-(S)-[3-(4-Carbamimidoyl-phenyl)-2-(R,S)-pyridin-3-yl-propionylamino]-2-cyclohexyl-acetylamino}-5-guanidino-pentanoic acid amide trifluoroactic acid salt a) 3-(4-Cyano-phenyl)-N-[(S)-cyclohexyl-(1-(S)-{carbonylamino-(Rink-resin)}-4-guanidino-butylcarbamoyl)-methyl]-2-(R,S)-pyridin-3-yl-propionamide Fmoc-deprotected Rink resin was coupled to 2-(S)-(Fmoc-amino)-4-(N,N'-bis-tert-butoxycarbonyl-guanidino)-butyric acid (2 eq.) using HOBt and DICI (2eq. of each) as outlined in example 9. After Fmoc-deprotection, the resin was coupled with (S)-cyclohexyl-(Fmoc-amino)-acetic acid (2 eq.) using the same coupling conditions. After Fmoc deprotection, the dried resin (100 mg, subs. 0.65 mmol/g) was coupled with 3-(4-cyano-phenyl)-2-(R,S)-pyridin-3-yl-propionic acid (1.5 eq.) using DICI/HOBt (1.1 eq. each) in dimethformamide for 4 hours at room temperature. The completion of the reaction was confirmed by ninhydrin test. The resin was washed with dimethylformamide, methanol and dichloromethane and dried in vacuo for 2–3 hours.

b) N-[(S)-Cyclohexyl-(1-(S)-{carbonylamino-(Rink-resin)}]- 4-guanidino-butylcarbamoyl)-methyl]-3-[4-(N-hydroxycarbamimidoyl)-phenyl]-2-(R,S)-pyridin-3-yl-propionamide The dried resin from step a was transferred into a screw-capped 20 ml vial and mixed with hydroxylamine hydrochloride (25 eq.). To the reaction vial was added a mixture of triethylamine, pyridine, and dimethylformamide (1:1:1), and the vial was capped and sonicated for 30 sec. The reaction was rocked at room temperature over night. The completion of the reaction was checked as mentioned in example 9. The finished resin was used in the next step.

c) 2-(S)-{2-(S)-[3-(4-Carbamimidoyl-phenyl)-2-(R,S)-pyridin-3-yl-propionyl-amino]-2-cyclohexyl-acetylamino}-5-guanidino-pentanoic acid amide trifluoroacetic acid salt A solution of DCRu and triphenylphosphine in dimethylformamide and glacial acetic acid was heated at 50° C. for 10–15 min to give a clear brown-colored solution. The reaction vial was cooled to room temperature and the second portion of the dried resin from the step above was added following by triethylsilane. The vial was capped under $N_2$ and shaked at room temperature for 12 hours. Completion of reduction to amidine was monitored by cleaving a small amount of the resin and testing the product with HPLC/ESMS. The finished resin was washed with dimethylformamide, methanol, dichloromethane, and processed as outlined in example 9. The final compound was analyzed by MS to give M.Wt. 563.3 (cal. 563.7).

The following compounds were synthesized using the procedures described above:

| Example | Name | MS | Method |
|---|---|---|---|
| 11 | 2-(S)-{3-(4-Amino-phenyl)-2-(S)-[3-(4-carbamimidoyl-phenyl)-2-(R,S)-phenyl-propionylamino]-propionylamino}-5-guanidino-pentanoic acid amide trifluoroacetic acid salt | ok | Solid ph. |
| 12 | 2-(S)-{3-(4-Amino-phenyl)-2-(S)-[3-(4-carbamimidoyl-phenyl)-2-(R,S)-cyclo-hexyl-propionylamino]-propionylamino}-5-guanidino-pentanoic acid amide trifluoroacetic acid salt | ok | Solid ph. |
| 13 | 2-(S)-{3-(4-Amino-phenyl)-2-(S)-[3-(4-carbamimidoyl-phenyl)-2-(R,S)-naphthalen-2-yl-propionylamino]-propionylamino}-5-guanidino-pentanoic acid amide trifluoroacetic acid salt | ok | Solid ph. |
| 14 | 2-(S)-{3-(4-Amino-phenyl)-2-(S)-[3-(4-carbamimidoyl-phenyl)-2-(R,S)-methyl-2-phenyl-propionylamino]-propionylamino}-5-guanidino-pentanoic acid amide trifluoroacetic acid salt | ok | Solid ph. |
| 15 | 2-(S)-{3-(4-Amino-phenyl)-2-(S)-[3-(4-carbamimidoyl-phenyl)-2-(R,S)-pyridin-3-yl-propionylamino]-propionylamino}-5-guanidino-pentanoic acid amide trifluoroacetic acid salt | ok | Solid ph. |
| 16 | 2-(S)-{[3-(4-Carbamimidoyl-phenyl)-2-(R,S)-phenyl-propionyl]-methyl-amino}-3-methyl-pentanoic acid (1-(S)-carbamoyl-4-guanidino-butyl)-amide trifluoroacetic acid salt | ok | Solid ph. |
| 17 | 2-(S)-{[3-(4-Carbamimidoyl-phenyl)-2-(R,S)-naphthalen-2-yl-propionyl]-methyl-amino}-3-methyl-pentanoic acid (1-(S)-carbamoyl-4-guanidino-butyl)-amide trifluoroacetic acid salt | ok | Solid ph. |
| 18 | 2-(S)-{[3-(4-Carbamimidoyl-phenyl)-2-(R,S)-pyridin-3-yl-propionyl]-methyl-amino}-3-methyl-pentanoic acid (1-(S)-carbamoyl-4-guanidino-butyl)-amide trifluoroacetic acid salt | ok | Solid ph. |
| 19 | 2-(S)-[3-(4-Carbamimidoyl-phenyl)-2-(R,S)-phenyl-propionylamino]-hexanoic acid (1-(S)-carbamoyl-4-guanidino-butyl)-amide trifluoroacetic acid salt | ok | Solid ph. |
| 20 | 2-(S)-[3-(4-Carbamimidoyl-phenyl)-2-(R,S)-cyclohexyl-propionylamino]-hexanoic acid (1-(S)-carbamoyl-4-guanidino-butyl)-amide trifluoroacetic acid salt | ok | Solid ph. |
| 21 | 2-(S)-[3-(4-Carbamimidoyl-phenyl)-2-(R,S)-naphthalen-2-yl-propionylamino]-hexanoic acid (1-(S)-carbamoyl-4-guanidino-butyl)-amide trifluoroacetic acid salt | ok | Solid ph. |
| 22 | 2-(S)-[3-(4-Carbamimidoyl-phenyl)-2-(R,S)-methyl-2-phenyl-propionylamino]-hexanoic acid (1-(S)-carbamoyl-4-guanidino-butyl)-amide trifluoroacetic acid salt | ok | Solid ph. |
| 23 | 2-(S)-[3-(4-Carbamimidoyl-phenyl)-2-(R,S)-pyridin-3-yl-propionylamino]-hexanoic acid (1-(S)-carbamoyl-4-guanidino-butyl)-amide trifluoroacetic acid salt | ok | Solid ph. |
| 24 | 2-(S)-(2-(S)-{[3-(4-Carbamimidoyl-phenyl)-2-(R,S)-phenyl-propionyl]-methyl-amino}-3-phenyl-propionylamino)-5-guanidino-pentanoic acid amide trifluoroacetic acid salt | ok | Solid ph. |
| 25 | 2-(S)-(2-(S)-{[3-(4-Carbamimidoyl-phenyl)-2-(R,S)-naphthalen-2-yl-propionyl]-methyl-amino}-3-phenyl-propionylamino)-5-guanidino-pentanoic acid amide trifluoroacetic acid salt | ok | Solid ph. |
| 26 | 2-(S)-(2-(S)-{[3-(4-Carbamimidoyl-phenyl)-2-(R,S)-pyridin-3-yl-propionyl]-methyl-amino}-3-phenyl-propionylamino)-5-guanidino-pentanoic acid amide trifluoroacetic acid salt | ok | Solid ph. |
| 27 | 2-[3-(4-Carbamimidoyl-phenyl)-2-(R,S)-phenyl-propionyl]-1,2,3,4-tetrahydro-isoquinoline-3-(S)-carboxylic acid (1-(S)- | ok | Solid ph. |

-continued

| Example | Name | MS | Method |
|---|---|---|---|
| | carbamoyl-4-guanidino-butyl)-amide trifluoroacetic acid salt | | |
| 28 | 2-[3-(4-Carbamimidoyl-phenyl)-2-(R,S)-cyclohexyl-propionyl]-1,2,3,4-tetra-hydro-isoquinoline-3-(S)-carboxylic acid (1-(S)-carbamoyl-4-guanidino-butyl)-amide trifluoroacetic acid salt | ok | Solid ph. |
| 29 | 2-[3-(4-Carbamimidoyl-phenyl)-2-(R,S)-naphthalen-2-yl-propionyl]-1,2,3,4-tetrahydro-isoquinoline-3-(S)-carboxylic acid (1-(S)-carbamoyl-4-guanidino-butyl)-amide trifluoroacetic acid salt | ok | Solid ph. |
| 30 | 2-[3-(4-Carbamimidoyl-phenyl)-2-(R,S)-methyl-2-phenyl-propionyl]-1,2,3,4-tetrahydro-isoquinoline-3-(S)-carboxylic acid (1-(S)-carbamoyl-4-guanidino-butyl)-amide trifluoroacetic acid salt | ok | Solid ph. |
| 31 | 2-[3-(4-Carbamimidoyl-phenyl)-2-(R,S)-pyridin-3-yl-propionyl]-1,2,3,4-tetra-hydro-isoquinoline-3-(S)-carboxylic acid (1-(S)-carbamoyl-4-guanidino-butyl)-amide trifluoroacetic acid salt | ok | Solid ph. |
| 32 | 4-(S)-[3-(4-Carbamimidoyl-phenyl)-2-(R,S)-phenyl-propionylamino]-4-(1-(S)-carbamoyl-4-guanidino-butylcarbamoyl)-butyric acid trifluoroacetic acid salt | ok | Solid ph. |
| 33 | 4-(S)-[3-(4-Carbamimidoyl-phenyl)-2-(R,S)-cyclohexyl-propionylamino]-4-(1-(S)-carbamoyl-4-guanidino-butylcarbamoyl)-butyric acid trifluoroacetic acid salt | ok | Solid ph. |
| 34 | 4-(S)-[3-(4-Carbamimidoyl-phenyl)-2-(R,S)-naphthalen-2-yl-propionylamino]-4-(1-carbamoyl-4-guanidino-butylcarbamoyl)-butyric acid trifluoroacetic acid salt | ok | Solid ph. |
| 35 | 4-(S)-[3-(4-Carbamimidoyl-phenyl)-2-(R,S)-methyl-2-phenyl-propionylamino]-4-(1-(S)-carbamoyl-4-guanidino-butylcarbamoyl)-butyric acid trifluoroacetic acid salt | ok | Solid ph. |
| 36 | 4-(S)-[3-(4-Carbamimidoyl-phenyl)-2-(R,S)-pyridin-3-yl-propionylamino]-4-(1-(S)-carbamoyl-4-guanidino-butylcarbamoyl)-butyric acid trifluoroacetic acid salt | ok | Solid ph. |
| 37 | 2-(S)-{2-(S)-[3-(4-Carbamimidoyl-phenyl)-2-(R,S)-phenyl-propionylamino]-3-naphthalen-2-yl-propionylamino}-5-guanidino-pentanoic acid amide trifluoroacetic acid salt | ok | Solid ph. |
| 38 | 2-(S)-{2-(S)-[3-(4-Carbamimidoyl-phenyl-2-(R,S)-cyclohexyl-propionyl-amino]-3-naphthalen-2-yl-propionylamino}-5-guanidino-pentanoic acid amide trifluoroacetic acid salt | ok | Solid ph. |
| 39 | 2-(S)-{2-(S)-[3-(4-Carbamimidoyl-phenyl)-2-(R,S)-naphthalen-2-yl-propionyl-amino]-3-naphthalen-2-yl-propionylamino}-5-guanidino-pentanoic acid amide trifluoroacetic acid salt | ok | Solid ph. |
| 40 | 2-(S)-{2-(S)-[3-(4-Carbamimidoyl-phenyl)-2-(R,S)-methyl-2-phenyl-propionyl-amino]-3-naphthalen-2-yl-propionylamino}-5-guanidino-pentanoic acid amide trifluoroacetic acid salt | ok | Solid ph. |
| 41 | 2-(S)-{2-(S)-[3-(4-Carbamimidoyl-phenyl)-2-(R,S)-pyridin-3-yl-propionyl-amino]-3-naphthalen-2-yl-propionylamino}-5-guanidino-pentanoic acid amide trifluoroacetic acid salt | ok | Solid ph. |
| 42 | 2-(S)-{2-(S)-[3-(4-Carbamimidoyl-phenyl)-2-(R,S)-phenyl-propionylamino]-4-phenyl-butyrylamino}-5-guanidino-pentanoic acid amide trifluoroacetic acid salt | ok | Solid ph. |
| 43 | 2-(S)-{2-(S)-[3-(4-Carbamimidoyl-phenyl)-2-(R,S)-cyclohexyl-propionyl-amino]-4-phenyl-butyrylamino}-5-guanidino-pentanoic acid amide trifluoroacetic acid salt | ok | Solid ph. |
| 44 | 2-(S)-{2-(S)-[3-(4-Carbamimidoyl-phenyl)-2-(R,S)-naphthalen-2-yl-propionyl-amino]-4-phenyl-butyrylamino}-5-guanidino-pentanoic acid amide trifluoroacetic acid salt | ok | Solid ph. |
| 45 | 2-(S)-{2-(S)-[3-(4-Carbamimidoyl-phenyl)-2-(R,S)-methyl-2-phenyl-propionyl-amino]-4-phenyl-butyrylamino}-5-guanidino-pentanoic acid amide trifluoroacetic acid salt | ok | Solid ph. |
| 46 | 2-(S)-{2-(S)-[3-(4-Carbamimidoyl-phenyl)-2-(R,S)-pyridin-3-yl-propionyl-amino]-4-phenyl-butyrylamino}-5-guanidino-pentanoic acid amide trifluoroacetic acid salt | ok | Solid ph. |
| 47 | 2-(S)-{5-Amino-2-(S)-[3-(4-carbamimidoyl-phenyl)-2-(R,S)-phenyl-propionyl-amino]-pentanoylamino}-5-guanidino-pentanoic acid amide trifluoroacetic acid salt | ok | Solid ph. |
| 48 | 2-(S)-{5-Amino-2-(S)-[3-(4-carbamimidoyl-phenyl)-2-(R,S)-cyclohexyl-propionylamino]-pentanoylamino}-5-guanidino-pentanoic acid amide trifluoroacetic acid salt | ok | Solid ph. |
| 49 | 2-(S)-{5-Amino-2-(S)-[3-(4-carbamimidoyl-phenyl)-2-(R,S)-naphthalen-2-yl-propionylamino]-pentanoylamino}-5-guanidino-pentanoic acid amide trifluoroacetic acid salt | ok | Solid ph. |
| 50 | 2-(S)-{5-Amino-2-(S)-[3-(4-carbamimidoyl-phenyl)-2-(R,S)-methyl-2-phenyl-propionylamino]-pentanoylamino}-5-guanidino-pentanoic acid amide trifluoroacetic acid salt | ok | Solid ph. |

-continued

| Example | Name | MS | Method |
|---|---|---|---|
| 51 | 2-(S)-{5-Amino-2-(S)-[3-(4-carbamimidoyl-phenyl)-2-(R,S)-pyridin-3-yl-propionylamino]-pentanoylamino}-5-guanidino-pentanoic acid amide trifluoroacetic acid salt | ok | Solid ph. |
| 52 | 3-(S)-[3-(4-Carbamimidoyl-phenyl)-2-(R,S)-phenyl-propionylamino]-N-(1-(S)-carbamoyl-4-guanidino-butyl)-succinamic acid trifluoroacetic acid salt | ok | Solid ph. |
| 53 | 3-(S)-[3-(4-Carbamimidoyl-phenyl)-2-(R,S)-cyclohexyl-propionylamino]-N-(1-(S)-carbamoyl-4-guanidino-butyl)-succinamic acid trifluoroacetic acid salt | ok | Solid ph. |
| 54 | 3-(S)-[3-(4-Carbamimidoyl-phenyl)-2-(R,S)-naphthalen-2-yl-propionylamino]-N-(1-(S)-carbamoyl-4-guanidino-butyl)-succinamic acid trifluoroacetic acid salt | ok | Solid ph. |
| 55 | 3-(S)-[3-(4-Carbamimidoyl-phenyl)-2-(R,S)-methyl-2-phenyl-propionylamino]-N-(1-(S)-carbamoyl-4-guanidino-butyl)-succinamic acid trifluoroacetic acid salt | ok | Solid ph. |
| 56 | 3-(S)-[3-(4-Carbamimidoyl-phenyl)-2-(R,S)-pyridin-3-yl-propionylamino]-N-(1-(S)-carbamoyl-4-guanidino-butyl)-succinamic acid trifluoroacetic acid salt | ok | Solid ph. |
| 57 | 2-(S)-{2-(S)-[3-(4-Carbamimidoyl-phenyl)-2-(R,S)-phenyl-propionylamino]-3-hydroxy-propionylamino}-5-guanidino-pentanoic acid amide trifluoroacetic acid salt | ok | Solid ph. |
| 58 | 2-(S)-{2-(S)-[3-(4-Carbamimidoyl-phenyl)-2-(R,S)-cyclohexyl-propionyl-amino]-3-hydroxy-propionylamino}-5-guanidino-pentanoic acid amide trifluoroacetic acid salt | ok | Solid ph. |
| 59 | 2-(S)-{2-(S)-[3-(4-Carbamimidoyl-phenyl)-2-(R,S)-naphthalen-2-yl-propionyl-amino]-3-hydroxy-propionylamino}-5-guanidino-pentanoic acid amide trifluoroacetic acid salt | ok | Solid ph. |
| 60 | 2-(S)-{2-(S)-[3-(4-Carbamimidoyl-phenyl)-2-(R,S)-methyl-2-phenyl-propionyl-amino]-3-hydroxy-propionylamino}-5-guanidino-pentanoic acid amide trifluoroacetic acid salt | ok | Solid ph. |
| 61 | 2-(S)-{2-(S)-[3-(4-Carbamimidoyl-phenyl)-2-(R,S)-pyridin-3-yl-propionyl-amino]-3-hydroxy-propionylamino}-5-guanidino-pentanoic acid amide trifluoroacetic acid salt | ok | Solid ph. |
| 62 | 2-(S)-{2-(S)-[3-(4-Carbamimidoyl-phenyl)-2-(R,S)-phenyl-propionylamino]-2-phenyl-acetylamino}-5-guanidino-pentanoic acid amide trifluoroacetic acid salt | ok | Solid ph. |
| 63 | 2-(S)-{2-(S)-[3-(4-Carbamimidoyl-phenyl)-2-(R,S)-cyclohexyl-propionyl-amino]-2-phenyl-acetylamino}-5-guanidino-pentanoic acid amide trifluoroacetic acid salt | ok | Solid ph. |
| 64 | 2-(S)-{2-(S)-[3-(4-Carbamimidoyl-phenyl)-2-(R,S)-naphthalen-2-yl-propionyl-amino]-2-phenyl-acetylamino}-5-guanidino-pentanoic acid amide trifluoroacetic acid salt | ok | Solid ph. |
| 65 | 2-(S)-{2-(S)-[3-(4-Carbamimidoyl-phenyl)-2-(R,S)-methyl-2-phenyl-propiony-amino]-2-phenyl-acetylamino}-5-guanidino-pentanoic acid amide trifluoroacetic acid salt | ok | Solid ph. |
| 66 | 2-(S)-{2-(S)-[3-(4-Carbamimidoyl-phenyl)-2-(R,S)-pyridin-3-yl-propionyl-amino]-2-phenyl-acetylamino}-5-guanidino-pentanoic acid amide trifluoroacetic acid salt | ok | Solid ph. |
| 67 | 2-(S)-{3-Benzyloxy-2-(S)-[3-(4-carbamimidoyl-phenyl)-2-(R,S)-phenyl-propionylamino]-propionylamino}-5-guanidino-pentanoic acid amide trifluoroacetic acid salt | ok | Solid ph. |
| 68 | 2-(S)-{3-Benzyloxy-2-(S)-[3-(4-carbamimidoyl-phenyl)-2-(R,S)-cyclohexyl-propionylamino]-propionylamino}-5-guanidino-pentanoic acid amide trifluoroacetic acid salt | ok | Solid ph. |
| 69 | 2-(S)-{3-Benzyloxy-2-(S)-[3-(4-carbamimidoyl-phenyl)-2-(R,S)-naphthalen-2-yl-propionylamino]-propionylamino}-5-guanidino-pentanoic acid amide trifluoroacetic acid salt | ok | Solid ph. |
| 70 | 2-(S)-{3-Benzyloxy-2-(S)-[3-(4-carbamimidoyl-phenyl)-2-(R,S)-methyl-2-phenyl-propionylamino]-propionylamino}-5-guanidino-pentanoic acid amide trifluoroacetic acid salt | ok | Solid ph. |
| 71 | 2-(S)-{3-Benzyloxy-2-(S)-[3-(4-carbamimidoyl-phenyl)-2-(R,S)-pyridin-3-yl-propionylamino]-propionylamino}-5-guanidino-pentanoic acid amide trifluoroacetic acid salt | ok | Solid ph. |
| 72 | [5-(S)-[3-(4-Carbamimidoyl-phenyl)-2-(R,S)-phenyl-propionylamino]-5-(1-(S)-carbamoyl-4-guanidino-butylcarbamoyl)-pentyl]-carbamic acid benzyl ester trifluoroacetic acid salt | ok | Solid ph. |
| 73 | [5-(S)-[3-(4-Carbamimidoyl-phenyl)-2-(R,S)-cyclohexyl-propionylamino]-5-(1-(S)-carbamoyl-4-guanidino-butylcarbamoyl)-pentyl]-carbamic acid benzyl ester trifluoroacetic acid salt | ok | Solid ph. |
| 74 | [5-(S)-[3-(4-Carbamimidoyl-phenyl)-2-(R,S)-naphthalen-2-yl-propionylamino]-5-(1-(S)-carbamoyl-4-guanidino-butylcarbamoyl)-pentyl]-carbamic acid benzyl ester trifluoroacetic acid salt | ok | Solid ph. |
| 75 | [5-(S)-[3-(4-Carbamimidoyl-phenyl)-2-(R,S)-methyl-2- | ok | Solid ph. |

-continued

| Example | Name | MS | Method |
|---|---|---|---|
| | phenyl-propionyl-amino]-5-(1-(S)-carbamoyl-4-guanidino-butylcarbamoyl)-pentyl]-carbamic acid benzyl ester trifluoroacetic acid salt | | |
| 76 | [5-(S)-[3-(4-Carbamimidoyl-phenyl)-2-(R,S)-pyridin-3-yl-propionylamino]-5-(1-(S)-carbamoyl-4-guanidino butylcarbamoyl)-pentyl]-carbamic acid benzyl ester trifluoroacetic acid salt | ok | Solid ph. |
| 77 | 2-(S)-{2-(R)-[3-(4-Carbamimidoyl-phenyl)-2-(R,S)-naphthalen-2-yl-propionyl-amino]-hexanoylamino}-5-guanidino-pentanoic acid trifluoroacetic acid salt | ok | Solid ph. |
| 78 | 2-(S)-{2-(S)-[3-(4-Carbamimidoyl-phenyl)-2-(R,S)-naphthalen-2-yl-propionyl-amino]-hexanoylamino}-5-guanidino-pentanoic acid trifluoroacetic acid salt | ok | Solid ph. |
| 79 | 2-(S)-{2-(S)-[3-(4-Carbamimidoyl-phenyl)-2-(R,S)-naphthalen-2-yl-propionyl-amino]-2-cyclohexyl-acetylamino}-5-guanidino-pentanoic acid trifluoroacetic acid salt | ok | Solid ph. |
| 80 | 2-(S)-{2-(S)-[3-(4-Carbamimidoyl-phenyl)-2-(R,S)-naphthalen-2-yl-propionyl-amino]-3-cyclohexyl-propionylamino}-5-guanidino-pentanoic acid trifluoroacetic acid salt | ok | Solid ph. |
| 81 | 4-(S)-[3-(4-Carbamimidoyl-phenyl)-2-(R,S)-phenyl propionylamino]-4-[1-(S)-(1-(S)-carbamoyl-2-cyclohexyl-ethylcarbamoyl)-4-guanidino-butylcarbamoyl]-butyric acid trifluoroacetic acid salt | ok | Solid ph. |
| 82 | 4-(S)-[3-(4-Carbamimidoyl-phenyl)-2-(R,S)-naphthalen-2-yl-propionylamino]-4-[1-(S)-(1-(S)-carbamoyl-2-cyclohexyl-ethylcarbamoyl)-4-guanidino-butylcarbamoyl]-butyric acid trifluoroacetic acid salt | ok | Solid ph. |
| 83 | 4-(S)-[3-(4-Carbamimidoyl-phenyl)-2-(R,S)-cyclohexyl-propionylamino]-4-[1-(S)-(1-(S)-carbamoyl-2-cyclohexyl-ethylcarbamoyl)-4-guanidino-butylcarbamoyl]-butyric acid trifluoroacetic acid salt | ok | Solid ph. |
| 84 | N-{(S)-[(3-Carbamimidoyl-benzyl)-carbamoylmethyl-carbamoyl]-cyclohexyl-methyl}-3-(4-carbamimidoyl-phenyl)-2-(R,S)-cyclohexyl-propionamide trifluoroacetic acid salt | ok | Solid ph. |
| 85 | 4-({2-(S)-[3-(4-Carbamimidoyl-phenyl)-2-phenyl-propionylamino]-2-cyclohexyl-acetylamino}-methyl)-1-methyl-pyridinium trifluoroacetic acid salt, more polar diastereomer | ok | Solid ph. |
| 86 | 4-({2-(S)-[3-(4-Carbamimidoyl-phenyl)-2-phenyl-propionylamino]-2-cyclohexyl-acetylamino}-methyl)-1-methyl-pyridinium trifluoroacetic acid salt, less polar diastereomer | ok | Solid ph. |
| 87 | 2-(S)-{2-(S)-[3-(4-Carbamimidoyl-phenyl)-2-phenyl-propionylamino]-2-cyclohexyl-acetylamino}-5-guanidino-pentanoic acid amide trifluoroacetic acid salt, more polar diastereomer | ok | Solid ph. |
| 88 | 2-(S)-{2-(S)-[3-(4-Carbamimidoyl-phenyl)-2-phenyl-propionylamino]-2-cyclohexyl-acetylamino}-5-guanidino-pentanoic acid amide trifluoroacetic acid salt, less polar diastereomer | ok | class. syn. |
| 89 | 2-(S)-{2-(S)-[3-(4-Carbamimidoyl-phenyl)-2-(R,S)-phenyl-propionylamino]-3,3-dimethyl-butyrylamino}-5-guanidino-pentanoic acid amide bistrifluoroacetate | ok | Solid ph. |
| 90 | 2-(S)-{2-(S)-[3-(4-Carbamimidoyl-phenyl)-2-(R,S)-cyclo-hexyl-propionylamino]-3,3-dimethyl-butyrylamino}-5-guanidino-pentanoic acid amide trifluoroacetic acid salt | ok | Solid ph. |
| 91 | 2-(S)-{2-(S)-[3-(4-Carbamimidoyl-phenyl)-2-(R,S)-naphthalen-2-yl-propionylamino]-3,3-dimethyl-butyrylamino}-5-guanidino-pentanoic acid amide trifluoroacetic acid salt | ok | Solid ph. |
| 92 | 2-(S)-{2-(S)-[3-(4-Carbamimidoyl-phenyl)-2-(R,S)-methyl-2-phenyl-propionylamino]-3,3-dimethyl-butyrylamino}-5-guanidino-pentanoic acid amide trifluoroacetic acid salt | ok | Solid ph. |
| 93 | 2-(S)-{2-(S)-[3-(4-Carbamimidoyl-phenyl)-2-(R,S)-pyridin-3-yl-propionylamino]-3,3-dimethyl-butyrylamino}-5-guanidino-pentanoic acid amide trifluoroacetic acid salt | ok | Solid ph. |
| 94 | 2-(S)-{2-(S)-[3-(4-Carbamimidoyl-phenyl)-2-(R,S)-cyclo-hexyl-propionylamino]-2-cyclohexyl-acetylamino}-5-guanidino-pentanoic acid amide trifluoroacetic acid salt | ok | Solid ph. |
| 95 | 2-(S)-{2-(S)-[3-(4-Carbamimidoyl-phenyl)-2-(R,S)-naphthalen-2-yl-propionylamino]-2-cyclohexyl-acetylamino}-5-guanidino-pentanoic acid amide trifluoroacetic acid salt | ok | Solid ph. |
| 96 | 2-(S)-{2-(S)-[3-(4-Carbamimidoyl-phenyl)-2-(R,S)-methyl-2-phenyl-propionylamino]-2-cyclohexyl-acetylamino}-5- | ok | Solid ph. |

-continued

| Example | Name | MS | Method |
|---|---|---|---|
| | guanidino-pentanoic acid amide trifluoroacetic acid salt | | |
| 97 | 2-(S)-{2-(S)-[3-(4-Carbamimidoyl-phenyl)-2-(R,S)-phenyl-propionylamino]-3-cyclohexyl-propionylamino}-5-guanidino-pentanoic acid amide trifluoroacetic acid salt | ok | Solid ph. |
| 98 | 2-(S)-{2-(S)-[3-(4-Carbamimidoyl-phenyl)-2-(R,S)-cyclo-hexyl-propionylamino]-3-cyclohexyl-propionylamino}-5-guanidino-pentanoic acid amide trifluoroacetic acid salt | ok | Solid ph. |
| 99 | 2-(S)-{2-(S)-[3-(4-Carbamimidoyl-phenyl)-2-(R,S)-naphthalen-2-yl-propionylamino]-3-cyclohexyl-propionyl-amino}-5-guanidino-pentanoic acid amide trifluoroacetic acid salt | ok | Solid ph. |
| 100 | 2-(S)-{2-(S)-[3-(4-Carbamimidoyl-phenyl)-2-(R,S)-methyl-2-phenyl-propionylamino]-3-cyclohexyl-propionylamino}-5-guanidino-pentanoic acid amide trifluoroacetic acid salt | ok | Solid ph. |
| 101 | 2-(S)-{2-(S)-[3-(4-Carbamimidoyl-phenyl)-2-(R,S)-pyridin-3-yl-propionylamino]-3-cyclohexyl-propionylamino}-5-guanidino-pentanoic acid amide trifluoroacetic acid salt | ok | Solid ph. |
| 102 | 2-(S)-{2-(S)-[3-(4-Carbamimidoyl-phenyl)-2-(R,S)-phenyl-propionylamino]-3-phenyl-propionylamino}-5-guanidino-pentanoic acid amide trifluoroacetic acid salt | ok | Solid ph. |
| 103 | 2-(S)-{2-(S)-[3-(4-Carbamimidoyl-phenyl)-2-(R,S)-cyclo-hexyl-propionylamino]-3-phenyl-propionylamino}-5-guanidino-pentanoic acid amide trifluoroacetic acid salt | ok | Solid ph. |
| 104 | 2-(S)-{2-(S)-[3-(4-Carbamimidoyl-phenyl)-2-(R,S)-naphthalen-2-yl-propionylamino]-3-phenyl-propionylamino}-5-guanidino-pentanoic acid amide trifluoroacetic acid salt | ok | Solid ph. |
| 105 | 2-(S)-{2-(S)-[3-(4-Carbamimidoyl-phenyl)-2-(R,S)-methyl-2-phenyl-propionylamino]-3-phenyl-propionylamino}-5-guanidino-pentanoic acid amide trifluoroacetic acid salt | ok | Solid ph. |
| 106 | 2-(S)-{2-(S)-[3-(4-Carbamimidoyl-phenyl)-2-(R,S)-pyridin-3-yl-propionylamino]-3-phenyl-propionylamino}-5-guanidino-pentanoic acid amide trifluoroacetic acid salt | ok | Solid ph. |
| 107 | 2-(S)-{2-[3-(4-Carbamimidoyl-phenyl)-2-cyclohexyl-propionylamino]-2-cyclohexyl-acetylamino}-5-guanidino-pentanoic acid amide hydrochloric acid salt, more polar diastereomer | ok | class. syn. |
| 108 | 3-(4-Carbamimidoyl-phenyl)-N-[(S)-(4-cyano-benzyl-carbamoyl)-cyclohexyl-methyl]-2-cyclohexyl-propionamide hydrochloric acid salt, less polar diastereomer | ok | class. syn. |
| 109 | 2-(S)-{2-[3-(4-Carbamimidoyl-phenyl)-2-cyclohexyl-propionylamino]-2-cyclohexyl-acetylamino}-5-guanidino-pentanoic acid amide acetic acid salt, less polar diastereomer | ok | class. syn. |
| 110 | 2-(S)-{2-[3-(4-Carbamimidoyl-phenyl)-2-cyclohexyl-propionylamino]-2-cyclohexyl-acetylamino}-5-guanidino-pentanoic acid amide acetic acid salt, least polar diastereomer | ok | class. syn. |
| 111 | N-[(S)-(4-Carbamimidoyl-benzylcarbamoyl)-cyclohexylmethyl]-3-(4-carbamimidoyl-phenyl)-2-cyclohexyl-propionamide hydrochloric acid salt, less polar diastereomer | ok | class. syn. |
| 112 | 2-[3-(4-Carbamimidoyl-phenyl)-2-(R,S)-cyclohexyl-propionyl]-1,2,3,4-tetrahydro-isoquinoline-1-(R,S)-carboxylic acid (1-(S)-carbamoyl-4-guanidino-butyl)-amide hydrochloric acid salt | ok | class. syn. |
| 113 | 3-(4-Carbamimidoyl-phenyl)-N-{(S)-[(1-carbamimidoyl-piperidin-4-ylmethyl)-carbamoyl]-cyclohexyl-methyl}-2-cyclohexyl-propionamide hydrochloric acid salt, less polar diastereomer | ok | class. syn. |
| 114 | 3-(4-Carbamimidoyl-phenyl)-N-{(S)-[(1-carbamimidoyl-piperidin-4-ylmethyl)-carbamoyl]-cyclohexyl-methyl}-2-cyclohexyl-propionamide hydrochloric acid salt, more polar diastereomer | ok | class. syn. |
| 115 | 4-({2-(S)-[3-(4-Carbamimidoyl-phenyl)-2-cyclohexyl-propionylamino]-2-cyclohexyl-acetylamino}-methyl)-benzamide hydrochloric acid salt, less polar diastereomer | ok | class. syn. |
| 116 | 2-(S)-{2-(S)-[3-(4-Aminomethyl-phenyl)-2-cyclohexyl-propionylamino]-2-cyclohexyl-acetylamino}-5-guanidino-pentanoic acid amide hydrochloric acid salt, less polar diastereomer | ok | class syn. |
| 117 | 2-(S)-{2-(S)-[3-(4-Aminomethyl-phenyl)-2-cyclohexyl-propionylamino]-2-cyclohexyl-acetylamino}-5-guanidino-pentanoic acid amide hydrochloric acid salt, more polar diastereomer | ok | class. syn. |
| 118 | 2-(S)-{2-(S)-[3-(4-Carbamoyl-phenyl)-2-(R,S)-(3-trifluoro-methyl-phenyl)-propionylamino]-2-cyclohexyl-acetylamino}-5-guanidino-pentanoic acid ethyl ester hydrochloric acid | ok | class. syn. |

-continued

| Example | Name | MS | Method |
|---|---|---|---|
| | salt | | |
| 119 | 2-(S)-{2-(S)-[2-(4-Bromo-phenyl)-3-(4-carbamimidoyl-phenyl)-propionylamino]-2-cyclohexyl-acetylamino}-5-guanidino-pentanoic acid amide hydrochloric acid salt, less polar diastereomer | ok | class. syn. |
| 120 | 2-(S)-{2-(S)-[2-(4-Bromo-phenyl)-3-(4-carbamimidoyl-phenyl)-propionylamino]-2-cyclohexyl-acetylamino}-5-guanidino-pentanoic acid amide hydrochloric acid salt, less polar diastereomer | ok | class. syn. |
| 121 | 2-(S)-{2-(S)-[3-(4-Carbamimidoyl-phenyl)-2-(S)-m-tolyl-propionylamino]-2-cyclohexyl-acetylamino}-5-guanidino-pentanoic acid amide hydrochloric acid salt more polar diastereomer | ok | class. syn. |
| 122 | 2-(S)-{2-(S)-[3-(4-Carbamimidoyl-phenyl)-2-(R,S)-m-tolyl-propionylamino]-2-cyclohexyl-acetylamino}-5-guanidino-pentanoic acid amide hydrochloric acid salt | ok | class. syn. |
| 123 | 2-(S)-{2-(S)-[3-(4-Carbamimidoyl-phenyl)-2-(R,S)-(3-chloro-phenyl)-propionylamino]-2-cyclohexyl-acetylamino}-5-guanidino-pentanoic acid ethyl ester hydrochloric acid salt | ok | class. syn. |
| 124 | 2-(S)-{2-(S)-[3-(4-Carbamimidoyl-phenyl)-2-(3-chloro-phenyl)-propionylamino]-2-cyclohexyl-acetylamino}-5-guanidino-pentanoic acid amide hydrochloric acid salt, less polar diastereomer | ok | class. syn. |
| 125 | 2-(S)-{2-(S)-[3-(4-Carbamimidoyl-phenyl)-2-(3-chloro-phenyl)-propionylamino]-2-cyclohexyl-acetylamino}-5-guanidino-pentanoic acid amide hydrochloric acid salt, more polar diastereomer | ok | class. syn. |
| 126 | 2-(S)-{2-(S)-[3-(4-Carbamimidoyl-phenyl)-2-(R,S)-(3-fluoro-phenyl)-propionylamino]-2-cyclohexyl-acetylamino}-5-guanidino-pentanoic acid ethyl ester hydrochloric acid salt | ok | class. syn. |
| 127 | 2-(S)-{2-(S)-[2-(R,S)-(3-Bromo-phenyl)-3-(4-carbamimidoyl-phenyl)-propionylamino]-2-cyclohexyl-acetylamino}-5-guanidino-pentanoic acid ethyl ester hydrochloric acid salt | ok | class. syn. |
| 128 | 2-(S)-{2-(S)-[3-(4-Carbamoyl-phenyl)-2-phenyl-propionylamino]-2-cyclohexyl-acetylamino}-5-guanidino-pentanoic acid ethyl ester hydrochloric acid salt, less polar diastereomer | ok | class. syn. |
| 129 | 2-(S)-{2-(S)-[3-(4-Carbamoyl-phenyl)-2-phenyl-propionylamino]-2-cyclohexyl-acetylamino}-5-guanidino-pentanoic acid ethyl ester hydrochloric acid salt, more polar diastereomer | ok | class. syn. |
| 130 | 2-(S)-{2-(S)-[3-(4-Cyano-phenyl)-2-(R,S)-phenyl-propionyl-amino]-2-cyclohexyl-acetylamino}-5-guanidino-pentanoic acid amide hydrochloric acid salt | ok | class. syn. |
| 131 | 2-(S)-{2-(S)-[3-(4-Carbamimidoyl-phenyl)-2-(3-fluoro-phenyl)-propionylamino]-2-cyclohexyl-acetylamino}-5-guanidino-pentanoic acid amide hydrochloric acid salt, less polar diastereomer | ok | class. syn. |
| 132 | 2-(S)-{2-(S)-[3-(4-Carbamimidoyl-phenyl)-2-(3-fluoro-phenyl)-propionylamino]-2-cyclohexyl-acetylamino}-5-guanidino-pentanoic acid amide hydrochloric acid salt, more polar diastereomer | ok | class. syn. |
| 133 | 2-(S)-{2-(S)-[2-(3-Bromo-phenyl)-3-(4-carbamimidoyl-phenyl)-propionylamino]-2-cyclohexyl-acetylamino}-5-guanidino-pentanoic acid amide hydrochloric acid salt, less polar diastereomer | ok | class. syn. |
| 134 | 2-(S)-{2-(S)-[2-(3-Bromo-phenyl)-3-(4-carbamimidoyl-phenyl)-propionylamino]-2-cyclohexyl-acetylamino}-5-guanidino-pentanoic acid amide hydrochloric acid salt, more polar diastereomer | ok | class. syn. |
| 135 | 2-(S)-{2-(S)-[3-(4-Carbamimidoyl-phenyl)-2-(R,S)-phenyl-propionylamino]-2-cyclohexyl-acetylamino}-5-guanidino-pentanoic acid amide hydrochloric acid salt | ok | class. syn. |
| 136 | N-[(S)-(4-Carbamimidoyl-benzylcarbamoyl)-cyclohexyl-methyl]-3-(4-carbamimidoyl-phenyl)-2-(R,S)-phenyl-propionamide acetic acid salt | ok | class. syn. |
| 137 | 3-(4-Carbamimidoyl-phenyl)-2-cyclohexyl-N-((S)-cyclohexyl-{[1-(1-imino-ethyl)-piperidin-4-ylmethyl]-carbamoyl}-methyl)-propionamide acetic acid salt, less polar diastereomer | ok | class. syn. |
| 138 | 3-(4-Aminomethyl-phenyl)-N-[(S)-(4-carbamimidoyl-benzyl-carbamoyl)-cyclohexyl-methyl]-2-(R,S)-cyclohexyl-propionamide acetic acid salt | ok | class. syn. |
| 139 | 2-(S)-{2-(S)-[3-(4-Carbamimidoyl-phenyl)-2-(S)-cyclohexyl-propionylamino]-2-cyclohexyl-acetylamino}-5-guanidino-pentanoic acid ethyl ester hydrochloric acid salt, more polar diastereomer | ok | class. syn. |

-continued

| Example | Name | MS | Method |
|---|---|---|---|
| 140 | 2-(S)-{2-(S)-[3-(4-Carbamimidoyl-phenyl)-2-(R,S)-o-tolyl-propionylamino]-2-cyclohexyl-acetylamino}-5-guanidino-pentanoic acid amide hydrochloric acid salt | ok | class. syn. |
| 141 | 2-(S)-{2-(S)-[3-(4-Carbamimidoyl-phenyl)-2-(R,S)-p-tolyl-propionylamino]-2-cyclohexyl-acetylamino}-5-guanidino-pentanoic acid amide hydrochloric acid salt | ok | class. syn. |
| 142 | 2-(S)-{2-(S)-[3-(4-Carbamimidoyl-phenyl)-2-(R,S)-(1,2,3,4-tetrahydro-naphthalen-1-yl)-propionylamino]-2-cyclohexyl-acetylamino}-5-guanidino-pentanoic acid amide hydrochloric acid salt | ok | class. syn. |
| 143 | 2-(S)-{2-(S)-[3-(4-Carbamimidoyl-phenyl)-2-(R,S)-(1,2,3,4-tetrahydro-naphthalen-2-yl)-propionylamino]-2-cyclohexyl-acetylamino}-5-guanidino-pentanoic acid amide hydrochloric acid salt | ok | class. syn. |
| 144 | 2-(S)-(2-(S)-Cyclohexyl-2-{3-[4-(N-hydroxycarbamimidoyl)-phenyl]-2-(R,S)-m-tolyl-propionylamino}-acetylamino)-5-guanidino-pentanoic acid amide hydrochloric acid salt | ok | class. syn. |
| 145 | 3-(4-Aminomethyl-phenyl)-N-{(S)-[(1-carbamimidoyl-piperidin-4-ylmethyl)-carbamoyl]-cyclohexyl-methyl}-2-(R,S)-cyclohexyl-propionamide hydrochloric acid salt | ok | class. syn. |
| 146 | 2-(R,S)-(3-Bromo-phenyl)-N-{(S)-[(1-carbamimidoyl-piperidin-4-ylmethyl)-carbamoyl]-cyclohexyl-methyl}-3-(4-cyano-phenyl)-propionamide hydrochloric acid salt | ok | class. syn. |
| 147 | N-[(S)-(4-Carbamimidoyl-benzylcarbamoyl)-cyclohexyl-methyl]-3-(4-carbamimidoyl-phenyl)-2-(R,S)-m-tolyl-propionamide hydrochloric acid salt | ok | class. syn. |
| 148 | N-[(S)-(4-Carbamimidoyl-benzylcarbamoyl)-cyclohexyl-methyl]-3-(4-carbamimidoyl-phenyl)-2-(3-fluoro-phenyl)-propionamide hydrochloric acid salt, more polar diastereomer | ok | class. syn. |
| 149 | N-[(S)-(4-Carbamimidoyl-benzylcarbamoyl)-cyclohexyl-methyl]-3-(4-carbamimidoyl-phenyl)-2-(3-fluoro-phenyl)-propionamide hydrochloric acid salt, less polar diastereomer | ok | class. syn. |
| 150 | 2-(3-Bromo-phenyl)-N-[(S)-(4-carbamimidoyl-benzyl-carbamoyl)-cyclohexyl-methyl]-3-(4-carbamimidoyl-phenyl)-propionamide hydrochloric acid salt, more polar diastereomer | ok | class. syn. |
| 151 | 2-(3-Bromo-phenyl)-N-[(S)-(4-carbamimidoyl-benzyl-carbamoyl)-cyclohexyl-methyl]-3-(4-carbamimidoyl-phenyl)-propionamide hydrochloric acid salt, less polar diastereomer | ok | class. syn. |
| 152 | N-[(S)-(4-Carbamimidoyl-benzylcarbamoyl)-cyclohexyl-methyl]-3-(4-carbamimidoyl-phenyl)-2-(R,S)-o-tolyl-propionamide hydrochloric acid salt | ok | class. syn. |
| 153 | N-[(S)-(4-Carbamimidoyl-benzylcarbamoyl)-cyclohexyl-methyl]-3-(4-carbamimidoyl-phenyl)-2-p-tolyl-propionamide hydrochloric acid salt, more polar diastereomer | ok | class. syn. |
| 154 | N-[(S)-(4-Carbamimidoyl-benzylcarbamoyl)-cyclohexyl-methyl]-3-(4-carbamimidoyl-phenyl)-2-p-tolyl-propionamide hydrochloric acid salt, less polar diastereomer | ok | class. syn. |
| 155 | 2-(4-Bromo-phenyl)-N-[(S)-(4-carbamimidoyl-benzyl-carbamoyl)-cyclohexyl-methyl]-3-(4-carbamimidoyl-phenyl)-propionamide hydrochloric acid salt, more polar diastereomer | ok | class. syn. |
| 156 | 2-(4-Bromo-phenyl)-N-[(S)-(4-carbamimidoyl-benzyl-carbamoyl)-cyclohexyl-methyl]-3-(4-carbamimidoyl-phenyl)-propionamide hydrochloric acid salt, less polar diastereomer | ok | class. syn. |
| 157 | N-[(S)-(4-Carbamimidoyl-benzylcarbamoyl)-cyclohexyl-methyl]-3-(4-carbamimidoyl-phenyl)-2-(R,S)-(3-chloro-phenyl)-propionamide hydrochloric acid salt | ok | class. syn. |
| 158 | 3-(4-Carbamimidoyl-phenyl)-N-{(S)-[(1-carbamimidoyl-piperidin-4-ylmethyl)-carbamoyl]-cyclohexyl-methyl}-2-m-tolyl-propionamide hydrochloric acid salt, more polar diastereomer | ok | class. syn. |
| 159 | 3-(4-Carbamimidoyl-phenyl)-N-{(S)-[(1-carbamimidoyl-piperidin-4-ylmethyl)-carbamoyl]-cyclohexyl-methyl}-2-m-tolyl-propionamide hydrochloric acid salt, less polar diastereomer | ok | class. syn. |
| 160 | 3-(4-Carbamimidoyl-phenyl)-N-{(S)-[(1-carbamimidoyl-piperidin-4-ylmethyl)-carbamoyl]-cyclohexyl-methyl}-2-(3-fluoro-phenyl)-propionamide hydrochloric acid salt, more polar diastereomer | ok | class. syn. |
| 161 | 3-(4-Carbamimidoyl-phenyl)-N-{(S)-[(1-carbamimidoyl-piperidin-4-ylmethyl)-carbamoyl]-cyclohexyl-methyl}-2-(3-fluoro-phenyl)-propionamide hydrochloric acid salt, less | ok | class. syn. |

-continued

| Example | Name | MS | Method |
|---|---|---|---|
| | polar diastereomer | | |
| 162 | 3-(4-Carbamimidoyl-phenyl)-N-{(S)-[(1-carbamimidoyl-piperidin-4-ylmethyl)-carbamoyl]-cyclohexyl-methyl}-2-o-tolyl-propionamide hydrochloric acid salt, more polar diastereomer | ok | class. syn. |
| 163 | 3-(4-Carbamimidoyl-phenyl)-N-{(S)-[(1-carbamimidoyl-piperidin-4-ylmethyl)-carbamoyl]-cyclohexyl-methyl}-2-o-tolyl-propionamide hydrochloric acid salt, less polar diastereomer | ok | class. syn. |

Examples 164 and 165

2-(3-Bromo-phenyl)-3-(4-carbamimidoyl-phenyl)-N-{(S)-[(1-carbamimidoyl-piperidin-4-ylmethyl)-carbamoyl]-cyclohexyl-methyl}-propionamide hydrochloric acid salt, more polar diastereomer (164) and 2-(3-Bromo-phenyl)-3-(4-carbamimidoyl-phenyl)-N-{(S)-[(1-carbamimidoyl-piperidin-4-ylmethyl)-carbamoyl]-cyclohexyl-methyl}-propionamide hydrochloric acid salt, less polar diastereomer (165)

a) 2-(3-Bromo-phenyl)-3-(4-cyano-phenyl)-propionic acid

N-Butyllithium (40.33 g, 15% in hexane; 94.4 mmol) was added to tetrahydrofuran (140 ml) at 0° C. under nitrogen with stirring, then 2,2,6,6-tetramethylpiperidine (16 ml, 94.6 mmol) was added. The solution was cooled to −78° C. and stirred for 60 min. (3-Bromo-phenyl)-acetic acid (9.68 g, 45 mmol) in tetrahydrofuran (50 ml) was added dropwise to the solution with stirring. After stirring for 60 min., a solution of 4-cyano-benzyl bromide (8.38 g, 45 mmol) in tetrahydrofuran (50 ml) was added. The reaction mixture was stirred for 2 hours at −78° C., then allowed to warm to room temperature over 20 hours.

Saturated aqueous ammonium chloride solution (200 ml), hydrochoric acid (6 N, 40 ml), and ethyl acetate (200 ml) were added and the organic layer was separated, washed with ammonium chloride solution (3×200 ml) and saturated sodium chloride solution (200 ml), dried (magnesium sulphate), and evaporated. The residue was dissolved in ethyl acetate (200 ml) and extracted with saturated aqueous sodium carbonate solution (2×2000 ml). The aqueous solution was acidified with potassium hydrogen sulphate to pH 3 and the solid filtered, washed with water, and dried. Yield 5.85 g (39%), MS m/z: 330 (M+H)$^+$.

b) 2-(3-Bromo-phenyl)-3-(4-carbamimidoyl-phenyl)-propionic acid hydrochloric acid salt A solution of 2-(Bromo-phenyl)-3-(4-cyano-phenyl)-propionic acid (4.5 g, 13.6 mmol) in ethanol (100 ml) was saturated with dry hydrochloric acid at −20° C. to −40° C. for 2 hours. The mixture was allowed to warm to room temperature and stirred for 20 hours. Nitrogen was bubbled through the solution for 3 hours and the solution was evaporated at 20° C. The residue was dissolved in dimethylformamide (50 ml) and saturated with dry ammonia for 2 hours. The solution was evaporated after 20 hours and treated with ethyl acetate and ethanol. The solid ammonium chloride was filtered and the solution evaporated, and treated again with ethyl acetate. The oily residue was separated to yield the ethyl ester hydrochloride of 2-(3-bromo-phenyl)-3-(4-carbamimidoyl-phenyl)-propionic acid. The ester was dissolved in hydrochloric acid (6 N, 20 ml) and acetic acid (20 ml) and stirred for 20 hours at room temperature and 48 hours at 50° C. The solution was evaporated and lyophylized to yield 3.7 g (75%) of the desired product. MS m/z 347 (M+H)$^+$.

c) {[(1-Carbamimidoyl-piperidin-4-ylmethyl)-carbamoyl]-(S)-cyclohexyl-methyl}-carbamic acid tert-butyl ester hydrochloric acid salt To (S)-tert-butoxycarbonylamino-cyclohexyl-acetic acid (1.8 g, 7 mmol) in dimethylformamide (100 ml) were added HATU (2.9 g, 7.7 mmol) and collidine (0.93 ml, 7 mmol) at 0° C. The mixture was stirred for 20 min. and 4-aminomethyl-piperidine-1-carboxyamidine hydrochloric acid salt (1.6 g, 7 mmol) and collidine (1.85 ml, 14 mmol) were added. The mixture was stirred for 1 hour then allowed to warm to room temperature. After evaporation, the residue was treated with ethyl acetate and sodium hydrogen sulfate solution and the organic layer was separated, dried, and evaporated to yield 3.65 g of product still containing collidine salt.

d) 2-Amino-N-(1-carbamimidoyl-piperidin-4-ylmethyl)-2-(S)-cyclohexyl-acetamide hydrochloric acid salt {[(1-Carbamimidoyl-piperidine-4-ylmethyl)-carbamoyl]-(S)-cyclohexyl-methyl}-carbamic acid tert butyl ester hydrochloric acid salt (3.64 g crude material) was stirred with aqueous trifluoroacetic acid (90%) at room temperature for 20 hours, evaporated, dissolved in aqueous hydrochloric acid and lyophilized to yield 2.69 g (89%) of the desired product, MS m/z: 296 (M+H)$^+$, 148 (M+2H)$^{2+}$.

e) 2-(3-Bromo-phenyl)-3-(4-carbamimidoyl-phenyl)-N-{[(1-carbamimidoyl-piperidin-4-ylmethyl)-carbamoyl]-(S)-cyclohexyl-methyl}-propionamide hydrochloric acid salt To 2-(3-bromo-phenyl)-3-(4-carbamimidoyl-phenyl)-propionic acid hydrochloride (188 mg, 0.49 mmol) in dimethylformamide (30 ml) was added TOTU (164 mg, 0.5 mmol) and N-ethylmorpholine (127 μl, 1 mmol) at 0° C. The mixture was stirred for 30 min at 0° C., 2-amino-N-(1-carbamimidoyl-piperidin-4-ylmethyl)-2-(S)-cyclohexyl-acetamide hydrochloric acid salt (180 mg, 0.49 mmol) was added and the mixture was then allowed to warm to room temperature. After evaporation, the residue was purified by chromotography on Sephadex LH20 employing n-butanol (17): glacial acetic acid (1): water (2) as eluent. Pure fractions were combined. The solvent was evaporated, the residue was taken up in water and hydrochloric acid and lyophilized. Yield: 82 mg of the more polar diastereomer and 71 mg of the less polar diastereomer, MS (FAB) m/z: 624 (M+H)$^+$.

The following compounds were synthesized using the procedures described in examples 1 to 10 and 164 and 165.

| | | | |
|---|---|---|---|
| 166 | 3-(4-Amino-phenyl)-N-{(S)-[(1-carbamimidoyl-piperidin-4-ylmethyl)-carbamoyl]-cyclohexyl-methyl}-2-m-tolyl-propionamide hydrochloric acid salt, more polar diastereomer | ok | class. syn. |
| 167 | 3-(4-Amino-phenyl)-N-{(S)-[(1-carbamimidoyl-piperidin-4-ylmethyl)-carbamoyl]-cyclohexyl-methyl}-2-m-tolyl-propionamide hydrochloric acid salt, less polar diastereomer | ok | class. syn. |
| 168 | N-{(S)-[(1-Carbamimidoyl-piperidin-4-ylmethyl)-carbamoyl]-cyclohexyl-methyl}-3-(4-cyano-phenyl)-2-(R,S)-cyclohexyl-propionamide hydrochloric acid salt | ok | class. syn. |
| 169 | 3-(4-Carbamimidoyl-phenyl)-N-{(S)-[(1-carbamimidoyl-piperidin-4-ylmethyl)-carbamoyl]-cyclohexyl-methyl}-2-naphthalen-2-yl-propionamide hydrochloric acid salt, more polar diastereomer | ok | class. syn. |
| 170 | 3-(4-Carbamimidoyl-phenyl)-N-{(S)-[(1-carbamimidoyl-piperidin-4-ylmethyl)-carbamoyl]-cyclohexyl-methyl}-2-naphthalen-2-yl-propionamide hydrochloric acid salt, less polar diastereomer | ok | class. syn. |
| 171 | 3-(4-Carbamimidoyl-phenyl)-N-{(S)-[(1-carbamimidoyl-piperidin-4-ylmethyl-carbamoyl]-cyclohexyl-methyl}-2-p-tolyl-propionamide hydrochloric acid salt, more polar diastereomer | ok | class. syn. |
| 172 | 3-(4-Carbamimidoyl-phenyl)-N-{(S)-[(1-carbamimidoyl-piperidin-4-ylmethyl)-carbamoyl]-cyclohexyl-methyl}-2-p-tolyl-propionamide hydrochloric acid salt, less polar diastereomer | ok | class. syn. |
| 173 | 3-(4-Aminomethyl-phenyl)-N-[(S)-(4-cyano-benzyl-carbamoyl)-cyclohexyl-methyl]-2-(R,S)-cyclohexyl-propionamide hydrochloric acid salt | ok | class. syn. |
| 174 | 3-(4-Aminomethyl-phenyl)-2-(R,S)-cyclohexyl-N-{(S)-cyclo-hexyl-[4-(N-hydroxycarbamimidoyl)-benzylcarbamoyl]-methyl}-propionamide hydrochloric acid salt | ok | class. syn. |
| 175 | 3-(4-Carbamimidoyl-phenyl)-N-{(S)-[(1-carbamimidoyl-piperidin-4-ylmethyl)-carbamoyl]-cyclohexyl-methyl}-2-(3-chloro-phenyl)-propionamide hydrochloric acid salt, more polar diastereomer | ok | class. syn. |
| 176 | 3-(4-Carbamimidoyl-phenyl)-N-{(S)-[(1-carbamimidoyl-piperidin-4-ylmethyl)carbamoyl]-cyclohexyl-methyl}-2-(3-chloro-phenyl)-propionamide hydrochloric acid salt, less polar diastereomer | ok | class. syn. |
| 177 | 2-(4-Bromo-phenyl)-3-(4-carbamimidoyl-phenyl)-N-{(S)-[(1-carbamimidoyl-piperidin-4-ylmethyl)-carbamoyl]-cyclohexyl-methyl}-propionamide hydrochloric acid salt, less polar diastereomer | ok | class. syn. |
| 178 | 2-(4-Bromo-phenyl)-3-(4-carbamimidoyl-phenyl)-N-{(S)-[(1-carbamimidoyl-piperidin-4-ylmethyl)-carbamoyl]-cyclohexyl-methyl}-propionamide hydrochloric acid salt, more polar diastereomer | ok | class. syn. |
| 179 | 2-{2-[3-(4-Carbamimidoyl-phenyl)-2-cyclohexyl-propionylamino]-2-(S)-cyclohexyl-acetylamino}-5-guanidino-pentanoic acid dimethylamide hydrochloric acid salt, less polar diastereomer | ok | class. syn. |
| 180 | 2-{2-[3-(4-Carbamimidoyl-phenyl)-2-cyclohexyl-propionylamino]-2-(S)-cyclohexyl-acetylamino}-5-guanidino-pentanoic acid dimethylamide hydrochloric acid salt, more polar diastereomer | ok | class. syn. |
| 181 | 2-(S)-{2-[3-(4-Carbamimidoyl-phenyl)-2-(R,S)-cyclohexyl-propionylamino]-2-(S)-cyclohexyl-acetylamino}-5-guanidino-pentanoic acid isopropyl ester hydrochloric acid salt | ok | class. syn. |
| 182 | 2-(S)-{2-[3-(4-Carbamimidoyl-phenyl)-2-cyclohexyl-propionylamino]-2-cyclohexyl-acetylamino}-5-guanidino-pentanoic acid benzyl-methyl-amide trifluoroacetic acid salt, more polar diastereomer | ok | class. syn. |
| 183 | 2-(S)-{2-[3-(4-Carbamimidoyl-phenyl)-2-cyclohexyl-propionylamino]-2-cyclohexyl-acetylamino}-5-guanidino-pentanoic acid benzyl-methyl-amide trifluoroacetic acid salt, less polar diastereomer | ok | class. syn. |
| 184 | 2-(S)-{2-(R,S)-[3-(4-Carbamimidoyl-phenyl)-2-cyclohexyl-propionylamino]-2-(S)-cyclohexyl-acetylamino}-5-guanidino-pentanoic acid phenethyl-amide trifluoroacetic acid salt | ok | class. syn. |
| 185 | 2-(S)-{2-[3-(4-Carbamimidoyl-phenyl)-2-cyclohexyl-propionylamino]-2-(S)-cyclohexyl-acetylamino}-5-guanidino-pentanoic acid isopropyl ester hydrochloric acid salt, more polar diastereomer | ok | class. syn. |
| 186 | 2-(S)-{2-[3-(4-Carbamimidoyl-phenyl)-2-cyclohexyl-propionylamino]-2-(S)-cyclohexyl-acetylamino}-5- | ok | class. syn. |

| | -continued | | |
|---|---|---|---|
| | guanidino-pentanoic acid butyl ester trifluoroacetic acid salt, more polar diastereomer | | |
| 187 | 2-(S)-{2-[3-(4-Carbamimidoyl-phenyl)-2-cyclohexyl-propionylamino]-2-(S)-cyclohexyl-acetylamino}-5-guanidino-pentanoic acid propyl ester trifluoroacetic acid salt, more polar diastereomer | ok | class. syn. |
| 188 | 2-(S)-{2-[3-(4-Carbamimidoyl-phenyl)-2-cyclohexyl-propionylamino]-2-(S)-cyclohexyl-acetylamino}-5-guanidino-pentanoic acid butyl ester trifluoroacetic acid salt, less polar diastereomer | ok | class. syn. |
| 189 | 2-(S)-{2-[3-(4-Carbamimidoyl-phenyl)-2-cyclohexyl-propionylamino]-2-(S)-cyclohexyl-acetylamino}-5-guanidino-pentanoic acid propyl ester, less polar diastereomer | ok | class. syn. |
| 190 | 2-(S)-{2-[3-(4-Carbamimidoyl-phenyl)-2-cyclohexyl-propionylamino]-2-cyclohexyl-acetylamino}-5-guanidino-pentanoic acid cyclohexylmethyl-amide trifluoroacetic acid salt | ok | class. syn. |
| 191 | 2-(S)-{2-[3-(4-Carbamimidoyl-phenyl)-2-cyclohexyl-propionylamino]-2-cyclohexyl-acetylamino}-5-guanidino-pentanoic acid (naphthalen-1-ylmethyl)-amide trifluoroacetic acid salt | ok | class. syn. |
| 192 | 2-(S)-{2-[3-(4-Carbamimidoyl-phenyl)-2-cyclohexyl-propionylamino]-2-cyclohexyl-acetylamino}-5-guanidino-pentanoic acid (thiophen-2-ylmethyl)-amide trifluoroacetic acid salt | ok | class. syn. |
| 193 | 2-(S)-{2-[3-(4-Carbamimidoyl-phenyl)-2-cyclohexyl-propionylamino]-2-cyclohexyl-acetylamino}-5-guanidino-pentanoic acid (pyridin-3-ylmethyl)-amide trifluoroacetic acid salt | ok | class. syn. |
| 194 | 2-(S)-{2-[3-(4-Carbamimidoyl-phenyl)-2-cyclohexyl-propionylamino]-2-cyclohexyl-acetylamino}-5-guanidino-pentanoic acid (pyridin-4-ylmethyl)-amide trifluoroacetic acid salt | ok | class. syn. |
| 195 | 2-(S)-2-[3-(4-Carbamimidoyl-phenyl)-2-cyclohexyl-propionylamino]-2-cyclohexyl-acetylamino}-5-guanidino-pentanoic acid benzhydryl-amide trifluoroacetic acid salt | ok | class. syn. |
| 196 | 2-(S)-{2-[3-(4-Carbamimidoyl-phenyl)-2-cyclohexyl-propionylamino]-2-cyclohexyl-acetylamino}-5-guanidino-pentanoic acid benzylamide trifluoroacetic acid salt | ok | class. syn. |
| 197 | 2-(S)-{2-[3-(4-Carbamimidoyl-phenyl)-2-cyclohexyl-propionylamino]-2-cyclohexyl-acetylamino}-5-guanidino-pentanoic acid 2,4-dichloro-benzylamide trifluoroacetic acid salt | ok | class. syn. |
| 198 | 2-(S)-{2-[3-(4-Carbamimidoyl-phenyl)-2-cyclohexyl-propionylamino]-2-cyclohexyl-acetylamino}-5-guanidino-pentanoic acid 3,4-dichloro-benzylamide trifluoroacetic acid salt | ok | class. syn. |
| 199 | 2-(S)-{2-[3-(4-Carbamimidoyl-phenyl)-2-cyclohexyl-propionylamino]-2-cyclohexyl-acetylamino}-5-guanidino-pentanoic acid 3-methoxy-benzylamide trifluoroacetic acid salt | ok | class. syn. |
| 200 | 2-(S)-{2-[3-(4-Carbamimidoyl-phenyl)-2-cyclohexyl-propionylamino]-2-cyclohexyl-acetylamino}-5-guanidino-pentanoic acid 3,4-dimethoxy-benzylamide trifluoroacetic acid salt | ok | class. syn. |
| 201 | 2-(S)-{2-[3-(4-Carbamimidoyl-phenyl)-2-cyclohexyl-propionylamino]-2-cyclohexyl-acetylamino}-5-guanidino-pentanoic acid 4-chloro-benzylamide trifluoroacetic acid salt | ok | class. syn. |
| 202 | 2-(S)-{2-[3-(4-Carbamimidoyl-phenyl)-2-cyclohexyl-propionylamino]-2-cyclohexyl-acetylamino}-5-guanidino-pentanoic acid 4-methoxy-benzylamide trilfuoroacetic acid salt | ok | class. syn. |
| 203 | 2-(S)-{2-[3-(4-Carbamimidoyl-phenyl)-2-cyclohexyl-propionylamino]-2-cyclohexyl-acetylamino}-5-guanidino-pentanoic acid phenethyl-amide trifluoroacetic acid salt | ok | class. syn. |
| 204 | 2-(S)-{2-[3-(4-Carbamimidoyl-phenyl)-2-cyclohexyl-propionylamino]-2-cyclohexyl-acetylamino}-5-guanidino-pentanoic acid [2-(3,4-dimethoxy-phenyl)-ethyl]-amide trilfluoroacetic acid salt | ok | class. syn. |
| 205 | 2-(S)-{2-[3-(4-Carbamimidoyl-phenyl)-2-cyclohexyl-propionylamino]-2-cyclohexyl-acetylamino}-5-guanidino-pentanoic acid [2-(4-chloro-phenyl)-ethyl]-amide trilfuoroacetic acid salt | ok | class. syn. |
| 206 | 2-(S)-{2-[3-(4-Carbamimidoyl-phenyl)-2-cyclohexyl-propionylamino]-2-cyclohexyl-acetylamino}-5-guanidino-pentanoic acid (3,3-diphenyl-propyl)-amide trifluoroacetic acid salt | ok | class. syn. |

| | -continued | | |
|---|---|---|---|
| 207 | 2-(S)-{2-[3-(4-Carbamimidoyl-phenyl)-2-cyclohexyl-propionylamino]-2-cyclohexyl-acetylamino}-5-guanidino-pentanoic acid 3,5-bis-trifluoromethyl-benzylamide trifluoroacetic acid salt | ok | class. syn. |
| 208 | 2-(S)-{2-[3-(4-Carbamimidoyl-phenyl)-2-cyclohexyl-propionylamino]-2-cyclohexyl-acetylamino}-5-guanidino-pentanoic acid 2-chloro-benzylamide trifluoroacetic acid salt | ok | class. syn. |
| 209 | 2-(S)-{2-[3-(4-Carbamimidoyl-phenyl)-2-cyclohexyl-propionylamino]-2-cyclohexyl-acetylamino}-5-guanidino-pentanoic acid [2-(3-chloro-phenyl)-ethyl]-amide trifluoroacetic acid salt | ok | class. syn. |
| 210 | 2-(S)-{2-[3-(4-Carbamimidoyl-phenyl)-2-cyclohexyl-propionylamino]-2-cyclohexyl-acetylamino}-5-guanidino-pentanoic acid (2-phenoxy-ethyl)-amide trifluoroacetic acid salt | ok | class. syn. |
| 211 | 2-(S)-{2-[3-(4-Carbamimidoyl-phenyl)-2-cyclohexyl-propionylamino]-2-cyclohexyl-acetylamino}-5-guanidino-pentanoic acid [2-(3,4-dichloro-phenyl)-ethyl]-amide trifluoroacetic acid salt | ok | class. syn. |
| 212 | 2-(S)-{2-[3-(4-Carbamimidoyl-phenyl)-2-cyclohexyl-propionylamino]-2-cyclohexyl-acetylamino}-5-guanidino-pentanoic acid (adamantan-1-ylmethyl)-amide trifluoroacetic acid salt | ok | class. syn. |
| 213 | 2-(S)-{2-[3-(4-Carbamimidoyl-phenyl)-2-cyclohexyl-propionylamino]-2-cyclohexyl-acetylamino}-5-guanidino-pentanoic acid 3-cyano-benzylamide trifluoroacetic acid salt | ok | class. syn. |
| 214 | 3-(4-Carbamimidoyl-phenyl)-N-{(S)-[(1-carbamimidoyl-piperidin-4-ylmethyl)-carbamoyl]-cyclohexyl-methyl}-2-(2-fluoro-phenyl)-propionamide trifluoroacetic acid salt | ok | class. syn. |
| 215 | 3-(4-Carbamimidoyl-phenyl)-N-{(S)-[(1-carbamimidoyl-piperidin-4-ylmethyl)-carbamoyl]-cyclohexyl-methyl}-2-(4-chloro-phenyl)-propionamide trifluoroacetic acid salt, more polar diastereomer | ok | class. syn. |
| 216 | 3-(4-Carbamimidoyl-phenyl)-N-{(S)-[(1-carbamimidoyl-piperidin-4-ylmethyl)-carbamoyl]-cyclohexyl-methyl}-2-(4-chloro-phenyl)-propionamide trifluoroacetic acid salt, less polar diastereomer | ok | class. syn. |
| 217 | 2-(3-Bromo-phenyl)-3-(4-carbamimidoyl-phenyl)-N-{(S)-cyclohexyl-[(piperidin-4-ylmethyl)-carbamoyl]-methyl}-propionamide trifluoroacetic acid salt, more polar diastereomer | ok | class. syn. |
| 218 | 2-(3-Bromo-phenyl)-3-(4-carbamimidoyl-phenyl)-N-{(S)-cyclohexyl-[(piperidin-4-ylmethyl)-carbamoyl]-methyl}-propionamide trifluoroacetic acid salt, less polar diastereomer | ok | class. syn. |
| 219 | 2-(3-Bromo-phenyl)-N-{(S)-[(4-carbamimidoyl-cyclohexylmethyl)-carbamoyl]-cyclohexyl-methyl}-3-(4-carbamimidoyl-phenyl)-propionamide trifluoroacetic acid salt, less polar diastereomer | ok | class. syn. |
| 220 | 3-(4-Carbamimidoyl-phenyl)-N-{(S)-[(1-carbamimidoyl-piperidin-4-ylmethyl)-carbamoyl]-cyclohexyl-methyl}-2-(2-trifluoromethyl-phenyl)-propionamide trifluoroacetic acid salt, more polar diastereomer | ok | class. syn. |
| 221 | 3-(4-Carbamimidoyl-phenyl)-N-{(S)-[(1-carbamimidoyl-piperidin-4-ylmethyl)-carbamoyl]-cyclohexyl-methyl}-2-(2-trifluoromethyl-phenyl)-propionamide trifluoroacetic acid salt, less polar diastereomer | ok | class. syn. |
| 222 | 3-(4-Carbamimidoyl-phenyl)-N-{(S)-[(1-carbamimidoyl-piperidin-4-ylmethyl)-carbamoyl]-cyclohexyl-methyl}-2-phenyl-propionamide trifluoroacetic acid salt, less polar diastereomer | ok | class. syn. |

Example 223

2-(3-Bromo-phenyl)-3-(4-carbamimidoyl-phenyl)-N-((S)-cyclohexyl-{[1-(1-imino-ethyl)-piperidin-4-ylmethyl]-carbamoyl}-methyl)-propionamide trifluoracetic acid salt, less polar diastereomer a) 4-[(2-(S)-Benzyloxycarbonylamino-2-cyclohexyl-acetylamino)-methyl]-piperidine-1-carboxylic acid tert-butyl ester To (S)-benzyloxycarbonylamino-cyclohexyl-acetic acid (5.4 g, 18.66 mmol) and 4-aminomethyl-piperidine-1-carboxylic acid tert-butyl ester (4.0 g, 18.66 mmol) in dimethylformamide were added HATU (7.09 g, 18.66 mmol) and collidine (2.46 ml, 18.66 mmol) at 0° C. The mixture was stirred for 1 hour and then allowed to warm to room temperature. The mixture was evaporated and separated between ethyl acetate and sodium bicarbonate solution. The organic layer was washed with aqueous solution (pH 4), dried and evaporated. The resulting residue was taken up in ethyl acetate and washed with potassium hydrogen sulfate solution, dried and evaporated to give the desired product. Yield: 8.29 g (91%), MS m/z: 488.3 (M+H)$^+$.

b) 4-[(1-(S)-Amino-2-cyclohexyl-acetylamino)-methyl]-piperidine-1-carboxylic acid tert-butyl ester acetic acid salt 4-[(2-(S)-Benzyloxycarbonylamino-2-cyclohexyl-acetylamino)-methyl]piperidine-1-carboxylic acid tert-butyl ester (5.0 g, 10.25 mmol) was hydrogenated in ethanol (200 ml) and acetic acid (2 ml) using palladium (10%) as catalyst. The solvent was removed and partitioned between water and ethyl acetate. The aqueous layer was evaporated and lyophilized to give the desired product in quantitative yield. MS m/z: 354.3 (M+H$^+$).

c) 2-(3-Bromo-phenyl)-3-(4-cyano-phenyl)-propionic acid

To a solution of n-butyl lithium (95 ml, 15% solution in hexane, 147 mmol) and 2,2,6,6-tetramethylpiperidine (24.9 ml, 147 mmol) in tetrahydrofurane (220 ml) was added a solution of (3-bromo-phenyl)-acetic acid (15.05 g, 70 mmol) in tetrahydrofuran (80 ml) at −78° C. The reaction mixture was stirred for 60 minutes at that temperature. Then 4-bromomethyl-benzonitrile (13.72 g, 70 mmol) in tetrahydrofuran (160 ml) was added. The reaction mixture was stirred for 2 hours at −78° C., then warmed up to room temperature and quenched with ammonium chloride solution (240 ml), 3 N hydrochloric acid (50 ml), and ethyl acetate (300 ml). The organic layer was washed with ammonium chloride solution and brine, dried, and evaporated in vacuo. The residue was solved in ethyl acetate and stirred with methyl-tert-butylether. The precipitate was sucked off and dried in vacuo to give 19.0 g of the desired product (82% yield).

d) 4-({2-[2-(3-Bromo-phenyl)-3-(4-cyano-phenyl)-propionylamino]-2-(S)-cyclohexyl-acetylamino}-methyl) piperidine-1-carboxylic acid tert-butyl ester At 4° C., TOTU (1.59 g, 4.84 mmol) was added to a solution of 2-(3-bromo-phenyl)-3-(4-cyano-phenyl)-propionic acid (1.6 g, 4.84 mmol), 4-[(2-(S)-amino-2-cyclohexyl-acetylamino)-methyl]-piperidine-1-carboxylic acid tert-butyl ester acetic acid salt (2.0 g, 4.84 mmol), and N-ethylmorpholine (1.2 ml, 9.68 mmol) in dimethylformamide (80 ml). The mixture was stirred at 22° C. for 15 hours, then evaporated in vacuo and stirred with sodium bicarbonate solution. The resulting precipitate was sucked off, washed with water, and dried in vacuo at 40° C. to give the desired product, which was used without further purification. MS m/z 665.2 (M+H$^+$).

e) 2-(3-Bromo-phenyl)-3-(4-carbamimidoyl-phenyl)-N-{(S)-cyclohexyl-[(piperidin-4-ylmethyl)-carbamoyl]-methyl}-propionamide trifluoroacetic acid salt Through a solution of 4-({2-[2-(3-bromo-phenyl)-3-(4-cyano-phenyl)-propionylamino]-2-(S)-cyclohexyl-acetylamino}-methyl)-piperidine-1-carboxylic acid tert-butyl ester (3.7 g, 5.56 mmol) in dry ethanol (100 ml) was passed dry hydrochloric acid gas at −10° C. for 1 hour. The solution was stirred at room temperature for 12 hours, evaporated, and treated with a solution of ammonia in dry dimethylformamide (80 ml). After evaporation, the residue was purified by Sephadex LH20 employing n-butanol (17): glacial acetic acid (1): water (2) as eluent and prep. HPLC (HPLC conditions: Purospher(R)Star HP-18e (10 μM), acetonitrile/water+1% TFA, 10% to 100% acetonitrile). Pure fractions were combined and lyophilized to yield 1.06 g (24%) of the less polar diastereomer of the desired product. MS m/z: 582.3 (M+H$^+$).

f) 2-(3-Bromo-phenyl)-3-(4-carbamimidoyl-phenyl)-N-((S)-cyclohexyl-{[1-(1-imino-ethyl)-piperidin-4-ylmethyl]-carbamoyl}-methyl)-propionamide trifluoroacetic acid salt, less polar diastereomer A solution of 2-(3-bromo-phenyl)-3-(4-carbamimidoyl-phenyl)-N-{(S)-cyclohexyl-[(piperidin-4-ylmethyl)-carbamoyl]-methyl}-propionamide trifluoracetic acid salt (100 mg, 0.13 mmol, less polar diastereomer), ethyl acetimidate hydrochloride (32 mg, 0.26 mmol), and triethylamine (138 μl, 1.04 mmol) in methanol (40 ml) was stirred for 5 days. During the five days the same amount of triethylamine and ethyl acetimidate hydrochloride was added twice. The reaction mixture was evaporated in vacuo and purified by prep. HPLC (HPLC conditions: Purospher (R)Star HP-18e (10 μM), acetonitrile/water+1% TFA, 10% to 100% acetonitrile) to give 70 mg of the desired product (63% yield). MS m/z: 623.3 (M+H)$^+$.

Example 224 and 225

3-(4-Carbamimidoyl-phenyl)-N-{(S)-[(1-carbamimidoyl-piperidin-4-ylmethyl)-carbamoyl]-cyclohexyl-methyl}-2-(3-trifluoromethyl-phenyl)-propionamide trifluoracetic acid salt, more polar diastereomer and 3-(4-carbamimidoyl-phenyl)-N-{(S)-[(1-carbamimidoyl-piperidin-4-ylmethyl)-carbamoyl]-cyclohexyl-methyl}-2-(3-trifluoromethyl-phenyl)-propionamide trifluoroacetic acid salt, less polar diastereomer a) 3-(4-Cyano-phenyl)-2-(3-trifluoromethyl-phenyl)-propionic acid The title compound was prepared analogously to example 223 c) by using (3-trifluoromethyl-phenyl)-acetic acid instead of (3-bromo-phenyl)-acetic acid. Yield: 64%, MS m/z: 320.1 (M+H)$^+$.

b) (S)-{[(1-Carbamimidoyl-piperidin-4-ylmethyl)-carbamoyl]-cyclohexyl-methyl}-carbamic acid tert-butyl ester hydrochloric acid salt The title compound was prepared using (S)-tert-butoxycarbonylamino-cyclohexyl-acetic acid (10.1 g, 39.28 mmol), 4-aminomethyl-piperidine-1-carboxamidine dihydrochloride (9.0 g, 39.28 mmol) , HATU (14.9 g, 39.28 mmol), and collidine (15.6 ml, 117.8 mmol) in dimethylformamide as described in example 223 a).

c) (S)-2-Amino-N-(1-carbamimidoyl-piperidin-4-ylmethyl)-2-cyclohexyl-acetamide trifluoroactic acid salt A solution of (S)-{[(1-Carbamimidoyl-piperidin-4-ylmethyl)-carbamoyl]-cyclohexyl-methyl}-carbamic acid tert-butyl ester hydrochloric acid salt (20.0 g, 46.3 mmol) in trifluoroacetic acid (100 ml) was stirred for 12 hours at room temperature. The reaction mixture was evaporated and the residue was purified by Sephadex LH20 employing n-butanol (17): glacial acetic acid (1): water (2) as eluent. Pure fractions were combined to give the desired products. MS m/z: 296.2 (M+H)$^+$.

d) N-(S)-{[(1-Carbamimidoyl-piperidin-4-ylmethyl)-carbamoyl]-cyclohexyl-methyl}-3-(4-cyano-phenyl)-2-(3-trifluoromethyl-phenyl)-propionamide trifluoracetic acid salt The title compound was synthesized analogously to the procedure described in example 223 d) using (S)-2-amino-N-(1-carbamimidoyl-piperidin-4-ylmethyl)-2-cyclohexyl-acetamide trifluoroacetic acid salt (214 mg, 0.4 mmol), 3-(4-cyano-phenyl)-2-(3-trifluoromethyl-phenyl)-propionic acid (128 mg, 0.4 mmol), TOTU (132 mg, 0.4 mmol), and N-ethyl-morpholine (152 μl, 1.2 mmol) in dimethylformamide (10 ml) to give 240 mg (84%) of the desired product. MS m/z: 597.4 (M+H)$^+$.

e) N-{[(1-Carbamimidoyl-piperidin-4-ylmethyl)-carbamoyl]-cyclohexyl-methyl}-3-(4-cyano-phenyl)-2-(3-trifluoromethyl-phenyl)-propionamide hydrochloride Through a solution of N-(S)-{[(1-carbamimidoyl-piperidin-4-ylmethyl)-carbamoyl]-cyclohexyl-methyl}-3-(4-cyano-phenyl)-2-(3-trifluoromethyl-phenyl)-propionamide trifluoracetic acid salt (235 mg, 0.33 mmol) in dry ethanol (50 ml) was passed dry hydrochoric acid gas at −10° C. for 1 hour. The solution was stirred at room temperature for 12 hours, evaporated, and treated with a solution of ammonia in dry dimethylformamide for 3 days. After evaporation, the residue was purified by prep. HPLC (HPLC conditions: Purospher(R)Star HP-18e (10 μM), acetonitrile/water+1% TFA, 10% to 100% acetonitrile). Pure fractions were combined. The solvent was evaporated, the residue was taken up in water, and the aqueous solution was lyophilized to yield 68 mg (22%) of the more polar and 82 mg (26%) of the less polar diastereomer of the desired product. MS of both diastereomers show m/z: 614.4 (M+H)$^+$, 307.8 (M+2H)$^{2+}$.

The following compounds were synthesized using the procedures described in examples 1–10 and 223–225:

| | | | |
|---|---|---|---|
| 226 | 2-(S)-{2-[3-(4-Carbamimidoyl-phenyl)-2-cyclohexyl-propionylamino]-2-cyclohexyl-acetylamino}-5-guanidino-pentanoic acid tert-butyl ester trifluoroacetic acid salt, more polar diastereomer | ok | class. syn. |
| 227 | 2-(S)-{2-[3-(4-Carbamimidoyl-phenyl)-2-cyclohexyl-propionylamino]-2-cyclohexyl-acetylamino}-5-guanidino-pentanoic acid tert-butyl ester trifluoroacetic acid salt, less polar diastereomer | ok | class. syn. |
| 228 | N-[(S)-(4-Carbamimidoyl-benzylcarbamoyl)-cyclohexyl-methyl]-3-(4-carbamimidoyl-phenyl)-2-(R,S)-naphthalen-2-yl-propionamide hydrochloric acid salt | ok | class. syn. |
| 229 | 3-(4-Carbamimidoyl-phenyl)-N-{(S)-[(1-carbamimidoyl-piperidin-4-ylmethyl)-carbamoyl]-cyclohexyl-methyl}-2-(2-chloro-phenyl)-propionamide trifluoroacetic acid salt, more polar diastereomer | ok | class. syn. |
| 230 | 3-(4-Carbamimidoyl-phenyl)-N-{(S)-[(1-carbamimidoyl-piperidin-4-ylmethyl)-carbamoyl]-cyclohexyl-methyl}-2-(2-chloro-phenyl)-propionamide trifluoroacetic acid salt, less polar diastereomer | ok | class. syn. |
| 231 | 3-(4-Carbamimidoyl-phenyl)-N-{(S)-[(1-carbamimidoyl-piperidin-4-ylmethyl)-carbamoyl]-cyclohexyl-methyl}-2-(4-trifluoromethyl-phenyl)-propionamide trifluoroacetic acid salt, more polar diastereomer | ok | class. syn. |
| 232 | 3-(4-Carbamimidoyl-phenyl)-N-{(S)-[(1-carbamimidoyl-piperidin-4-ylmethyl)-carbamoyl]-cyclohexyl-methyl}-2-(4-trifluoromethyl-phenyl)-propionamide trifluoroacetic acid salt, less polar diastereomer | ok | class. syn. |
| 233 | 3-(4-Carbamimidoyl-phenyl)-N-{(S)-[(1-carbamimidoyl-piperidin-4-ylmethyl)-carbamoyl]-cyclohexyl-methyl}-2-(2-trifluoromethoxy-phenyl)-propionamide trifluoroacetic acid salt, less polar diastereomer | ok | class. syn. |
| 234 | 3-(4-Carbamimidoyl-phenyl)-N-{(S)-[(1-carbamimidoyl-piperidin-4-ylmethyl)-carbamoyl]-cyclohexyl-methyl}-2-(2-trifluoromethoxy-phenyl)-propionamide trifluoroacetic acid salt, more polar diastereomer | ok | class. syn. |
| 235 | 3-(4-Carbamimidoyl-phenyl)-N-{(S)-[(1-carbamimidoyl-piperidin-4-ylmethyl)-carbamoyl]-cyclohexyl-methyl}-2-(2-fluoro-phenyl)-propionamide trifluoroacetic acid salt, less polar diastereomer | ok | class. syn. |
| 236 | 2-(2-Bromo-phenyl)-3-(4-carbamimidoyl-phenyl)-N-{(S)-[(1-carbamimidoyl-piperidin-4-ylmethyl)-carbamoyl]-cyclohexyl-methyl}-propionamide trifluoroacetic aid salt, less polar diastereomer | ok | class. syn. |
| 237 | 3-(4-Carbamimidoyl-phenyl)-N-{(S)-[(1-carbamimidoyl-piperidin-4-ylmethyl)-carbamoyl]-cyclohexyl-methyl}-2-(2-methoxy-phenyl)-propionamide trifluoroacetic acid salt, less polar diastereomer | ok | class. syn. |
| 238 | 2-(3-Bromo-phenyl)-3-(4-carbamimidoyl-phenyl)-N-((S)-cyclohexyl-{[1-(imino-phenyl-methyl)-piperidin-4-ylmethyl]-carbamoyl}-methyl)-propionamide trifluoroacetic acid salt, less polar diastereomer | ok | class. syn. |
| 239 | 2-(3-Bromo-phenyl)-3-(4-carbamimidoyl-phenyl)-N-((S)-cyclohexyl-{[1-(imino-pyridin-2-yl-methyl)-piperidin-4-ylmethyl]-carbamoyl}-methyl)-propionamide trifluoroacetic acid salt, less polar diastereomer | ok | class. syn. |
| 240 | 3-(4-Carbamimidoyl-phenyl)-N-{(S)-[(1-carbamimidoyl-piperidin-4-ylmethyl)-carbamoyl]-cyclohexyl-methyl}-2-naphthalen-1-yl-propionamide trifluoroacetic acid salt, more polar diastereomer | ok | class. syn. |
| 241 | 3-(4-Carbamimidoyl-phenyl)-N-{(S)-[(1-carbamimidoyl-piperidin-4-ylmethyl)-carbamoyl]-cyclohexyl-methyl}-2-naphthalen-1-yl-propionamide trifluoroacetic acid salt, less polar diastereomer | ok | class. syn. |
| 242 | 2-(S)-{2-[2-(3-Bromo-phenyl)-3-(4-carbamimidoyl-phenyl)-propionylamino]-2-(S)-cyclohexyl-acetylamino}-5-guanidino-pentanoic acid isopropyl ester trifluoroacetic acid salt, less polar diastereomer | ok | class. syn. |
| 243 | 2-(S)-{2-[2-(3-Bromo-phenyl)-3-(4-carbamimidoyl-phenyl)-propionylamino]-2-(S)-cyclohexyl-acetylamino}-5- | | |

-continued

| | | | |
|---|---|---|---|
| | guanidino-pentanoic acid isopropyl ester trifluoroacetic acid salt, more polar diastereomer | | |
| 244 | 2-(3-Bromo-phenyl)-N-[(S)-(5-carbamimidoyl-pentylcarbamoyl)-cyclohexyl-methyl]-3-(4-carbamimidoyl-phenyl)-propionamide trifluoroacetic acid salt, less polar diastereomer | ok | class. syn. |
| 245 | 2-(3-Bromo-phenyl)-N-[(S)-(5-carbamimidoyl-pentylcarbamoyl)-cyclohexyl-methyl]-3-(4-carbamimidoyl-phenyl)-propionamide trifluoroacetic acid salt, more polar diastereomer | ok | class. syn. |
| 246 | 2-(S)-{2-[2-(3-Bromo-phenyl)-3-(4-carbamimidoyl-phenyl)-propionylamino]-2-(S)-cyclohexyl-acetylamino}-5-guanidino-pentanoic acid dimethylamide trifluoroacetic acid salt, less polar diastereomer | ok | class. syn. |
| 247 | 2-(S)-{2-[2-(3-Bromo-phenyl)-3-(4-carbamimidoyl-phenyl)-propionylamino]-2-(S)-cyclohexyl-acetylamino}-5-guanidino-pentanoic acid dimethylamide trifluoroacetic acid salt, more polar diastereomer | ok | class. syn. |
| 248 | 3-(4-Amino-phenyl)-N-{(S)-[(1-carbamimidoyl-piperidin-4-ylmethyl)-carbamoyl]-cyclohexyl-methyl}-2-(3-trifluoromethyl-phenyl)-propionamide trifluoroacetic acid salt, less polar diastereomer | ok | class. syn. |
| 249 | 3-(4-Amino-phenyl)-N-{(S)-[(1-carbamimidoyl-piperidin-4-ylmethyl)-carbamoyl]-cyclohexyl-methyl}-2-(3-trifluoromethyl-phenyl)-propionamide trifluoroacetic acid salt, more polar diastereomer | ok | class. syn. |
| 250 | 2-(3-Bromo-phenyl)-3-(4-carbamimidoyl-phenyl)-N-((S)-{[1-(2-cyano-1-imino-ethyl)-piperidin-4-ylmethyl]-carbamoyl}-cyclohexyl-methyl)-propionamide trifluoroacetic acid salt, less polar diastereomer | ok | class. syn. |
| 251 | 2-(3-Bromo-phenyl)-3-(4-carbamimidoyl-phenyl)-N-((S)-cyclohexyl-{[1-(1-imino-2-methyl-propyl)-piperidin-4-ylmethyl]-carbamoyl}-methyl)-propionamide trifluoroacetic acid salt, less polar diastereomer | ok | class. syn. |
| 252 | 3-(4-Carbamimidoyl-phenyl)-N-{(S)-[(1-carbamimidoyl-piperidin-4-ylmethyl)-carbamoyl]-cyclohexyl-methyl}-2-(3-methanesulfonyl-phenyl)-propionamide trifluoroacetic acid salt, less polar diastereomer | ok | class. syn. |
| 253 | 3-(4-Carbamimidoyl-phenyl)-N-{(S)-[(1-carbamimidoyl-piperidin-4-yl methyl)-carbamoyl]-cyclohexyl-methyl}-2-(3-methanesulfonyl-phenyl)-propionamide trifluoroacetic acid salt, more polar diastereomer | ok | class. syn. |
| 254 | 3-(4-Amino-phenyl)-N-((S)-cyclohexyl-{[1-(1-imino-ethyl)-piperidin-4-ylmethyl]-carbamoyl}-methyl)-2-(3-trifluoromethyl-phenyl)-propionamide trifluoroacetic acid salt, less polar diastereomer | ok | class. syn. |
| 255 | 3-(4-Amino-phenyl)-N-((S)-cyclohexyl-{[1-(1-imino-ethyl)-piperidin-4-ylmethyl]-carbamoyl}-methyl)-2-(3-trifluoromethyl-phenyl)-propionamide trifluoroacetic acid salt, more polar diastereomer | ok | class. syn. |
| 256 | 3-(4-Aminomethyl-phenyl)-N-{(S)-[(1-carbamimidoyl-piperidin-4-ylmethyl)-carbamoyl]-cyclohexyl-methyl}-2-(3-trifluoromethyl-phenyl)-propionamide trifluoroacetic acid salt, less polar diastereomer | ok | class. syn. |
| 257 | 3-(4-Aminomethyl-phenyl)-N-{(S)-[(1-carbamimidoyl-piperidin-4-ylmethyl)-carbamoyl]-cyclohexyl-methyl}-2-(3-trifluoromethyl-phenyl)-propionamide trifluoroacetic acid salt, more polar diastereomer | ok | class. syn. |

Example 258 and 259

3-(4-Carbamimidoyl-phenyl)-N-((S)-cyclohexyl-{[1-(1-imino-ethyl)-piperidin-4-ylmethyl]-carbamoyl}-methyl)-2-(3-trifluoromethyl-phenyl)-propionamide trifluoroacetic acid salt, less polar diastereomer and 3-(4-carbamimidoyl-phenyl)-N-((S)-cyclohexyl-{[1-(1-imino-ethyl)-piperidin-4-ylmethyl]-carbamoyl}-methyl)-2-(3-trifluoromethyl-phenyl)-propionamide trifluoroacetic acid salt, more polar diastereomer a) 2-Amino-2-(S)-cyclohexyl-N-[1-(1-imino-ethyl)-piperidin-4-ylmethyl]-acetamide trifluoroacetic acid salt a1) (S)-{Cyclohexyl-[(piperidin-4-ylmethyl)-carbamoyl]-methyl}-carbamic acid benzyl ester trifluoroacetic acid salt 4-[(2-(S)-Benzyloxycarbonylamino-2-cyclohexyl-acetylamino)-methyl]-piperidine-1-carboxylic acid tert-butyl ester (7.15 g, 14.66 mmol, example 223 a)) was solved in trifluoracetic acid (90% in water, 100 ml). The reaction mixture was stirred for 15 h and evaporated in vacuo to give 7.1 g of the desired product (97%). MS m/z: 388.4 (M+H)$^+$.

a2) (S)-(Cyclohexyl-{[1-imino-ethyl)-piperdin-4-ylmethyl]-carbamoyl}-methyl)-carbamic acid benzyl ester trifluoroacetic acid salt The title compound was synthesized using (S)-{cyclohexyl-[(piperidin-4-ylmethyl)-carbamoyl]-methyl}-carbamic acid benzyl ester trifluoroacetic acid salt (2.0 g, 3.98 mmol), ethyl acetimidate (1.98 g, 16 mmol, in two portions), and triethylamine (9 ml, in two portions) in methanol as described in example 233 f). The crude material was purified by prep. HPLC (HPLC conditions: Purospher (R)Star HP-18e (10 μM), acetonitrile/water+1% TFA, 10% to 100% acetonitrile) to give the desired product. MS m/z: 429.4 (M+H)$^+$.

a3) 2-Amino-2-(S)-cyclohexyl-N-[1-(1-imino-ethyl)-piperidin-4-ylmethyl]-acetamide trifluoroacetic acid salt (S)-(Cyclohexyl-{[1-(1-imino-ethyl)-piperidin-4-ylmethyl]-carbamoyl}-methyl)-carbamic acid benzyl ester trifluoroacetic acid salt (340 mg, 0.62 mmol) was hydrogenated in methanol (50 ml) and acetic acid (3 ml) using palladium/charcoal (10%) as a catalyst. The solvent was evaporated and the residue solved in water and lyophilized to give 287 mg of the desired product (88%). MS m/z: 295.4 (M+H)$^+$.

b) 3-(4-Carbamimidoyl-phenyl)-2-(3-trifluoromethyl-phenyl)-propionic acid acetic acid salt b1) 3-[4-(N-Hydroxycarbamimidoyl)-phenyl]-2-(3-trifluoromethyl-phenyl)-propionic acid A solution of 3-[4-cyano-phenyl]-2-trifluoromethyl-phenyl)-propionic acid (3.05 g, 9.6 mmol), example 224/225 a), hydroxylamine hydrochloride (4.0 g, 57.6 mmol), and triethylamine (9.3 ml, 67.2 mmol) in 2-propanol (100 ml) was stirred for 15 hours. The reaction mixture was sucked off and evaporated in vacuo. The residue was partitioned between water and ethyl acetate. The aqueous layer was extracted with ethyl acetate, acidified with potassium bicarbonate solution, and extracted with ethyl acetate. The organic layer was dried and evaporated to give 2.3 g of the desired product (68%). MS m/z: 353.2 (M+H)$^+$.

b2) 3-(4-Carbamimidoyl-phenyl)-2-(3-trifluoromethyl-phenyl)-propionic acid acetic acid salt 3-[4-(N-Hydroxycarbamimidoyl)-phenyl]-2-(3-trifluoromethyl-phenyl)-propionic acid (680 mg, 1.93 mmol) was hydrogenated in acetic acid (50 ml) using palladium/charcoal (10%) as the catalyst. After two days, the catalyst was filtered off and the solvent evaporated in vacuo to give 500 mg of the desired product (65%). MS m/z: 337.2 (M+H)$^+$.

c) 3-(4-Carbamimidoyl-phenyl)-N-((S)-cyclohexyl-{[1-(1-imino-ethyl)-piperidin-4-ylmethyl]-carbamoyl}-methyl)-2-(3-trifluoromethyl-phenyl)-propionamide trifluoroacetic acid salt, less polar diastereomer and 3-(4-Carbamimidoyl-phenyl)-N-((S)-cyclohexyl-{[1-(1-imino-ethyl)-piperidin-4-ylmethyl]-carbamoyl}-methyl)-2-(3-trifluoromethyl-phenyl)-propionamide trifluoroacetic acid salt, more polar diastereomer The title compound was synthesized analogously to the procedure described in example 223 d) using 2-amino-2-(S)-cyclohexyl-N-[1-(1-imino-ethyl)-piperidin-4-ylmethyl]-acetamide trifluoroacetic acid salt (100 mg, 0.2 mmol), 3-(4-carbamimidoyl-phenyl)-2-(3-trifluoromethyl-phenyl)-propionic acid acetic acid salt (80 mg, 0.2 mmol), TOTU (65 mg, 0.2 mmol), and N-ethyl-morpholine (76 μl, 0.6 mmol) in dimethylformamide. The crude material was purified by prep. HPLC (HPLC conditions: Purospher(R)Star HP-18e (10 μM), acetonitrile/water+1% TFA, 10% to 100% acetonitrile) to give the two diastereomers. MS of both diastereomers show m/z: 613.4 (M+H)$^+$, 307.4 (M+H)$^{2+}$.

The following compounds were synthesized using the procedures described in examples 1–10, 223–225, and 258–259:

| | | | |
|---|---|---|---|
| 260 | N-((S)-Cyclohexyl-{[1-(1-imino-ethyl)-piperidin-4-ylmethyl]-carbamoyl}-methyl)-3-[4-(N-hydroxycarbamimidoyl)-phenyl]-2-(3-trifluoromethyl-phenyl)-propionamide trifluoroacetic acid salt, less polar diastereomer | ok | class. syn. |
| 261 | N-((S)-Cyclohexyl-{[1-(1-imino-ethyl)-piperidin-4-ylmethyl]-carbamoyl}-methyl)-3-[4-(N-hydroxycarbamimidoyl)-phenyl]-2-(3-trifluoromethyl-phenyl)-propionamide trifluoroacetic acid salt, more polar diastereomer | ok | class. syn. |
| 262 | 3-(4-Carbamimidoyl-phenyl)-N-((S)-cyclohexyl-{[1-(1-imino-propyl)-piperidin-4-ylmethyl]-carbamoyl}-methyl)-2-(3-trifluoromethyl-phenyl)-propionamide trifluoroacetic acid salt, less polar diastereomer | ok | class. syn. |
| 263 | 3-(4-Carbamimidoyl-phenyl)-N-((S)-cyclohexyl-{[1-(1-imino-propyl)-piperidin-4-ylmethyl]-carbamoyl}-methyl)-2-(3-trifluoromethyl-phenyl)-propionamide trifluoroacetic acid salt, more polar diastereomer | ok | class. syn. |
| 264 | N-((S)-Cyclohexyl-{[1-(1-imino-ethyl)-piperidin-4-ylmethyl]-carbamoyl}-methyl)-3-[4-(5-methyl-[1,2,4]oxadiazol-3-yl)-phenyl]-2-(R,S)-(3-trifluoromethyl-phenyl)-propionamide trifluoroacetic acid salt | ok | class. syn. |
| 265 | 3-(4-Carbamimidoyl-phenyl)-N-{(S)-cyclohexyl-[(piperidin-4-ylmethyl)-carbamoyl]-methyl}-2-(3-trifluoromethyl-phenyl)-propionamide trifluoroacetic acid salt, less polar diastereomer | ok | class. syn. |
| 266 | 3-(4-Carbamimidoyl-phenyl)-N-{(S)-cyclohexyl-[(piperidin-4-ylmethyl)-carbamoyl]-methyl}-2-(3-trifluoromethyl-phenyl)-propionamide trifluoroacetic acid salt, more polar diastereomer | ok | class. syn. |
| 267 | 3-(1-Amino-isoquinolin-6-yl)-N-((S)-cyclohexyl-{[1-(1-imino-ethyl)-piperidin-4-ylmethyl]-carbamoyl}-methyl)-2-(3-trifluoromethyl-phenyl)-propionamide trifluoroacetic acid salt, more polar diastereomer | ok | class. syn. |
| 268 | 3-(1-Amino-isoquinolin-6-yl)-N-((S)-cyclohexyl-{[1-(1-imino-ethyl)-piperidin-4-ylmethyl]-carbamoyl}-methyl)-2-(3-trifluoromethyl-phenyl)-propionamide trifluoroacetic acid salt, less polar diastereomer | ok | class. syn. |
| 269 | 3-(4-Carbamimidoyl-phenyl)-N-{[(1-carbamimidoyl-piperidin-4-ylmethyl)-carbamoyl]-methyl}-2-(3-trifluoromethyl-phenyl)-propionamide | ok | class. syn. |
| 270 | 3-[4-(N-tert-Butoxy-carbamimidoyl)-phenyl]-N-((S)-cyclohexyl-{[1-(1-imino-ethyl)-piperidin-4-ylmethyl]-carbamoyl}-methyl)-2-(3-trifluoromethyl-phenyl)- | ok | class. syn. |

-continued

| | | | |
|---|---|---|---|
| 271 | 3-[4-(N-tert-Butoxy-carbamimidoyl)-phenyl]-N-((S)-cyclohexyl-{[1-(1-imino-ethyl)-piperidin-4-ylmethyl]-carbamoyl}-methyl)-2-(3-trifluoromethyl-phenyl)-propionamide trifluoroacetic acid salt, more polar diastereomer | ok | class. syn. |
| 272 | N-((S)-Cyclohexyl-{[1-(1-imino-ethyl)-piperidin-4-ylmethyl]-carbamoyl}-methyl)-3-[4-(N-methylcarbamimidoyl)-phenyl]-2-(3-trifluoromethyl-phenyl)-propionamide trifluoroacetic acid salt | ok | class. syn. |

(first row continuation: propionamide trifluoroacetic acid salt, less polar diastereomer)

N-((S)-Cyclohexyl-{[1-(1-imino-ethyl)-piperidin-4-ylmethyl]-carbamoyl}-methyl)-3-[4-(5-oxo-4,5-dihydro-[1,2,4]oxadiazol-3-yl)-phenyl]-2-(3-trifluoromethyl-phenyl)-propionamide trifluoroacetic acid salt a) 3-[4-(N-Hydroxycarbamimidoyl)-phenyl]-2-(3-trifluoromethyl-phenyl)-propionic acid methyl ester A solution of 3-[4-(N-hydroxycarbamimidoyl)-phenyl]-2-(3-trifluoromethyl-phenyl)-propionic acid (300 mg, 0.85 mmol, example 258/259 b1)) and oxalyl dichloride (119 mg, 0.95 mmol) in methanol (10 ml) was stirred for 1.5 days. The solvent was evaporated, and the residue solved in water and lyophilized to give 320 mg of the desired product (quantitative). MS m/z: 367.2 (M+H)$^+$.

b) 3-[4-(N-Ethoxycarbonyloxycarbamimidoyl)-phenyl]-2-(3-trifluoromethyl-phenyl)-propionic acid methyl ester To a solution of 3-[4-(N-hydroxycarbamimidoyl)-phenyl]-2-(3-trifluoromethyl-phenyl)-propionic acid methyl ester (310 mg, 0.85 mmol) in dimethylformamide (20 ml) was added triethylamine (475 µl, 3.4 mmol) and ethyl chloroformiate (81 µl, 0.85 mmol). After three days, the reaction mixture was evaporated in vacuo and the residue dissolved in ethyl acetate/potassium hydrogen sulfate solution. The organic layer was dried and evaporated in vacuo to give 265 mg of the desired product (71% yield). MS m/z: 439.2 (M+H)$^+$.

c) 3-[4-(5-Oxo-4,5-dihydro-[1,2,4]oxadiazol-3-yl)-phenyl]-2-(3-trifluoromethyl-phenyl)-propionic acid methyl ester A mixture of 3-[4-(N-ethoxycarbonyloxycarbamimidoyl)-phenyl]-2-(3-trifluoromethyl-phenyl)-propionic acid methyl ester (30 mg, 68 µmol), sodium carbonate (2.0 g), dimethylformamide (10 ml), and water (10 ml) was stirred at room temperature for 2 days. The reaction mixture was evaporated, and the residue solved in potassium hydrogen sulfate solution and ethyl acetate. The organic layer was evaporated and gave after lyophilization 22 mg of the desired product (85% yield). MS m/z: 379.1 (M+H)$^+$.

d) N-((S)-Cyclohexyl-{[1-(1-imino-ethyl)-piperidin-4-ylmethyl]-carbamoyl}-methyl)-3-[4-(5-oxo-4,5-dihydro-[1,2,4]-oxadiazol-3-yl)-phenyl]-2-(3-trifluoromethyl-phenyl)-propionamide trifluoroacetic acid salt The title compound was prepared as a diastereomeric mixture from 3-[4-(5,5-dimethyl-4,5-dihydro-[1,2,4]oxadiazol-3-yl)-phenyl]-2-(3-trifluoromethyl-phenyl)-propionic acid as described in example 258/259 c) to give the desired product. MS m/z: 655.3 (M+H)$^+$.

Example 274

N-((S)-Cyclohexyl-{[1-(1-imino-ethyl)-piperidin-4-ylmethyl]-carbamoyl}-methyl)-3-(4-sulfimidamoyl-phenyl)-2-(3-trifluoromethyl-phenyl)-propionamide trifluoroacetic acid salt a) 3-(4-Nitro-phenyl)-2-(3-trifluoromethyl-phenyl)-acrylic acid A solution of (3-trifluoromethyl-phenyl)-acetic acid (7.5 g, 36.7 mmol), 4-nitro-benzaldehyde (5.55 g, 36.7 mmol), triethylamine (4.8 g, 47.8 mmol), and acetic anhydride (14.3 g, 140 mmol) was refluxed for 6 hours. The reaction mixture was poured in acidified water (sulfuric acid, pH 1) and extracted with ethyl acetetate. The organic layer was evaporated and the residue was stirred with sodium bicarbonate solution. The precipitate was sucked off and the filtrate extracted with ethyl acetate. The water was acidified with hydrochloric acid and the resulting oil extracted with ethyl acetate to give 9.9 g of the desired product (80% yield).

b) 3-(4-Amino-phenyl)-2-(3-trifluoromethyl-phenyl)-propionic acid 3-(4-Nitro-phenyl)-2-(3-trifluoromethyl-phenyl)-acrylic acid (9.9 g, 29 mmol) was hydrogenated in methanol using palladium/charcoal (10%) as the catalyst in 13 hours. The catalyst was filtered off and the filtrate was evaporated to give 8.9 g of the desired product (98% yield). MS m/z: 310.2 (M+H)$^+$.

c) 3-(4-Mercapto-phenyl)-2-(3-trifluoromethyl-phenyl)-propionic acid

To a suspension of 3-(4-amino-phenyl)-2-(3-trifluoromethyl-phenyl)-propionic acid (4.0 g, 12.9 mmol) in water (50 ml) and hydrochloric acid (2.8 ml, 32.3 mmol) at 0–5° C. was added sodium nitrite (0.89 g, 12.9 mmol) in water (20 ml). The reaction mixture was warmed to room temperature and poured in a solution of the sodium salt of dithiocarbonic acid O-ethyl ester (4.14 g, 25.8 mmol) in water (20 ml). The reaction mixture was stirred at 60° C. for 2 hours and the precipitate (resin) was solved with ethyl acetate. The organic layer was washed with water, dried, and evaporated in vacuo. The resulting dark brown oil was solved in ethanol (50 ml). At refluxing temperature, sodium hydroxide (3.6 g, 64.5 mmol) was added. After three hours at that temperature, the ethanol was removed, the residue solved in water, and the aqueous layer washed with dichloromethane. To the aqueous layer, potassium hydrogensulfate (10 g) was added. The resulting oil was extracted with dichloromethane, dried, and evaporated in vacuo to give 3.05 g (72%) of the desired product. MS m/z: 327.2 (M+H)$^+$.

d) 3-[4-(N,N-bis-tert-butyl-sulfimidamoyl)-phenyl]-2-(3-trifluoromethyl-phenyl)-propionic acid To tert-butyl amine (29 ml), was added bromine (1.05 ml, 20.43 mmol) at −35° C. The suspension was stirred mechanically and warmed to −5° C. The 3-(4-mercapto-phenyl)-2-(3-trifluoro-phenyl)-propionic acid (2.0 g, 6.13 mmol) solved in dichloromethane was added, the reaction mixture was stirred for 1 day at 0° C., and then the mixture stood for 3 days at room temperature. The tert-butyl-amine was removed and the residue was solved in Na$_2$SO—NaH$_2$PO$_4$-solution and dichloromethane. The organic layer was dried and evaporated in vacuo to give 2.82 g of the desired product (95%), which was used without further purification.

e) 3-(4-sulfimidamoyl-phenyl)-2-(3-trifluoromethyl-phenyl)-propionic acid

3-[4-(N,N-bis-tert-Butyl-sulfimidamoyl)-phenyl]-2-(3-trifluoromethyl-phenyl)-propionic acid (200 mg, 0.41 mmol) was solved in acetic acid/hydrobromic acid (5 ml) and stirred for 16 hours. Water (50 ml) was added to the reaction mixture and the mixture was then brought to pH 5 (sodium bicarbonate solution). The aqueous layer was extracted with dichloromethane, and the organic layer was dried, evaporated and purified by prep. HPLC (HPLC conditions: Purospher(R)Star HP-18e (10 μM), acetontrile/water+1% TFA, 10% to 100% acetonitrile) to give 10 mg of the desired product.

f) N-((S)-Cyclohexyl-{[1-(1-imino-ethyl)-piperidin-4-ylmethyl]-carbamoyl}-methyl)-3-(4-sulfimidamoyl-phenyl)-2-(3-trifluoromethyl-phenyl)-propionamide triflouracetic acid salt A solution of 3-(4-sulfimidamoyl-phenyl)-2-(3-trifluoromethyl-phenyl)-propionic acid (30 mg, 80 μmol, prepared analogously to the procedure described above), 2-amino-2-(S)-cyclohexyl-N-[1-(1-imino-ethyl)-piperidin-4-ylmethyl]-acetamide trifluoroacetic acid salt (44 mg, 80 μmol, prepared analogously to the procedure described in example 258/259 a)), TOTU (29 mg, 88 μmol), and N-ethylmorpholine (30 μl, 240 μmol) in dimethylformamide (10 ml) was stirred for 2 hours at 0° C. The reaction mixtured was warmed to room temperature and evaporated. The residue was purified by prep. HPLC (HPLC conditions: Purospher(R)Star HP-18e (10 μM), acetonitrile/water+1% TFA, 10% to 100% acetonitrile) to give 11 mg of the desired product as a diastereomeric mixture (18% yield). MS m/z: 649.2 (M+H)+.

Example 275 and 276

N-((S)-Cyclohexyl-{[1-(1-imino-ethyl)-piperidin-4-ylmethyl]-carbamoyl}-methyl)-3-[4-(5,5-dimethyl-4,5-dihydro-[1,2,4]-oxadiazol-3-yl)-phenyl]-2-(3-trifluoromethyl-phenyl)-propionamide trifluoroacetic acid salt, less polar diastereomer and N-((S)-Cyclohexyl-{[1-(1-imino-ethyl)-piperidin-4-ylmethyl]-carbamoyl}-methyl)-3-[4-(5,5-dimethyl-4,5-dihydro-[1,2,4]oxadiazol-3-yl)-phenyl]-2-(3-trifluoromethyl-phenyl)-propionamide trifluoroacetic acid salt, more polar diastereomer a) 3-[4-(5,5-Dimethyl-4,5-dihydro-[1,2,4]oxadiazol-3-yl)-phenyl]-2-(3-trifluoromethyl-phenyl)propionic acid A solution of 3-[4-(N-hydroxycarbamimidoyl)-phenyl]-2-(3-trifluoromethyl-phenyl)-propionic acid (200 mg, 0.57 mmol, example 258/259 b 1)) in acetone (50 ml) was refluxed for 8 hours per day for five days. The reaction mixture was evaporated in vacuo and the residue was purified by prep. HPLC (HPLC conditions: Purospher(R) Star HP-18e (10 μm), acetonitrile/water+1% TFA, 10% to 100% acetonitrile) to give 90 mg of the desired product (40%). MS m/z: 393.1 (M+H)+.

b) N-((S)-Cyclohexyl-{[1-(1-imino-ethyl)-piperidin-4-ylmethyl]-carbamoyl}-methyl)-3-[4-(5,5-dimethyl-4,5-dihydro-[1,2,4]oxadizol-3-yl)-phenyl]-2-(3-trifluoromethyl-phenyl)-propionamide trifluoroacetic acid salt, less polar diastereomer and N-((S)-Cyclohexyl-{[1-(1-imino-ethyl)-piperidin-4-ylmetyl]-carbamoyl}-methyl)-3-[4-(5,5-dimethyl-4,5-dihydro-[1,2,4]oxadiazol-3-yl)-phenyl]-2-(3-trifluoromethyl-phenyl)-propionamide trifluoroacetic acid salt, more polar diastereomer The title compounds were prepared from 3-[4-(5,5-dimethyl-4,5-dihydro-[1,2,4]oxadizol-3-yl)phenyl]-2-(3-trifluoromethyl-phenyl)-propionic acid as described in example 258/259 c to give the desired product. MS m/z: 669.3 (M+H)+.

The following compounds were synthesized using the procedures described in examples 1–10, 223–225, 258–259, and 273–276.

| 277 | 3-(4-Acetylamino-phenyl)-N-((S)-cyclohexyl-{[1-(1-imino-ethyl)-piperidin-4-ylmethyl]-carbamoyl}-methyl)-2-(3-trifluoromethyl-phenyl)-propionamide trifluoroacetic acid salt, less polar diastereomer | ok | class. syn. |
|---|---|---|---|
| 278 | 3-[4-(Acetylimino-amino-methyl)-phenyl]-N-((S)-{[1-(acetylimino-amino-methyl)-piperidin-4-ylmethyl]-carbamoyl}-cyclohexyl-methyl)-2-(3-bromo-phenyl)-propionamide, less polar diastereomer | ok | class. syn. |
| 279 | 3-(4-(N-Methycarbonyloxy-carbamimidoyl-phenyl)-N-(cyclohexyl-{[1-(1-imino-ethyl)-piperidin-4-ylmethyl]-carbamoyl}-methyl)-2-(3-trifluoromethyl-phenyl)-propionamide trifluoroacetic acid salt, less polar diastereomer | ok | class. syn. |

Abbreviations used in the text:

| | |
|---|---|
| APTT | activated partial thromboplastin time |
| ATS | Antistasin |
| AV | Arteriovenous |
| Boc | Benzyloxycarbonyl |
| bp. | boiling point |
| ° C. | degrees Celsius |
| CDCl$_3$ | deutero chloroform |
| Class. syn. | classical synthesis |
| Cm | Centimeter |
| Dc | Decomposition |
| DCCI | Dicyclohexylcarbodiimide |
| DCRu | Dichlorotetrakis (triphenylphosphine) ruthenium (II) |
| DIC | disseminated intravascular coagulation |
| DICI | Diisopropylcarbodiimide |
| DMSO | Dimethylsulfoxide |
| DVT | deep vein thrombosis |
| eq. | Equivalent |
| Fmoc | 9-fluorenylmethoxycarbonyl |
| FT-IR | fourier transformed infrared |
| G | Gram |
| H | Hour |
| HATU | N-[(dimethylamino)-1H-1,2,3-triazolo[4,5-b]pyridin-1yl-methylene]-N-methylmethanaminium hexafluorophosphate N-oxide |
| HOBt | 1-Hydroxybenzotriazole |
| HPLC | high pressure liquid chromatography |
| HPLC/ESMS | high pressure liquid chromatography/electro spray mass spectra |
| Id | Intraduodenal |
| Iv | Intravenous |
| Kg | Kilogram |

-continued

| | |
|---|---|
| LMWH | low molecular weight heparin |
| Mg | Milligram |
| MHz | Megahertz |
| Min | Minutes |
| Ml | Milliliter |
| Mm Hg | millimeters of mercury (with 1 mm Hg being equivalent to 1.3332 millibar or 133.32 Pascal) |
| MM | Millimolar |
| Mmol | Millimol |
| MS | mass spectra |
| Mp. | melting point |
| μl | Microliter |
| μm | Micrometer |
| μM | Micromolar |
| μmol | Micromol |
| Nm | Nanometer |
| NM | Nanomolar |
| NMR | nuclear magnetic resonance |
| PE | Polyethylene |
| PEG | Polyethyleneglycol |
| PG | protecting group |
| PPP | platelet poor blood |
| PT | prothrombin time |
| Sec | Seconds |
| Solid ph. | solid phase synthesis |
| TAP | tick anticoagulant peptide |
| TBS-BSA | Tris buffered saline bovine serum albumin |
| TBS-PEG | Tris buffered saline polyethylene glycole |
| TFPI | tissue factor pathway inhibitor |
| TOTU | O-((cyano-(ethoxycarbonyl)-methylen)amino)-N,N,N',N'-tetramethyluronium tetrafluoroborate |
| TPCK | Tosyl phenyl chloromethyl ketone |
| UV | ultra violet |

We claim:
1. A compound of formula (I):

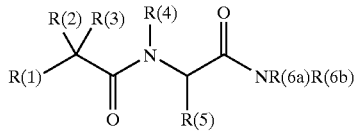

in any stereoisomeric form, or a physiologically acceptable salt thereof, wherein:
R(1) is $C_6$ aryl, wherein aryl is unsubstituted or substituted by 1, 2, or 3 identical or different groups R(8);
R(2) is hydrogen or $(C_1–C_4)$-alkyl;
R(3) is $(C_6-)$-aryl-$(C_1–C_4)$-alkyl which is substituted in the aryl or alkyl moiety by a group R(11);
R(4) is hydrogen, $(C_1–C_4)$-alkyl, $(C_3–C_7)$-cycloalkyl, $(C_3–C_7)$-cycloalkyl-$(C_1–C_4)$-alkyl, or $(C_6–C_{10})$-aryl $(C_1–C_4)$-alkyl;
R(5) is $(C_3–C_7)$-cycloalkyl, wherein cycloalkyl is unsubstituted or substituted with hydroxy, benzyloxy, hydroxycarbonyl, or $N(R(9))_2$;
R(6a) and R(6b) independently of each other are hydrogen or $(C_1–C_8)$-alkyl which is unsubstituted or substituted by 1, 2, or 3 identical or different groups R(15);
R(8) is $(C_1–C_{10})$-alkyl, $(C_1–C_6)$-alkoxy, $(C_3–C_{10})$-cycloalkyl, $(C_3–C_7)$-cycloalkyl-$(C_1–C_4)$-alkyl, $SO_2$-$(C_1–C_4)$-alkyl, fluoro, chloro, bromo; or $(C_1–C_{10})$-alkyl, $(C_1–C_6)$-alkoxy, $(C_3–C_{10})$-cycloalkyl, $(C_3–C_7)$-cycloalkyl-$(C_1–C_4)$-alkyl or $SO_2$-$(C_1–C_4)$-alkyl in which one or more of the hydrogen atoms in the alkyl part or cycloalkyl part of the foregoing have been replaced by fluoro, chloro, or bromo; or two groups R(8) form a —O—$(CH_2)_2$O— bridge or a—$(CH_2)_4$-bridge;

R(9) is R(10) or $(C_6–C_{10})$-aryl-$(C_1–C_4)$-alkyl;
R(10) is hydrogen, nitro, $(C_1–C_6)$-alkyl, $(C_1–C_6)$-alkylcarbonyl, $(C_1–C_6)$-alkoxycarbonyl, $(C_1–C_{18})$-alkylcarbonyloxy-$(C_1–C_6)$-alkoxycarbonyl, $(C_6–C_{14})$-arylcarbonyl which is optionally substituted, $(C_6–C_{14})$-aryloxycarbonyl which is optionally substituted, or $(C_6–C_{14})$-aryl-$(C_1–C_6)$-alkoxycarbonyl which is optionally substituted in the aryl moiety;
R(11) is R(12) or $(C_1–C_4)$-alkyl which is unsubstituted or substituted by a group R(12);
R(12) is $N(R(9))_2$, $CON(R(9))_2$, CN, chloro, NR(10)—C(=NR(13)—NHR(10), C(=NR(13))NHR(10), or S(O)(=NR(9))—N(R(9))_2;
R(13) is R(10), cyano, nitro, amino, hydroxy, $(C_1–C_6)$-alkoxy, or $(C_6–C_{14})$-aryl-$(C_1–C_6)$-alkoxy which is unsubstituted or substituted in the aryl moiety by $(C_1–C_4)$-alkoxy, chloro, or $(C_1–C_4)$-alkyl;
R(15) is a six membered saturated or unsaturated heterocyclic ring with one nitrogen atom and five carbon atoms, which is unsubstituted or substituted with a group R(23);
R(23) is hydrogen, —C(=NR(9))—R(39), R(9), oxo, R(11), —NH—S(O)(=NR(9))-$(C_1–C_4)$-alkyl, or —S(O)(=NR(9))—N(R(9))_2; and
R(39) is hydrogen, $(C_8–C_{10})$-aryl, or $(C_1–C_6)$-alkyl, which are unsubstituted or substituted by cyano.
2. A compound as claimed in claim 1, wherein:
R(1) is $(C_6)$-aryl, wherein aryl is unsubstituted or substituted by a group R(8);
R(4) is hydrogen, $(C_3–C_7)$-cycloalkyl-$(C_1–C_4)$-alkyl, or $(C_1–C_4)$-alkyl;
R(5) is $(C_3–C_7)$-cycloalkyl or;
R(6a) and R(6b) independently of each other are hydrogen, methyl, ethyl, or butyl, which are unsubstituted or substituted by one or two identical or different groups R(15);
R(8) is $(C_1–C_6)$-alkyl, $(C_1–C_4)$-alkoxy, $SO_2$—$(C_1–C_4)$-alkyl, fluoro, chloro, bromo; or $(C_1–C_8)$-alkyl or $(C_1–C_4)$-alkoxy, in which 1 or more hydrogen atoms in the alkyl part have been independently replaced by fluoro, chloro, or bromo;
R(9) is R(10);
R(10) is hydrogen, nitro, or benzyloxycarbonyl;
R(11) is R(12) or methyl which is substituted by R(12);
R(12) is CN, $N(R(9))_2$, —NR(10)—C(=NR(13))—NHR(10), —C(=NR(13))—NHR(10), S(O)(=NR(9))—N(R(9))_2, or $CON(R(9))_2$;
R(13) is R(10) is hydroxy;
R(23) is oxo, —C(=NR(9))—R(39), —NH—S(O)(=NR(9))-$(C_1–C_4)$-alkyl; —S(O)(=NR(9))—N(R(9))_2, or R(11); and
R(39) is hydrogen, $(C_6–C_{10})$-aryl, $(C_1–C_6)$-alkyl, or $(C_1–C_6)$-alkyl which is substituted by cyano.
3. A compound as claimed in claim 1, wherein:
R(1) is or phenyl; which is unsubstituted or substituted by a group R(8);
R(3) is benzyl which is substituted in the aryl moiety by a group R(11);
R(4) is hydrogen;
R(5) is cyclohexyl, wherein methyl is unsubstituted or substituted with a group which is hydroxy, benzyloxy, $N(R(9))_2$, or hydroxycarbonyl;
R(6a) is hydrogen;

R(6b) is methyl or butyl, which are substituted by one or two identical or different groups R(15);

R(8) is methyl, OCH₃, SO₂CH₃, fluoro, chloro, bromo, CF₃, or OCF₃;

R(9) is R(10);

R(10) is hydrogen or benzyloxycarbonyl;

R(11) is R(12) or methyl which is substituted by R(12);

R(12) is N(R(9))₂, —NR(10)—C(=NR(13))—NHR(10), —C(=NR(13))—NHR(10), or CON(R(9))₂;

R(13) is hydrogen or hydroxy;

R(15) is piperidine, which is unsubstituted or substituted by a group R(23);

R(23) is —C(=NR(9))—R(39) or R(11);

R(39) is (C₆–C₁₀)-aryl, (C₁–C₆)-alkyl, or (C₁–C₆)-alkyl which is substituted by cyano.

4. A compound as claimed in claim 1, wherein:

R(1) is or phenyl, which is unsubstituted or substituted by a group R(8);

R(2) is hydrogen;

R(3) is benzyl which is substituted in the aryl moiety by a group R(11);

R(4) is hydrogen;

R(5) is cyclohexyl;

R(6a) is hydrogen;

R(6b) is methyl which is substituted by a group R(15), or butyl which is substituted by one or two identical or different groups R(15);

R(8) is methyl, OCH₃, SO₂CH₃, fluoro, chloro, bromo, or CF₃;

R(10) is hydrogen;

R(11) is R(12);

R(12) is —NR(10)—C(=NR(13))—NHR(10) or —C(=NR(13))—NHR(10);

R(13) is hydrogen;

R(15) is piperidine which is substituted by a group R(23);

R(23) is R(11) or —C(=NH)—R(39);

R(39) is methyl or ethyl.

5. A compound as claimed in claim 4, wherein R(3) is benzyl which is substituted in the aryl part with an amidine group.

6. A compound as claimed in claim 1, wherein R(6a) is hydrogen, and R(6b) is a group of the formula

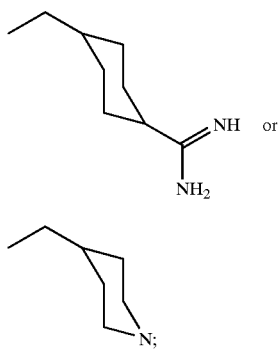

(IIIa)

(IIIb)

wherein the nitrogen atom in (IIIb) is unsubstituted or substituted with an amidine group, C(=NH)—CH₃, or C(=NH)—C₂H₅.

7. A compound as claimed in claim 1, wherein R(1) is phenyl, which are unsubstituted or substituted by a group R(8), which is methyl, trifluoromethyl, methoxy, methylsulfonyl, fluoro, chloro, or bromo.

8. A compound as claimed in claim 7, wherein R(2) and R(4) are hydrogen, R(3) is benzyl which is substituted in the aryl part with an amidine group, and R(5) is cyclohexyl.

9. A composition of matter comprising at least one of the following compounds in any stereoisomeric form, or a physiologically acceptable salt thereof:

3-(4-Carbamimidoyl-phenyl)-N-{(S)-[(1-carbamimidoyl-piperidin-4-ylmethyl)-carbamoyl]-cyclohexyl-methyl}-2-m-tolyl-propionamide, less polar diastereomer;

3-(4-Carbamimidoyl-phenyl)-N-{(S)-[(1-carbamimidoyl-piperidin-4-ylmethyl)-carbamoyl]-cyclohexyl-methyl}-2-(3-fluoro-phenyl)-propionamide, less polar diasteromer;

3-(4-Carbamimidoyl-phenyl)-N-{(S)-[(1-carbamimidoyl-piperidin-4-ylmethyl)-carbamoyl]-cyclohexyl-methyl}-2(S)-o-tolyl-propionamide, more polar diastereomer;

3-(4-Carbamimidoyl-phenyl)-N-{(S)-[(1-carbamimidoyl-piperidin-4-ylmethyl)-carbamoyl]-cyclohexyl-methyl}-2-(R)-o-tolyl-propionamide, less polar diastereomer;

3-(4-Amino-phenyl)-N-{(S)-[(1-carbamimidoyl-piperidin-4-ylmethyl)-carbamoyl]-cyclohexyl-methyl}-2-m-tolyl-propionamide, less polar diastereomer;

3-(4-Carbamimidoyl-phenyl)-N-{(S)-[(1-carbamimidoyl-piperidin-4-ylmethyl)-carbamoyl]-cyclohexyl-methyl}-2-p-tolyl-propionamide, less polar diastereomer;

3-(4-Carbamimidoyl-phenyl)-N-{(S)-[(2-carbamimidoyl-piperidin-4-ylmethyl)-carbamoyl]-cyclohexyl-methyl}-2-(3-chloro-phenyl)-propionamide hydrochloride acid salt, less polar diastereomer;

2-(4-Bromo-phenyl)-3-(4-carbamimidoyl-phenyl)-N-{(SH)-[(1-carbamimidoyl-piperidin-4-ylmethyl)-carbamoyl]-cyclohexyl-methyl}-propionamide hydrochloride acid salt, less polar diasteromer;

(3-(4-Carbamimidoyl-phenyl)-N-{(S)-[(1-carbamimidoyl-piperidin-4-ylmethyl)-carbamoyl]-cyclohexyl-methyl}-2-(2-fluoro-phenyl)-propionamide trifluoroacetic acid salt;

(3-(4-Carbamimidoyl-phenyl)-N-{(S)-[(1-carbamimidoyl-piperidin-4-ylmethyl)-carbamoyl]-cyclohexyl-methyl}-2-(4-chloro-phenyl)-propionamide trifluoroacetic acid salt, less polar diastereomer;

(3-(4-Carbamimidoyl-phenyl)-N-{(S)-[(1-carbamimidoyl-piperidin-4-ylmethyl)-carbamoyl]-cyclohexyl-methyl}-2-phenyl-propionamide trifluoroacetic acid salt, less polar diastereomer;

2-(3-Bromo-phenyl)-3-(4-carbamimidoyl-phenyl)-N-((S)-cyclohexyl-{[1-(1-imino-ethyl)-piperidin-4-ylmethyl]-carbamoyl}-methyl)-propionamide trifluoroacetic acid salt, less polar diastereomer;

(3-(4-Carbamimidoyl-phenyl)-N-{(S)-[(1-carbamimidoyl-piperidin-4-ylmethyl)-carbamoyl]-cyclohexyl-methyl}-2-(3-trifluoromethyl-phenyl)-propionamide trifluoroacetic acid salt, less polar diastereomer;

(3-(4-Carbamimidoyl-phenyl)-N-{(S)-[(1-carbamimidoyl-piperidin-4-ylmethyl)-carbamoyl]-cyclohexyl-methyl}-2-(2-chloro-phenyl)- propionamide trifluoroacetic acid salt, less polar diastereomer; or (3-(4-Carbamimidoyl-phenyl)-N-{(S)-[(1-carbamimidoyl-piperidin-4-ylmethyl)-carbamoyl]-cyclohexyl-methyl}-2-(4-trifluoromethyl-phenyl)-propionamide trifluoroacetic acid salt, less polar diastereomer.

10. A process for the preparation of a compound as claimed in claim 1, which comprises the steps of:

(a1) protecting the carboxylic function of a compound of the formula IV:

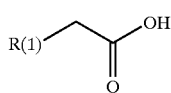
(IV)

wherein R(1) is as defined in claim 1;

(a2) reacting such a protected compound of the formula IVa;

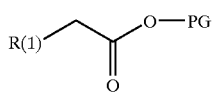
(IVa)

with a compound of formula V:

R(3a)-LG    (V)

wherein

R(3a) is $(C_6-C_{10})$-aryl-$(C_1-C_4)$-alkyl which is substituted in the aryl or alkyl moiety by a group (R29); where R(29) is R(30) or $(C_1-C_4)$-alkyl, which is unsubstituted or substituted by R(30); wherein R(30) is $N(R(31))_2$, $CON(R(9))_2$, $NO_2$, chloro, or CN, and where groups R(30), if present more than one time in the molecule, are independent of each other and can be identical or different; where R(31) is $(C_1-C_6)$-alkyl, $(C_6-C_{10})$-aryl-$(C_1-C_4)$-alkyl, $(C_1-C_6)$-alkoxycarbonyl, or $(C_1-C_6)$-alkoxycarbonyl, and where groups R(31), if present more than one time in the molecule, are independent of each other and can be identical or different;

and wherein PG is an easily cleavable protecting group and LG is a leaving group;

(a3) reacting the resulting product with a compound of formula VI:

R(2)-LG    (VI)

wherein R(2) is $(C_1-C_4)$-alkyl and LG is as defined above, in the presence of a base to give a compound of formula VII:

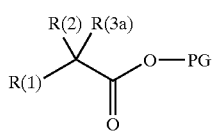
(VII)

and deprotecting a compound of the formula VII to give a compound of the formula VIII:

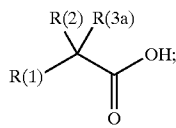
(VIII)

(a4) coupling a compound of the formula VIII with a compound of formula IX:

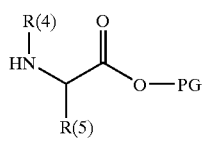
(IX)

wherein PG is an easily cleavable protecting group and R(4) and R(5) are as defined in claim 1, to give a compound of formula X:

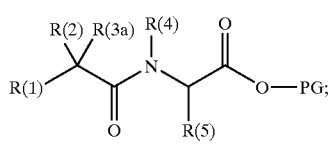
(X)

(a5) converting a compound of the formula X into a compound of the formula XI:

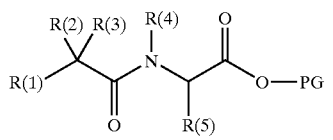
(XI)

wherein R(3) is as claimed in claim 1; and (a6) saponification of a compound of the formula XI and coupling the resulting compound with a compound of the formula XIII:

HNR(6a)R(6b)    (XIII)

wherein R(6a) and R(6b) are as defined in claim 1, thereby resulting in a compound of formula (I).

11. A process for the preparation of a compound as claimed in claim 1, which comprises the steps of:

(a1) protecting the carboxylic function of a compound of the formula IV:

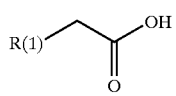
(IV)

wherein R(1) is a defined in claim 1;

(a2) reacting such a protected compound of the formula IVa:

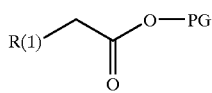
(IVa)

with a comound of formula V:

$R(3a)\text{-}LG$ (V)

wherein

R(3a) is $(C_6-C_{10})$-aryl-$(C_1-C_4)$-alkyl which is substituted in the aryl or alkyl moiety by a group R(29); where R(29) is R(30) or $(C_1-C_4)$-alkyl, which is unsubstituted or substituted by R(30); where R(30) is $N(R(31))_2$, $NO_2$, chloro, or CN, and where groups R(30), if present more than one time in the molecule, are independent of each other and can be identical or different; where R(31) is $(C_1-C_6)$-alkyl, $(C_6-C_{10})$-aryl-$(C_1-C_4)$-alkyl, $(C_1-C_6)$-alkylcarbonyl, or $(C_1-C_6)$-alkoxycarbonyl, and where groups R(31), if present more than one time in the molecule, are independent of each other and can be identical or different;

and wherein PG is an easily cleavable protecting group and LG is a leaving group;

in the presence of a base to give a compound of formula VII:

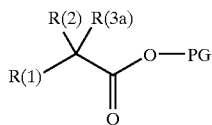
(VII)

where R(2) is hydrogen, and deprotecting a compound of the formula VII to give a compound of the formula VIII:

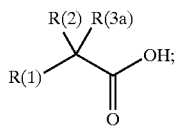
(VIII)

(a3) coupling a compound of the formula VIII with a compound of formula IX:

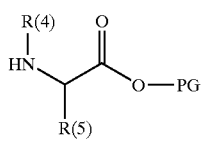
(IX)

wherein RG is an easily cleavable protecting group and R(4) and R(5) are as defined in claim 1, in the presence of a suitable coupling reagent to give a compound of formula X:

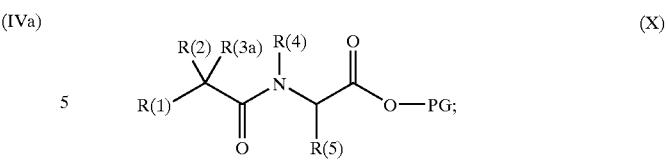
(X)

(a4) converting a compound of the formula X into a compound of the formula XI:

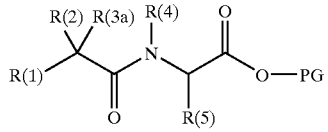
(XI)

wherein R(3) is as claimed in claim 1; and (a5) saponification of a compound of the formula XI and coupling the resulting compound with a compound of the formula XIII:

$HNR(6a)R(6b)$ (XIII)

wherein R(6a) and R(6b) are as defined in claim 1, thereby resulting in a compound of formula (I).

12. A process for the preparation of a compound as claimed in claim 1, which comprises the steps of:

(a1) protecting the carboxylic function of a compound of the formula IV:

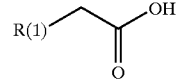
(IV)

wherein R(1) is as defined in claim 1, and reacting such a protected compound of the formula IVa:

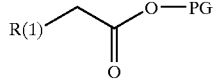
(IVa)

with a compound of formula V:

$R(3a)\text{-}LG$ (V)

wherein

R(3a) is $(C_6-C_{10})$-aryl-$(C_1-C_4)$-alkyl which is substituted in the aryl or alkyl moiety by a group R(29); wherein R(29) is R(30) or $(C_1-C_4)$-alkyl, which is unsubstituted or substituted by R(30); wherein R(30) is $N(R(31))_2$, $CON(R(9))_2$, $NO_2$, chloro, or CN, and where groups R(30), if present more than one time in the molecule, are independent of each other and can be identical or different; where R(31) is $(C_1-C_6)$-alkyl, $(C_6-C_{10})$-aryl-$(C_1-C_4)$-alkyl, $(C_1-C_6)$-alkylcarbonyl, or $(C_1-C_6)$-alkoxycarbonyl, and where groups R(31), if present more than one time in the molecule, are independent of each other and can be identical or different;

and wherein PG is an easily cleavable protecting group and LG is a leaving group;

(a3) reacting the resulting product with a compound of formula VI:

R(2)-LG    (VI)

wherein R(2) is (C$_1$–C$_4$)-alkyl and LG is as defined above, in the presence of a base to give a compound of formula VII:

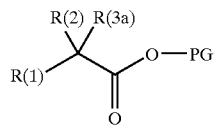    (VII)

and deprotecting a compound of the formula VII to give a compound of the formula VIII:

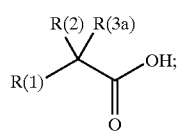    (VIII)

(a4) coupling a compound of the formula VIII with a compound of formula IX:

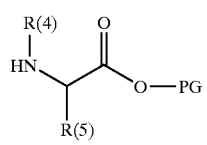    (IX)

wherein PG is an easily cleavable protecting group, in the presence of a suitable coupling reagent to give a compound of formula X:

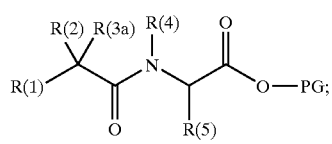    (X)

(a5) saponification of a compound of the formula X and coupling the resulting compound above with a compound of the formula XIII:

HNR(6a)R(6b)    (XIII)

wherein R(6a) and R(6b) are as defined in claim 1, to give a compound of formula XXV:

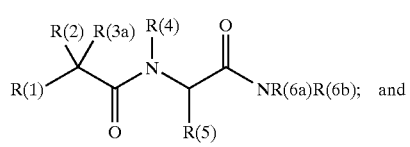    (XXV)

(a6) converting R(3a) in the compound of formula XXV to R(3) thereby resulting in a compound of formula (I).

13. A process for the preparation of a compound as claimed in claim 1, which comprises the steps of:

(a1) protecting the carboxylic function of a compound of the formula IV:

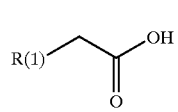    (IV)

wherein R(1) is a defined in claim 1;

(a2) reacting such a protected compound of the formula IVa:

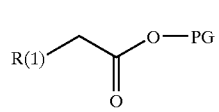    (IVa)

with a compound of formula:

R(3a)-LG    (V)

wherein

R(3a) is (C$_6$–C$_{10}$)-aryl-(C$_1$–C$_4$)-alkyl which is substituted in the aryl or alkyl moiety by a group (R29); where R(29) is R(30) or (C$_1$–C$_4$)-alkyl, which is unsubstituted or substituted by R(30); where R(30) is N(R(31))$_2$, CON(R(9))$_2$, NO$_2$, chloro, or CN, and where groups R(30), if present more than one time in the molecule, are independent of each other and can be identical or different; where R(31) is (C$_1$–C$_6$)-alkyl, (C$_6$–C$_{10}$)-aryl-(C$_1$–C$_4$)-alkyl, (C$_1$–C$_6$)-alkylcarbonyl, or (C$_1$–C$_6$)-alkoxycarbonyl, and where groups R(31), if present more than one time in the molecule, are independent of each other and can be identical or different;

and wherein PG is an easily cleavable protecting group and LG is a leaving group;

in the presence of a base to give a compound of formula VII:

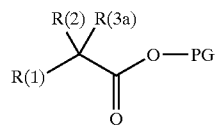    (VII)

where R(2) is hydrogen, and deprotecting a compound of the formula VII to give a compound of the formula VII:

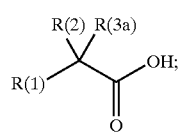    (VIII)

(a3) coupling a compound of the formula VII with a compound of formula IX:

(IX)

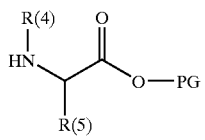

wherein PG is an easily cleavable protecting group and R(4) and R(5) are as defined in claim 1, in the presence of a suitable coupling reagent to give a compound of formula X:

(X)

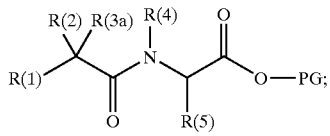

(a4) saponification of a compound of the formula X and coupling the resulting compound with a compound of the formula XIII:

(HNR(6a)R(6b))　(XIII)

wherein R(6a) and R(6b) are as defined in claim 1, to give a compound of formula XXV:

(XXV)

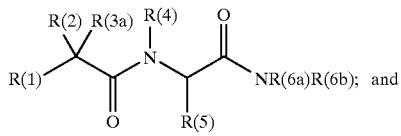

(a5) converting R(3a) in the compound of formula XXV to R(3) thereby resulting in a compound of formula (I).

14. A process for the preparation of a compound as claimed in claim 1, which comprises the steps of:

(a1) coupling a compound of the formula IV or IVa (IV)

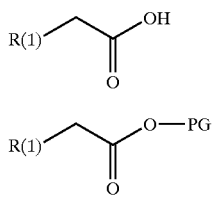

(IVa)

wherein R(1) is as defined in claim 1 and PG is an easily cleabable leaving group, to a compound of the formula Vb, (Vb)

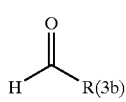

wherein R(3b) is $(C_6-C_{10})$-aryl or $(C_6-C_{10})$-aryl-$(C_1-C_3)$-alkyl, where the aryl moiety is substituted by R(30), in a suitable solvent and following hydrogenation of the double bond to yield a compound of the formula VIII:

(VIII)

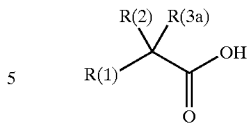

where R(2) is hydrogen, R(3b) is as defined above, and R(3a) is $(C_6-C_{10})$-aryl-$(C_1-C_4)$-alkyl which is substituted in the aryl or alkyl moiety by a group R(29); where R(29) is R(30) or $(C_1-C_4)$-alkyl, which is unsubstituted or substituted by R(30); where R(30) is $N(R(31))_2$, $CON(R(9))_2$, $NO_2$, chloro, or CN, and where groups R(30), if present more than one time in the molecule, are independent of each other and can be identical or different; where R(31) is $(C_1-C_6)$-alkyl, $(C_8-C_{10})$-aryl-$(C_1-C_4)$-alkyl, $(C_1-C_{C6})$-alkylcarbonyl, or $(C_1-C_6)$-alkoxycarbonyl, and where groups R(31), if present more than one time in the molecule, are independent of each other and can be identical or different;

(a2) coupling a compound of the formula VII with a compound of formula IX:

(IX)

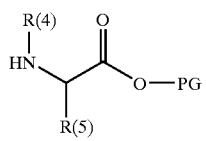

wherein PG is an easily cleavable protecting group and R(4) and R(5) are as defined above, to give a compound of formula X:

(X)

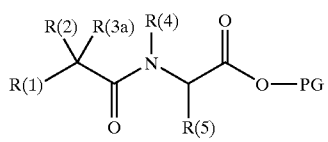

(a3) converting a compound of the formula X into a compound of the formula XI:

(XI)

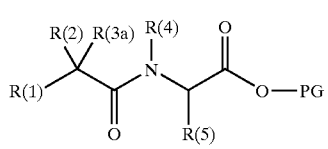

where R(3) is as defined in claim 1; and (a4) saponification of a compound of the formula XI and coupling the resulting compound with a compound of the formula XIII:

HNR(6a)R(6b)　(XIII)

wherein R(6a) and R(6b) are as defined in claim 1, thereby resulting in a compound of formula (I).

15. A process for the preparation of a compound as claimed in claim 1, which comprises the steps of:

(a1) coupling a compound of the formula IV or IVa:

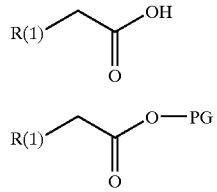

(IV)

(IVa)

wherein R(1) is as defined in claim 1 and PG is an easily cleavable protecting group, to a compound of the formula Vb:

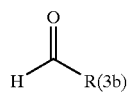

(Vb)

wherein R(3b) is $(C_6-C_{10})$-aryl or $(C_6-C_{10})$-aryl-$(C_1-C_3)$-alkyl, where the aryl moiety is substituted by R(30), in a suitable solvent and following hydrogenation of the double bond to yield a compound of the formula VIII:

(VIII)

where R(2) is hydrogen, R(3b) is as defined above, and R(3a) is $(C_6-C_{10})$-aryl-$(C_1-C_4)$-alkyl which is substituted in the aryl or alkyl moiety by a group R(29); where R(29) is R(30) or $(C_1-C_4)$-alkyl, which is unsubstituted or substituted by R(30); where R(30) is $N(R(31))_2$, $CON(R(9))_2$, $NO_2$, chloro, or CN, and where groups R(30), if present more than one time in the molecule, are independent of each other and can be identical or different, where R(31) is $(C_1-C_6)$-alkyl, $(C_6-C_{10})$-aryl-$(C_1-C_4)$-alkyl, $(C_1-C_6)$-alkylcarbonyl, or $(C_1-C_6)$-alkoxycarbonyl, and where groups R(31), if present more than one time in the molecule, are independent of each other and can be identical or different;

(a2) coupling a compound of the formula VIII with a compound of formula IX:

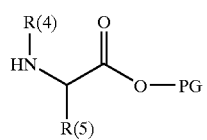

(IX)

wherein PG is an easily cleavable protecting group and R(4) and R(5) are as defined in claim 1, to give a compound of formula X:

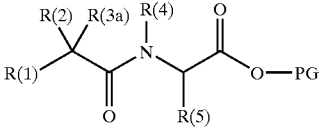

(X)

(a3) saponification of a compound of the formula X and coupling the resulting compound with a compound of the formula XIII:

$HNR(6a)R(6b)$  (XIII)

where R(6a) and R(6b) are as defined in claim 1, to give a compound of formula XXV:

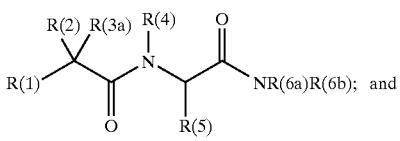

(XXV)

(a4) transforming the group (R3a) to R(3), where R(3) is as defined in claim 1, thereby resulting in a compound of formula (I).

16. A process for the preparation of a compound as claimed in claim 1, which comprises the steps of:

(b1) starting from a compound of the formula VII:

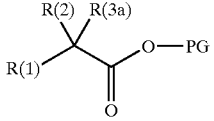

(VII)

wherein R(1) and R(2) are as defined in claim 1, PG is an easily cleavable protecting group, and R(3a) is $(C_6-C_{10})$-aryl-$(C_1-C_4)$-alkyl which is substituted in the aryl or alkyl moiety by a group R(29); where R(29) is R(30) or $(C_1-C_4)$-alkyl, which is unsubstituted or substituted by R(30); where R(30) is $N(R(31))_2$, $CON(R(9))_2$, $NO_2$, chloro, or CN, and where groups R(30), if present more than one time in the molecule, are independent of each other and can be identical or different, where R(31) is $(C_1-C_6)$-alkyl, $(C_6-C_{10})$-aryl-$(C_1-C_4)$-alkyl, $(C_1-C_6)$-alkylcarbonyl, or $(C_1-C_6)$-alkoxycarbonyl, and where groups R(31), if present more than one time in the molecule, are independent of each other and can be identical or different;

converting a compound of the formula VII into a compound of the formula VIIa:

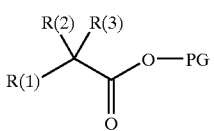

(VIIa)

wherein R(3) is as defined in claim 1, and deprotecting the compound of the formula VIIa to give a compound of the formula XIV:

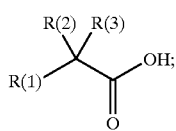
(XIV)

(b2) coupling a compound of the formula XIV with a compound of the formula XVII:

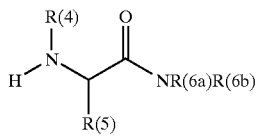
(XVII)

thereby resulting in a compound of the formula (I).

17. A process for the preparation of a compound as claimed in claim 1, which comprises the steps of:

(a) coupling a compound of the formula XVIII shown bound to a carrier

as follows:

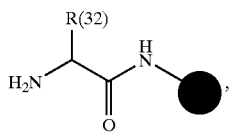
(XVIII)

wherein

R(32) is hydrogen or (C$_1$–C$_6$)-alkyl which is optionally substituted one or two times by identical or different groups R(33); where R(33) is a six membered saturated or unsaturated heterocyclic ring with one nitrogen atom and five carbon atoms;

with a compound of the formula XIX:

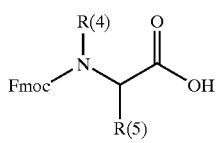
(XIX)

wherein R(4) and R(5) are as defined in claim 1, to give a compound of the formula XX:

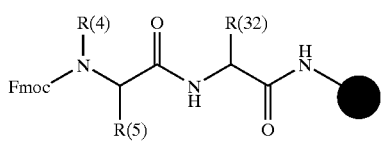
(XX)

(b) and after deprotecting the compound of the formula XX with a base, coupling the deprotected compound XX to a compound of the formula VIII:

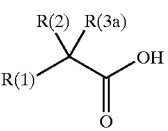
(VIII)

wherein R(1) and R(2) are as defined in claim 1 and R(3a) is (C$_6$–C$_{10}$)-aryl-(C$_1$–C$_4$)-alkyl which is substituted in the aryl or alkyl moiety by a group R(29); where R(29) is R(30) or (C$_1$–C$_4$)-alkyl, which is unsubstituted or substituted by R(30); where R(30) is N(R(31))$_2$, CON(R(9))$_2$, NO$_2$, chloro, or CN, and where groups R(30), if present more than one time in the molecule, are independent of each other and can be identical or different; where R(31) is (C$_1$–C$_6$)-alkyl, (C$_6$–C$_{10}$)-aryl-(C$_1$–C$_4$)-alkyl, (C$_1$–C$_6$)-alkylcarbonyl, or (C$_1$–C$_6$)-alkoxycarbonyl, and where groups R(31), if present more than one time in the molecule, are independent of each other and can be identical or different;

to give a compound of the formula XXII:

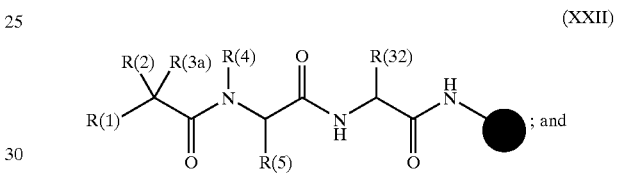
(XXII)

(c) transforming the group (R3a) to R(3), if necessary, to yield a compound of the formula XXIII

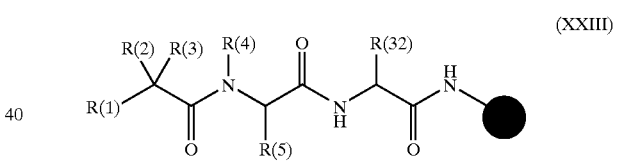
(XXIII)

and cleaving a compound of the formula XXII or XXIII off the carrier thereby resulting in a compound of the formula (I).

18. A process for the preparation of a compound as claimed in claim 1, which comprises the steps of:

(a) coupling a compound of the formula XVIII show bound to a carrier as follows:

(XVIII)

wherein

R(32) is hydrogen or (C$_1$–C$_8$)-alkyl which is optionally substituted one or two times by identical or different groups (R33); where R(33) is a six membered saturated or unsaturated heterocyclic ring with one nitrogen atom and five carbon atoms;

with a compound of the formula XIX:

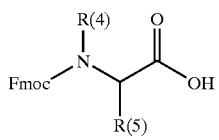
(XIX)

wherein R(4) and R(5) are as defined in claim 1, to give a compound of the formula XX:

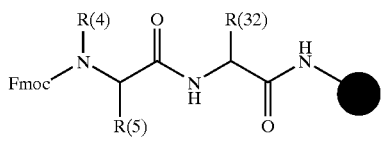
(XX)

(b) and after deprotecting a compound of the formula XX with a base, coupling the deprotected compound XX to a compound of the formula VIII:

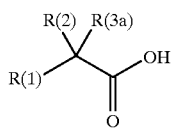
(VIII)

wherein R(1) and R(2) are as defined in claim 1 and R(3a) is $(C_6–C_{10})$-aryl-$(C_1–C_4)$-alkyl which is substituted in the aryl or alkyl moiety by a group R(29); where R(29) is R(30) or $(C_1–C_4)$-alkyl, which is unsubstituted or substituted by R(30); where R(30) is $N(R(31))_2$, $CON(R(9))_2$, $NO_2$, chloro, or CN, and where groups R(30), if present more than one time in the molecule, are independent of each other and can be identical or different; where R(31) is $(C_1–C_6)$-alkyl, $(C_6–C_{10})$-aryl-$(C_1–C_4)$-alkyl, $(C_1–C_6)$-alkylcarbonyl, or $(C_1–C_6)$-alkoxycarbonyl, and where groups R(31), if present more than one time in the molecule, are independent of each other and can be identical or different;

to give a compound of the formula XXIII:

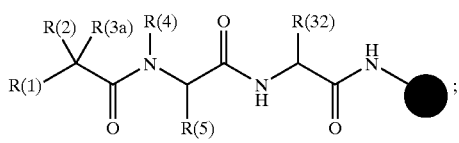
(XXII)

(c) converting a compound of the formula XXII to a compound of the formula XXIII (i.e. transforming the group R(3a) to a group R(3))

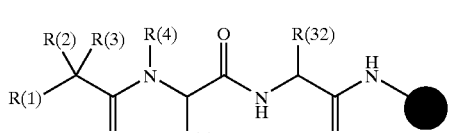
(XXIII)

wherein R(3) is as defined in claim 1; and (d) cleaving a compound of the formula XXIII off the carrier thereby producing a compound of the formula (I).

19. A process for the preparation of a compound as claimed in claim 1, which comprises the steps of:

(a) coupling a compound of the formula XVIII shown bound to a carrier

as follows:

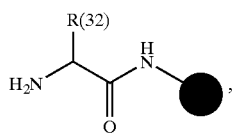
(XVIII)

wherein

R(32) is hydrogen or $(C_1–C_8)$-alkyl which can be substituted one or two times by identical or different groups R(33); where R(33) is a six membered saturated or unsaturated heterocyclic ring with one nitrogen atom and five carbon atoms;

with a compound of the formula XIX:

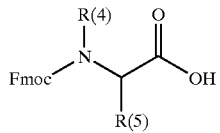
(XIX)

wherein R(4) and R(5) are as defined in claim 1, to give a compound of the formula XX:

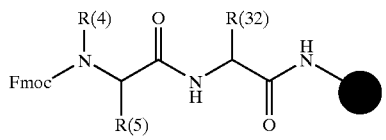
(XX)

(b) and after deprotecting the compound of the formula XX with a base, coupling the deprotected compound XX to a compound of the formula XIV:

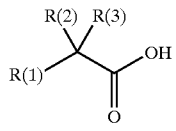
(XIV)

wherein R(1), R(2), and R(3) are as defined in claim 1, to give a compound of the formula XXIII:

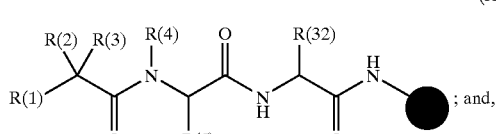
(XXIII)
; and, (c) cleaving a compound of the formula XXIII off the carrier thereby resulting in a compound of the formula (I).

20. A pharmaceutical composition, comprising an effective amount of a compound as claimed in claim 1 and a pharmaceutically acceptable carrier.

21. A method of inhibiting factor Xa comprising the step of contacting factor Xa or a material containing factor Xa, with a compound as claimed in claim 1.

22. A method of inhibiting factor Xa comprising the step of administering to a patient in need thereof an effective amount of a compound as claimed in claim 1.

23. A method of inhibiting blood clotting or coagulation comprising the step of contacting blood with an effective amount of a compound as claimed in claim 1.

24. A method of reducing or inhibiting blood clotting or coagulation comprising the step of administering to a patient in need thereof an effective amount of a compound as claimed in claim 1.

25. A method of treatment or prophylaxis of a cardiovascular disorder or thromboembolic condition comprising the step of administering to a patient in need thereof an effective amount of a compound as claimed in claim 1.

26. A method of treatment or prophylaxis of a cardiovascular disorder or a thromboembolic condition as claimed in claim 25 where the cardiovascular disorder or thromboembolic condition is restenosis, restenosis following angioplasty, reocclusion prophylaxis, conditions after coronary bypass operations, aterial, venous and microcirculatory disease states, cardiac infarction, angina pectoris, thromboembolic diseases, thromboses, embolism, adult respiratory distress syndrome, multi-organ failure, stroke, or disseminated intravascular coagulation clotting.

27. A method of treatment or prophylaxis of a cardiovascular disorder or a thromboembolic condition as claimed in claim 25, wherein the cardiovascular disorder or thromboembolic condition is deep vein or proximal vein thormbosis.

* * * * *

UNITED STATES PATENT AND TRADEMARK OFFICE
CERTIFICATE OF CORRECTION

PATENT NO. : 6,759,420 B1
DATED : July 6, 2004
INVENTOR(S) : Elisabeth Defossa et al.

It is certified that error appears in the above-identified patent and that said Letters Patent is hereby corrected as shown below:

Column 81,
Line 44, "R(1) is $C_6$ aryl" should read -- R(1) is $(C_6)$-aryl --;
Line 47, "R(3) is $(C_6\text{-})$-aryl-$(C_1\text{-}C_4)$-alkyl" should read -- R(3) is $(C_6)$-aryl-$(C_1\text{-}C_4)$-alkyl --.
Line 50, "$(C_6\text{-}C_{10})$-aryl" should read -- $(C_6\text{-}C_{10})$-aryl- --.

Column 82,
Line 34, delete "or";

Column 84,
Lines 56-59, delete "2-(3-Bromo-phenyl)-3-(4-carbamimidoyl-phenyl)-N-((S)-cyclohexyl-{[-(1-imino-ethyl)-piperidin-4-ylmethyl]-carbamoyl}-methyl)-propionamide trifluoroacetic acid salt, less polar diastereomer;".

Signed and Sealed this

Fourteenth Day of December, 2004

JON W. DUDAS
*Director of the United States Patent and Trademark Office*